(12) United States Patent
Snyder

(10) Patent No.: US 6,635,061 B1
(45) Date of Patent: Oct. 21, 2003

(54) APPARATUS AND METHOD FOR TARGETING AND/OR INSTALLING FASTNERS INTO AN INTRAMEDULLARY NAILS

(76) Inventor: Samuel J. Snyder, 57 Leach Ave., Park Ridge, NJ (US) 07656

( * ) Notice: Subject to any disclaimer, the term of this patent is extended or adjusted under 35 U.S.C. 154(b) by 109 days.

(21) Appl. No.: 09/658,145

(22) Filed: Sep. 8, 2000

Related U.S. Application Data

(63) Continuation of application No. 09/190,033, filed on Nov. 11, 1998, now Pat. No. 6,129,729.

(51) Int. Cl.7 .............................................. A61B 17/58
(52) U.S. Cl. ....................................................... 606/96
(58) Field of Search .............................. 606/62, 63, 64, 606/96, 97, 98, 102, 104, 130

(56) References Cited

U.S. PATENT DOCUMENTS

| | | |
|---|---|---|
| 4,622,959 A | 11/1986 | Marcus |
| 4,667,664 A | 5/1987 | Taylor et al. |
| 4,848,327 A | 7/1989 | Perdue |
| 4,865,025 A | 9/1989 | Buzzi et al. |
| 4,913,137 A | 4/1990 | Azer et al. |
| 4,969,889 A | 11/1990 | Greig |
| 5,013,317 A | 5/1991 | Cole et al. |
| 5,030,222 A | 7/1991 | Calandruccio et al. |
| 5,049,151 A | 9/1991 | Durham et al. |
| 5,411,503 A | 5/1995 | Hollstien et al. |
| 5,417,688 A | 5/1995 | Elstrom et al. |
| 5,478,343 A | 12/1995 | Ritter |
| 5,514,145 A | 5/1996 | Durham et al. |
| 6,129,729 A * | 10/2000 | Snyder ........................ 606/72 |

OTHER PUBLICATIONS

Innomed—Instruments For Orthopedic Surgery, 1997, pp. 1–40.

UNIFLEX™ Tibial Nail Surgical Technique, Biomet Inc., pp. 1–11.

Fracture Management—ZMS Intramedullary Fixation, The ZMS Femoral Nail, The ZMS Tibial Nail, The ZMS Recon Nail, Ordering Information, 1992, pp. 1–16.

(List continued on next page.)

Primary Examiner—David O. Reip
Assistant Examiner—D. Jacob Davis
(74) Attorney, Agent, or Firm—Frommer Lawrence & Haug LLP; Dennis M. Smid

(57) ABSTRACT

A method and apparatus for installing a number of distal screws into an intramedullary nail implanted in a patient. The apparatus includes a foundation which is fixedly coupled to the patient, a targeting insert having a targeting spike, a guiding insert for guiding an installation tool used in installing a distal screw, a targeting/guiding device coupled to the foundation and adaptable for having the targeting insert and the guiding insert coupled thereto, and a handle removably coupled to the targeting/guiding device. When the targeting insert is coupled to the targeting/guiding device, the targeting/guiding device may be movable by an operator or surgeon with the use of the handle so as to align the targeting spike with a respective distal screw hole in the intramedullary nail. Afterwards, the targeting/guiding device may be locked in place by the operator or surgeon with the use of the handle, the targeting insert removed, and the guiding insert coupled to the targeting/guiding device. Such guiding insert enables the installation tool to be properly guided when installing a distal screw into the respective distal screw hole.

6 Claims, 43 Drawing Sheets

OTHER PUBLICATIONS

The Universal Nailing System—A Systematic Approach to IM Nailing; AO/ASIF—Original Instruments and Implants of the Association for the Study of Internal Fixation; SYNTHESIS®, 1989, pp. 1–6.

The Universal Nailing System—Technique Guide; AO/ASIF—Original Instruments of Association for the Study of Internal Fixation; SYNTHESIS®, 1989, pp. 1–49.

Surgical Technique—RUSSELL—TAYLOR® Tibial/Delta™ Tibial Nail System, Smith and Nephew, by Thomas A. Russell, M.D.et al., pp. 1–40.

Smith & Nephew Richards—The Smith & Nephew Richards Family of Femoral Interlocking Nails, Surgical Technique, by Thomas A. Russell, M.D. et al., pp. 1–62.

Osteo IC–NAIL—Without Cortical Reaming—Femoral and Tibial Interlocking–Compression–Nail, pp. 1–16.

Osteo IC–NAIL—Without Cortical Reaming—Femoral and Tibial Tibial Interlocking–Compression–Nail, pp. 1–16.

Innomed—Instruments For Orthopedic Surgery Special Sections For Hip, Knee, Trauma, Positioning and Extraction/Revision Instruments, 1997, pp. 1–36.

* cited by examiner

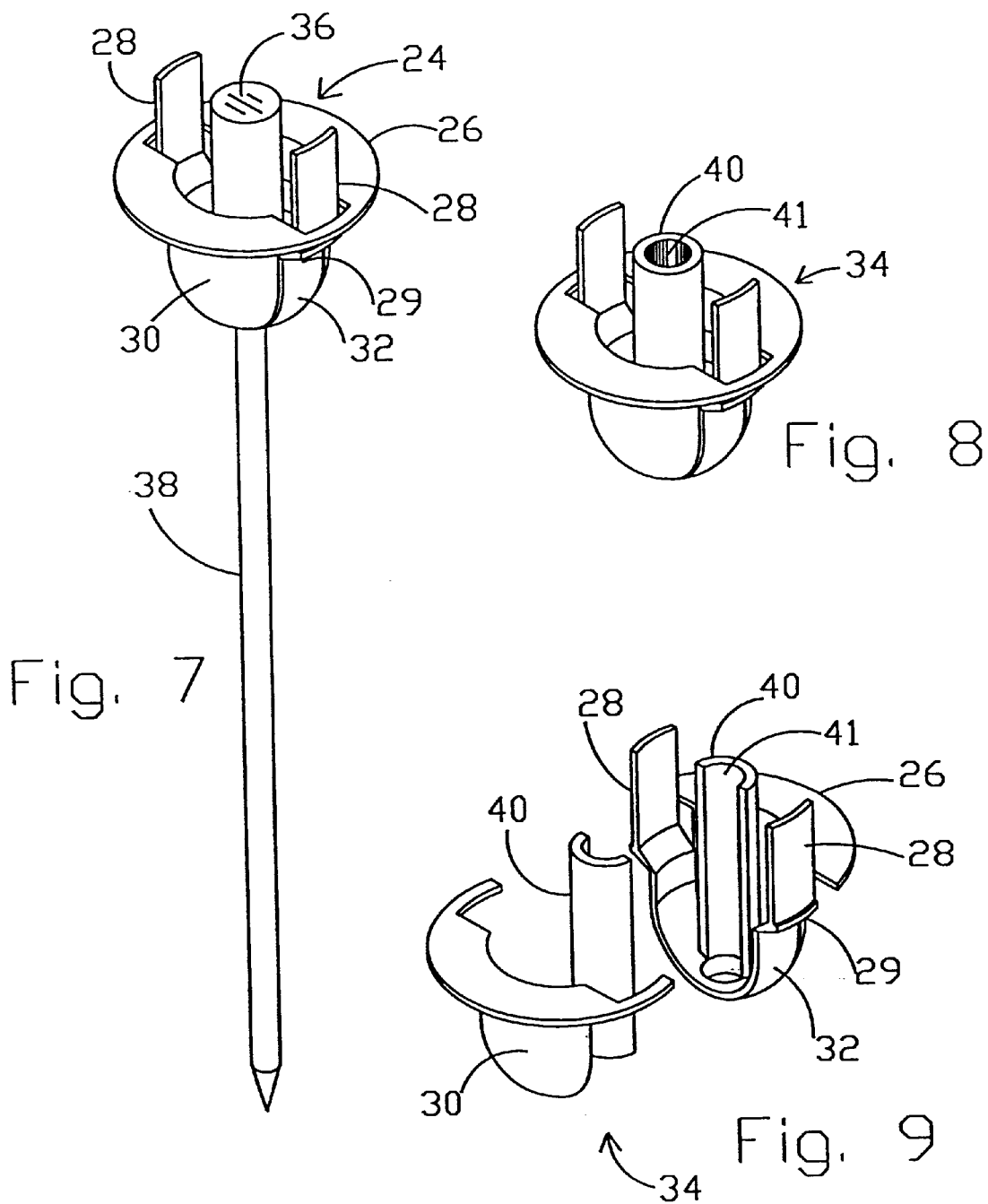

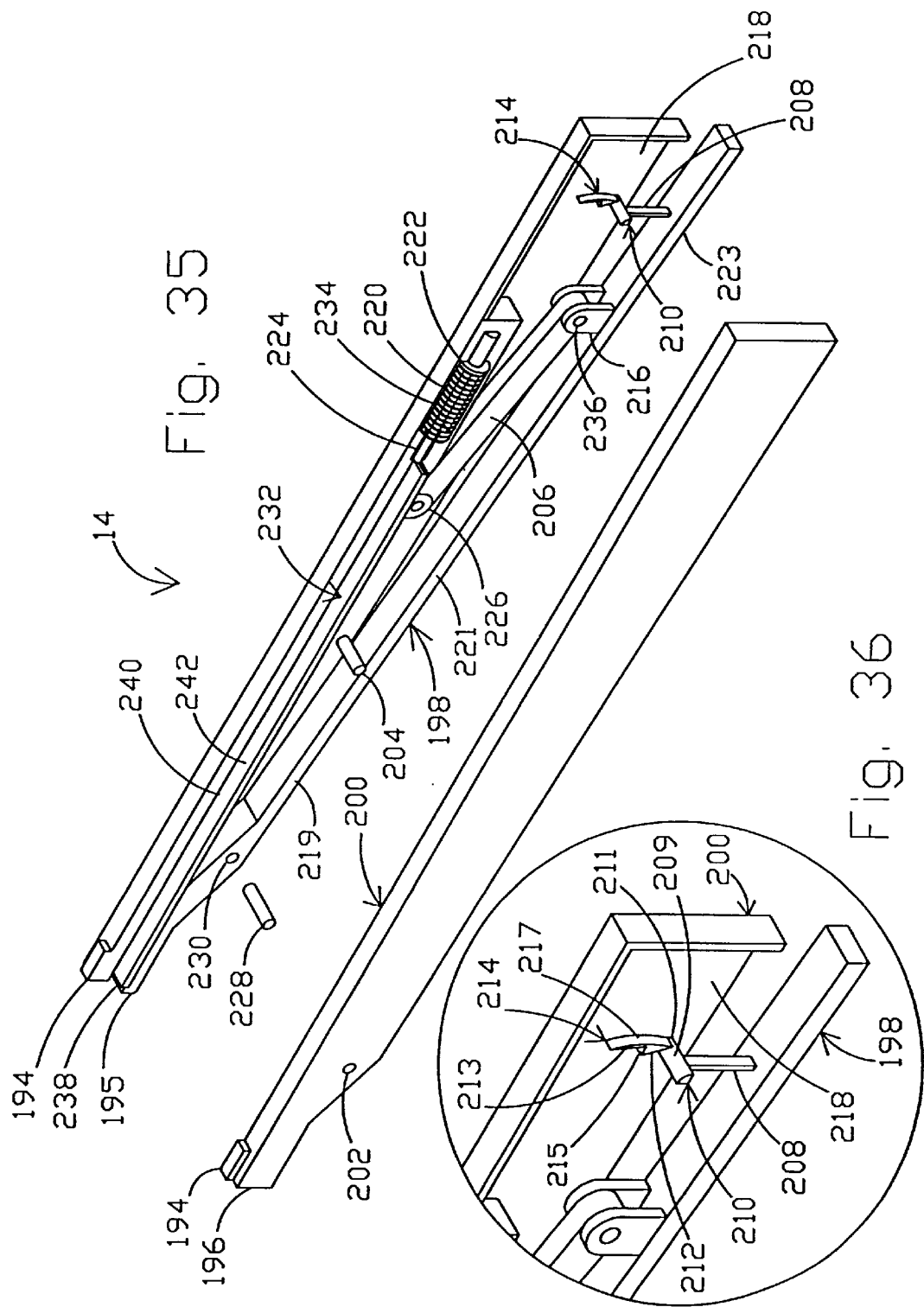

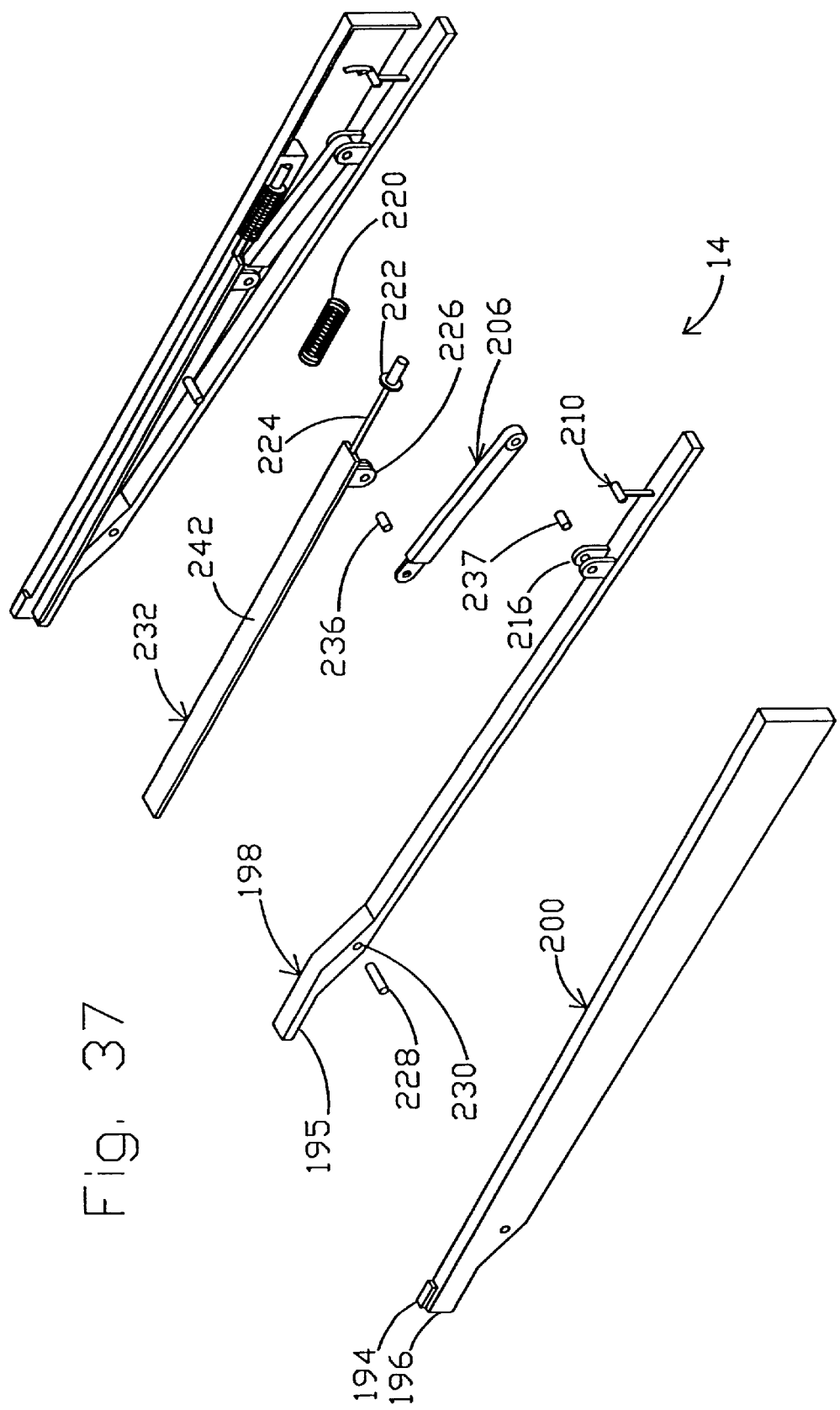

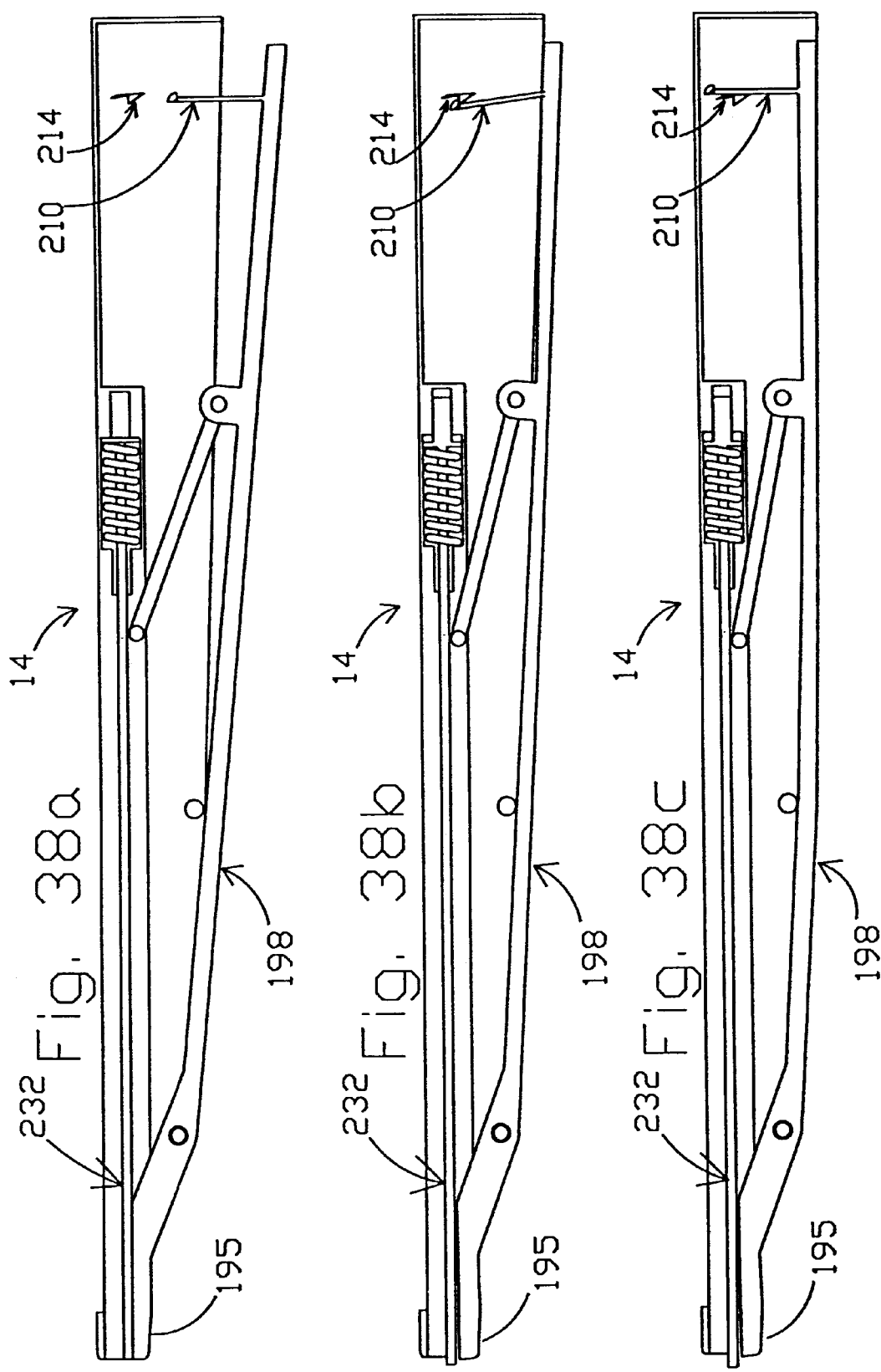

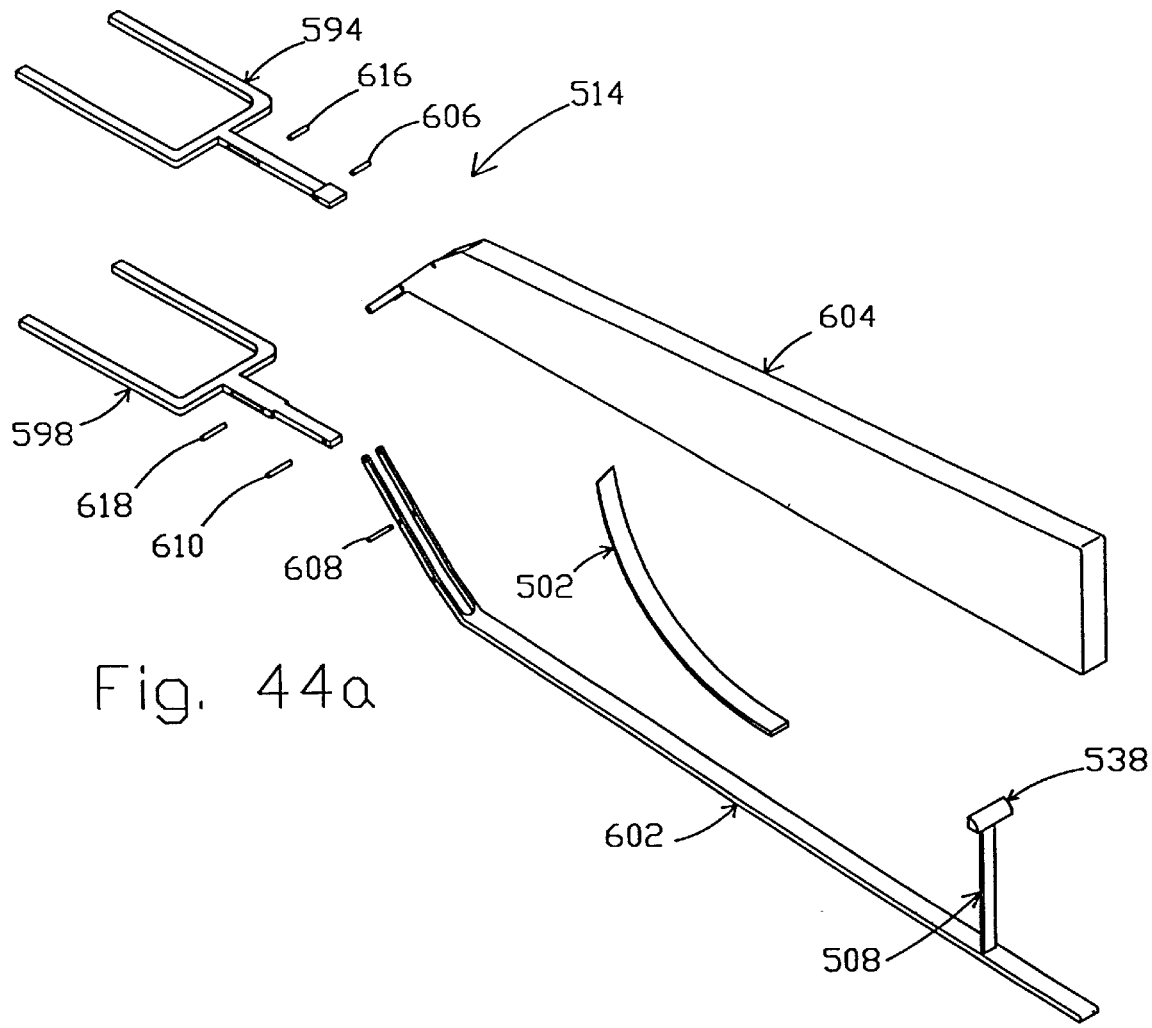

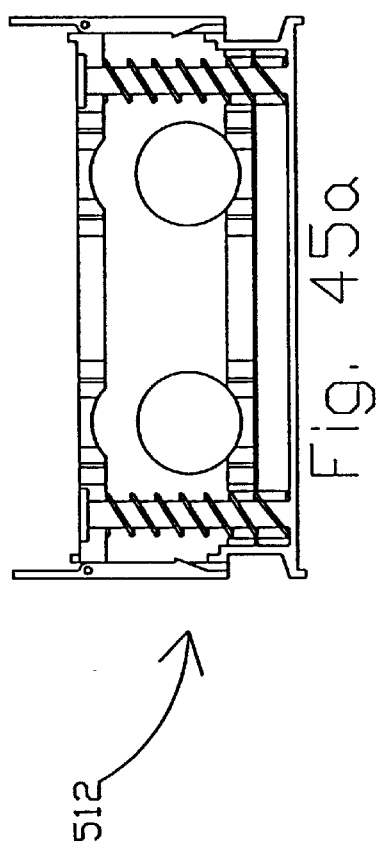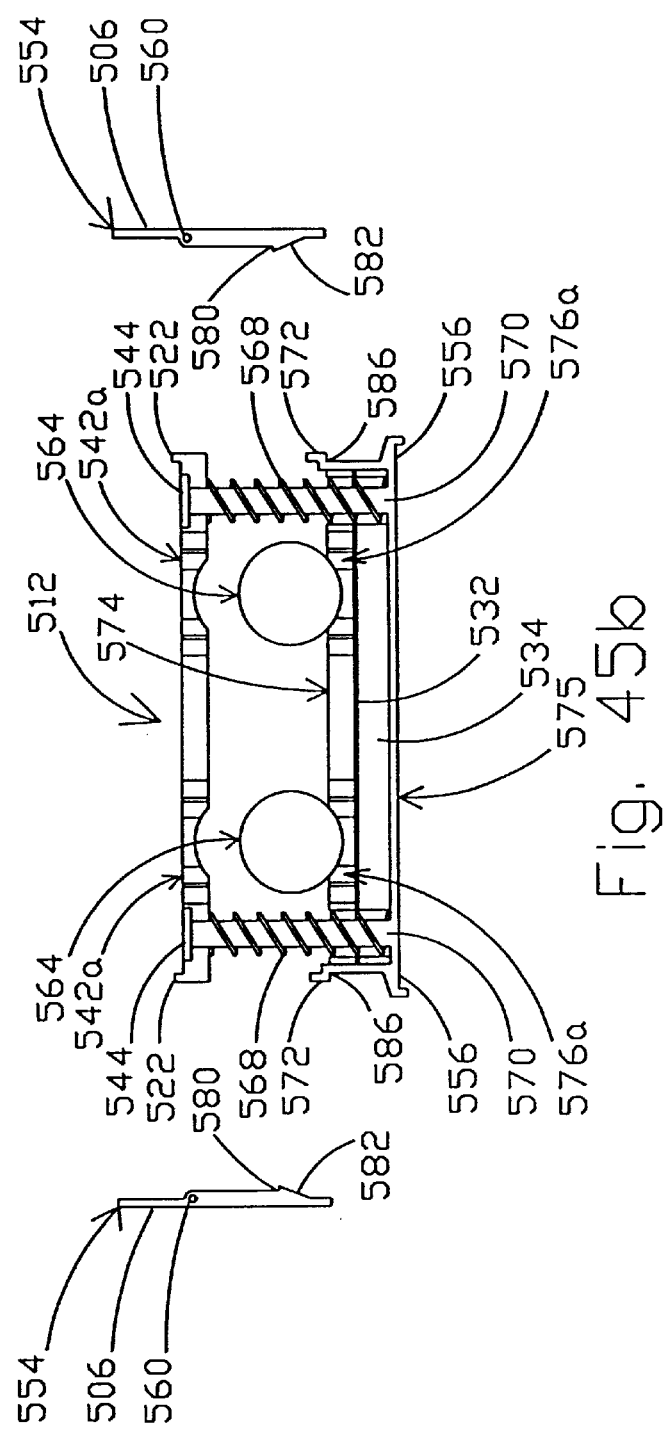

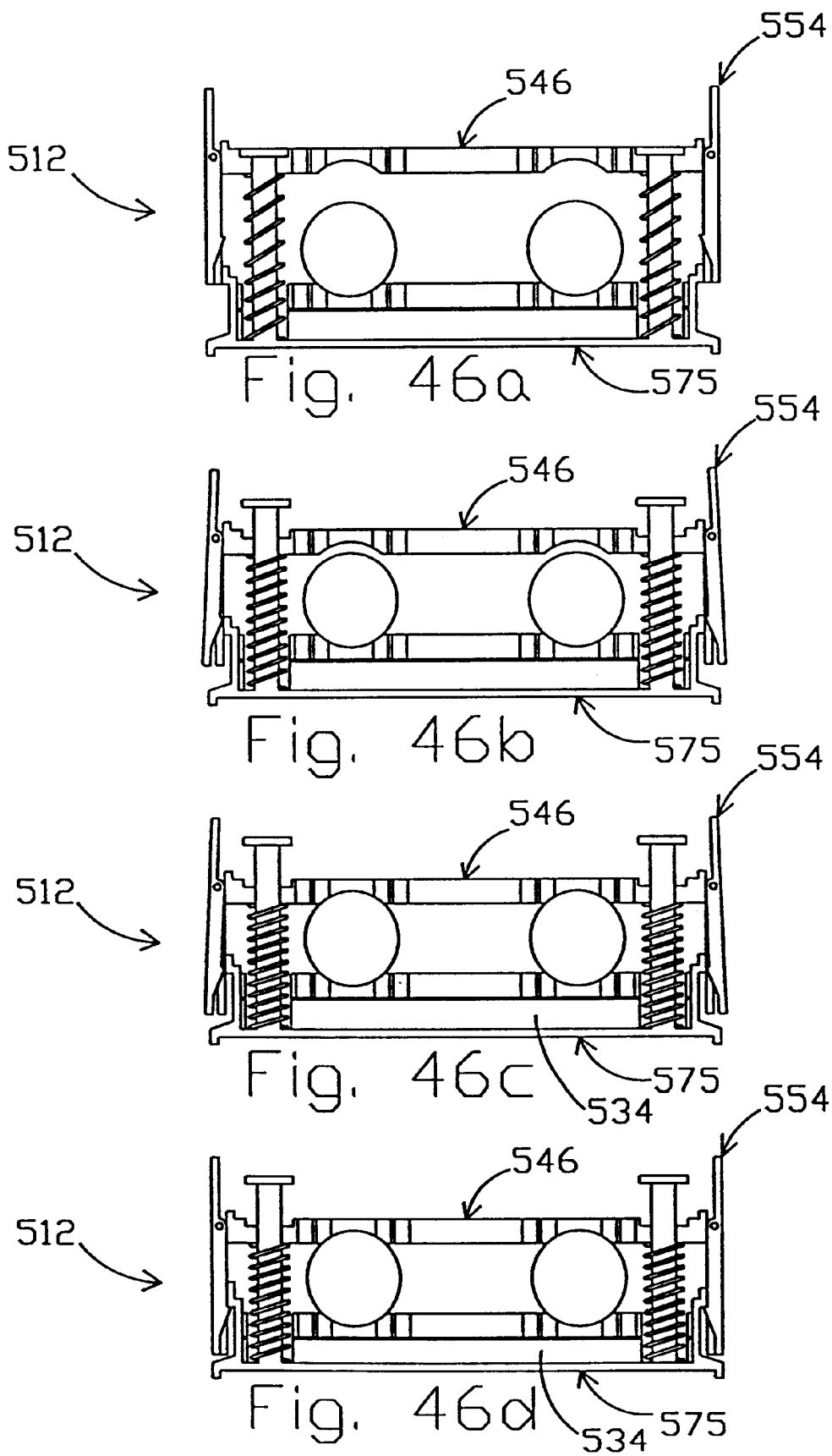

APPARATUS AND METHOD FOR TARGETING AND/OR INSTALLING FASTNERS INTO AN INTRAMEDULLARY NAILS

This application is a continuation of Ser. No. 09/190,033, filed Nov. 11, 1998, now U.S. Pat. No. 6,129,729.

BACKGROUND OF THE INVENTION

The present invention relates to positioner devices and, more specifically, to such devices for determining and maintaining or holding a specific position or target such as may be needed in orthopaedic surgery for the placement of locking Bone fractures, such as long bone fractures of the upper and lower extremities, may be stabilized with metal rods or so-called intramedullary nails that are implanted into the hollow center or so-called intramedullary canal of these bones. However, an implanted intramedullary nail may provide only limited stability to a fractured bone. That is, the two ends of the fractured bone may rotate, angulate and/or telescope on the implanted nail.

The intramedullary nails may achieve greater stability by the use of locking screws that may pass through the bone and the intramedullary nail. Such locking screws may be placed at opposite ends of the implanted intramedullary nail and may lock the parts or sides of the fractured bone to the implanted intramedullary nail. As a result, the locking screws may prevent the fractured bone from rotating, angulating and/or distracting upon the implanted intramedullary nail.

The region of the bone where the nail is implanted is identified as proximal and the opposite end of the intramedullary nail is distal. Intramedullary nails have two proximal and two distal screw holes. The locking screws should be placed precisely through both the bone and screw holes in the implanted intramedullary nail. Placement of the proximal transverse locking screws, near to the insertion point of the intramedullary nails may be relatively simple. However, placement of the two transverse locking screws across both the bone and distal end of the intramedullary nail may be relatively difficult.

A number of steps may be undertaken to successfully place locking screws across both a fractured bone and an implanted intramedullary nail. First, X-rays or the like may be used to locate the screw holes in the intramedullary nail. Second, screw holes may be drilled through the bone on either side of each screw hole. Third, the length of the locking screw needed to pass through both the bone and the intramedullary nail may be determined by passing a depth gauge or the like through the drilled holes and intramedullary nail. Fourth, the selected locking screw or screws are implanted, transfixing the bone and the intramedullary nail.

The above-described steps for placement of the proximal locking screws may be readily accomplished with a proximal based outrigger bushing that is attached to the proximal end of the implanted nail. Such outrigger bushing may provide rigid concentric alignment with the proximal screw holes so as to enable rapid and reliable drilling, measurement, and placement of the proximal screws. On the other hand, an outrigger bushing with a proximal origin for the distal screw holes may not perform satisfactorily due to the mechanical stress on the outrigger and/or the unpredictable distortion of the distal end of the intramedullary nail during implantation.

Distortion of the distal end of an intramedullary nail may occur as it is implanted into a bone. That is, the distal end of the nail may rotate, angulate and/or deflect within the intramedullary canal of the bone. Accordingly, a fixed proximal based outrigger bushing may not compensate for the actual position of the distal screw holes and may not function adequately.

An adjustable-type outrigger bushing may compensate for the distortion of the distal end of an implanted intramedullary nail. However, such adjustable-type outrigger bushing may require excessive tinkering to obtain correct alignment with the screw holes in the implanted nail. This tinkering may necessitate an increased use of X-rays and as such may increase undesirable X-ray exposure to the surgeon, patient and operating room staff, and may also lengthen the surgical procedure.

Outrigger bushings with a proximal origin for the distal screws may effectively have a long lever arm. Uncontrollable micromotion of such long lever arm may prevent the successful use of these devices. Even when an outrigger bushing, such as the adjustable-type outrigger bushing is eventually aligned with the distal screw holes, the alignment may not be sustained due to micromotion.

The combined mechanical difficulties of the proximal based outrigger and the distortion of the implanted nail have thwarted the successful development of a proximal based outrigger bushings for the distal screw holes.

To place distal locking screws in an implanted interlocking nail the location of the distal screw holes should be known. However, the distal end of the nail may be hidden from view within the intramedullary canal of the bone and visualization of the distal screw holes may require X-ray guidance provided by a portable adjustable X-ray machine or the like in the operating room. Such X-ray machine may be manipulated to a position in which the path of the x-ray beam is parallel with the long axis between a single set of screw holes in the intramedullary nail. When this alignment is accomplished, the X-ray appearance of the screw holes may be substantially perfect circles. The X-ray machine may be maintained in axial alignment with a distal screw hole throughout the previously-described second through fourth steps for placement of a distal interlocking screw.

The lack of success of proximal origin outrigger bushings for the distal locking screws has stimulated the development of a number of devices and techniques to accomplish the placement of these screws. However, although these devices may locate the distal screw holes and facilitate the drilling of holes in bone, these devices may not provide guidance which may be needed for the steps of measuring the length of the locking screw and/or placing the locking screw across the bone and intramedullary nail. The steps of measuring the optimum length of the locking screw and placing the selected screw may be very difficult to achieve. The successful drilling of a screw hole across the bone and intramedullary nail may not facilitate the necessary and technically difficult steps of measuring or implanting the locking screw.

There is a substantial amount of empty space concentrically surrounding the implanted intramedullary nail. The drilled screw hole in the bone may not be of sufficient length or thickness to serve as a bushing to align the depth gauge or locking screw with the screw hole in the interlocking nail. The depth gauge and locking screw will frequently miss the screw hole and deflect off the intramedullary nail. Therefore, measuring the length of the locking screw and the implantation of the measured locking screw may necessitate the use of additional X-rays and, as such, may result in excessive x-ray exposure to the surgeons, patient and/or operative team and may substantially lengthen the surgical procedure regardless of whether the drilling of the screw hole(s) across the bone and intramedullary nail was successful.

OBJECTS AND SUMMARY OF THE INVENTION

An object of the present invention is to provide an apparatus and method for targeting and/or installing screws into an intramedullary nail which enables distal locking screws to be accurately, rapidly and reliably placed in the intramedullary nail.

Another object of the present invention is to provide an apparatus as aforesaid which is relatively simple to assemble and use. Such assembly and/or use may utilize skills which a surgeon already possesses or is familiar with and may utilize equipment already present in an operating room.

The present apparatus and method may simplify the steps of drilling, measuring and placing of the distal locking screws, thereby substantially shortening the amount of time required to properly insert the distal locking screws. Further, the present apparatus may enable such proper insertion of the distal locking screws with a reduced or lesser use of X-rays as compared to other techniques. Thus, the present apparatus and method may shorten operating room time and minimize x-ray exposure to the surgeon, operating staff and/or patient.

In a preferred embodiment, the present apparatus has five major components. Such components may be fabricated predominantly from a significantly radiolucent plastic material. The five major components can rapidly be assembled by the surgeon. These components include a foundation which is attached to the patient, a locking-targeting-guide supported by the foundation, a handle attached to the locking-targeting-guide which may be used to position the locking-targeting-guide over the distal screw holes of the implanted intramedullary nail, and a set of two interchangeable inserts which are inserted into the locking-targeting-guide. The first of such inserts may be used to "target" or align a portion of the locking-targeting-guide with the distal screw hole and the second of such insert may be used to guide a drill, drill bit, depth gauge, screwdriver and other such devices which may be utilized in the installation of the distal screw.

Other objects, features and advantages according to the is present invention will become apparent from the following detailed description of the illustrated embodiments when read in conjunction with the accompanying drawings in which corresponding components are identified by the same reference numerals.

BRIEF DESCRIPTION OF THE DRAWINGS

FIG. 7 is a diagram of the targeting insert of FIG. 1;

FIG. 8 is a diagram of the cannulated insert of FIG. 8;

FIG. 9 is a section diagram of the cannulated insert of FIG. 8;

FIG. 35 is an isometric diagram of the handle of FIG. 34;

FIG. 36 is an isometric diagram of a lock release reset mechanism of the handle of FIG. 35;

FIG. 37 is an isometric exploded diagram of the handle of FIG. 34;

FIG. 38a is a diagram of the handle of FIG. 34 illustrating a position of a handle-trigger when it is inserted into the locking-targeting-guide;

FIG. 38b is a diagram of the handle of FIG. 34 illustrating the position of the handle-trigger when it has been compressed and locked into the locking-targeting-guide;

FIG. 38c is a diagram of the handle of FIG. 34 illustrating the position of the handle-trigger when it has been completely compressed deploying a probe into the locking-targeting-guide and releasing the lock mechanism;

FIGS. 44a and 44b are diagrams of the handle of FIG. 40;

FIG. 45a is a cross-sectional diagram of the locking-targeting-guide of FIG. 40 when it is not engaged to the handle of FIG. 40;

FIG. 45b is a partially exploded cross-section of the locking-targeting-guide of FIG. 40;

FIG. 46a is a diagram of the locking-targeting-guide of FIG. 40 in which the handle is not engaged;

FIG. 46b is a diagram of the engaged locking-targeting-guide and handle of FIG. 41 in which the handle latch and lock/release controller are engaged;

FIG. 46c is a diagram of the engaged locking-targeting-guide and handle of FIG. 41 in which the handle is fully compressed;

FIG. 46d is a diagram of the locking-targeting-guide of FIG. 41 in which compression of the handle has activated a locking mechanism of the locking-targeting-guide;

DETAILED DESCRIPTION OF THE PREFERRED EMBODIMENTS

Figure 1:
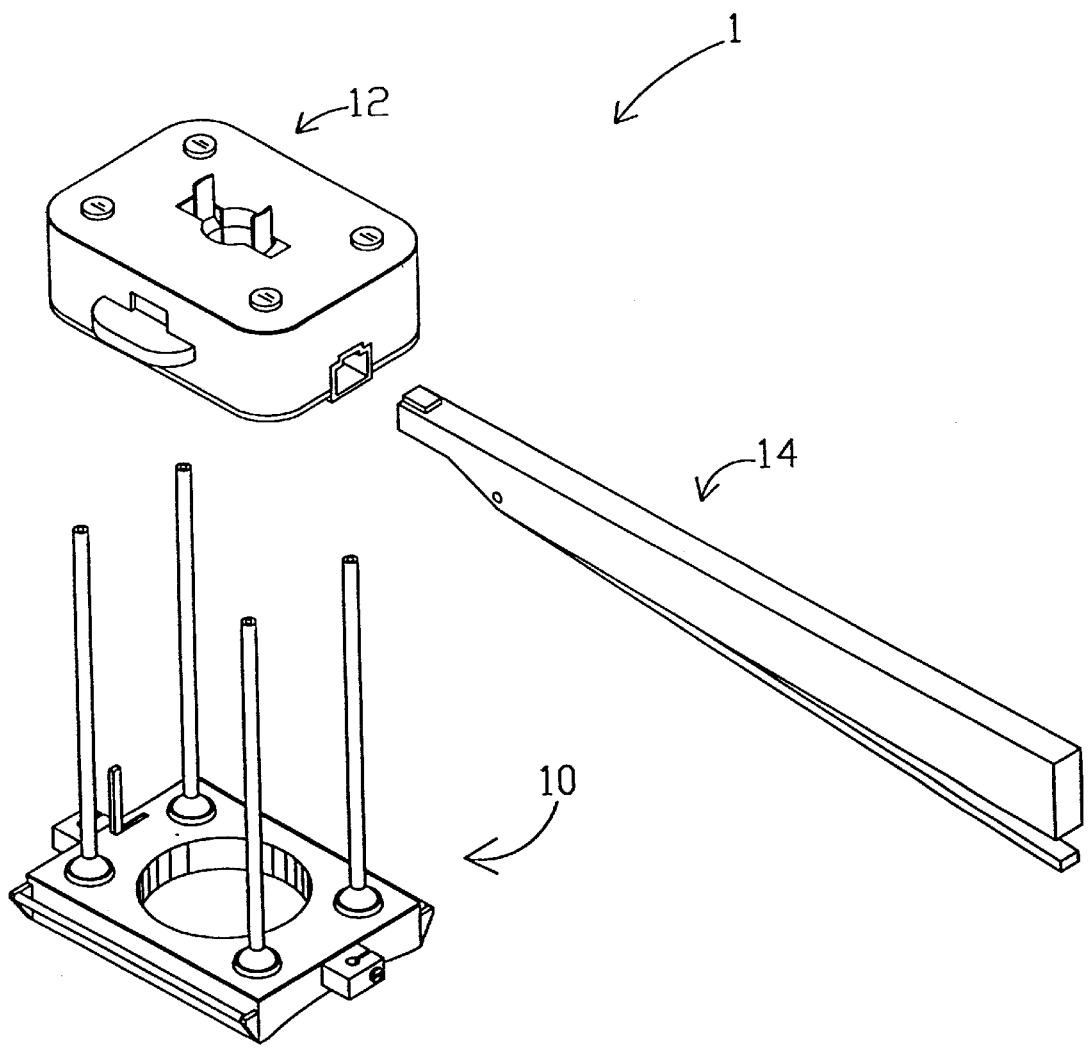
FIG. 1 is a diagram of three basic components of an apparatus for targeting and/or installing screws into an intramedullary nail according to an embodiment of the present invention.
Figure 4:
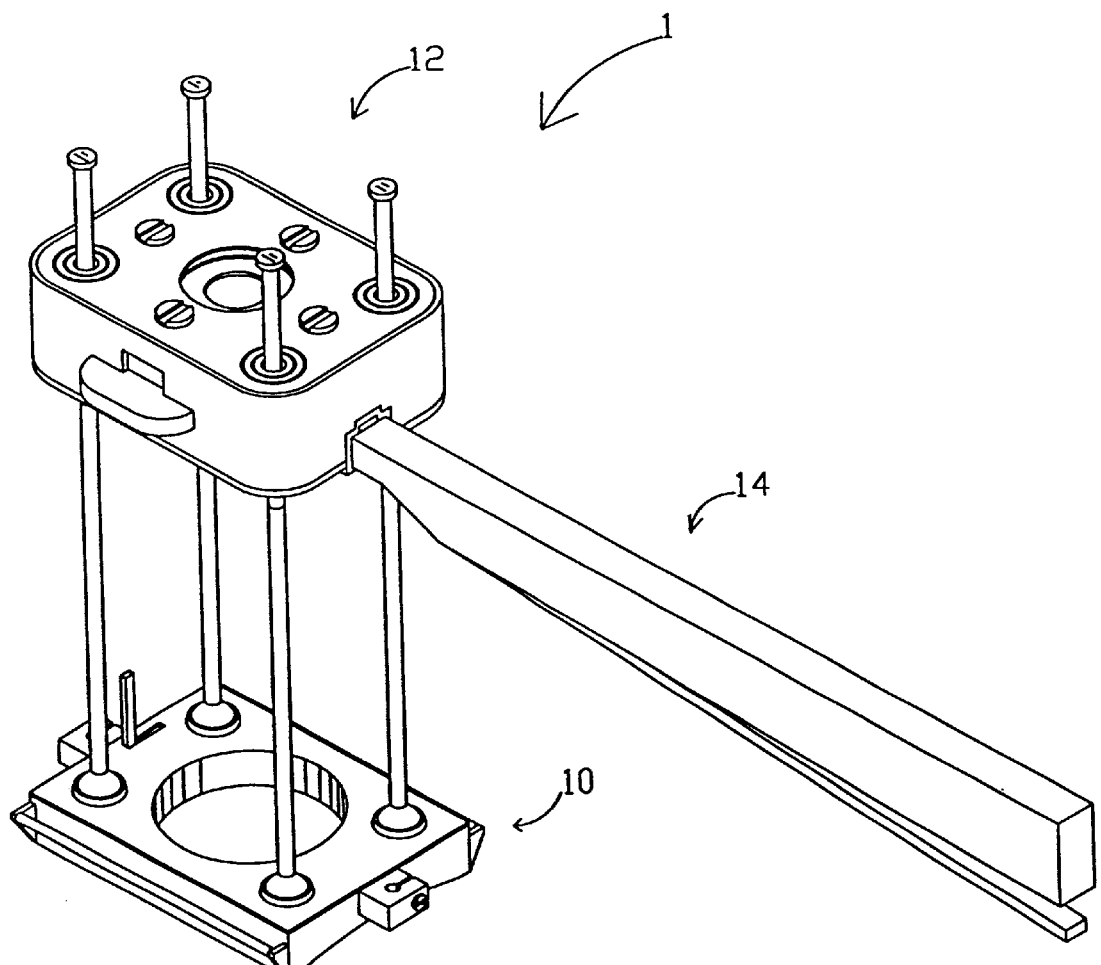
FIG. 4 is a diagram of the apparatus of FIG. 1.
Figure 5:
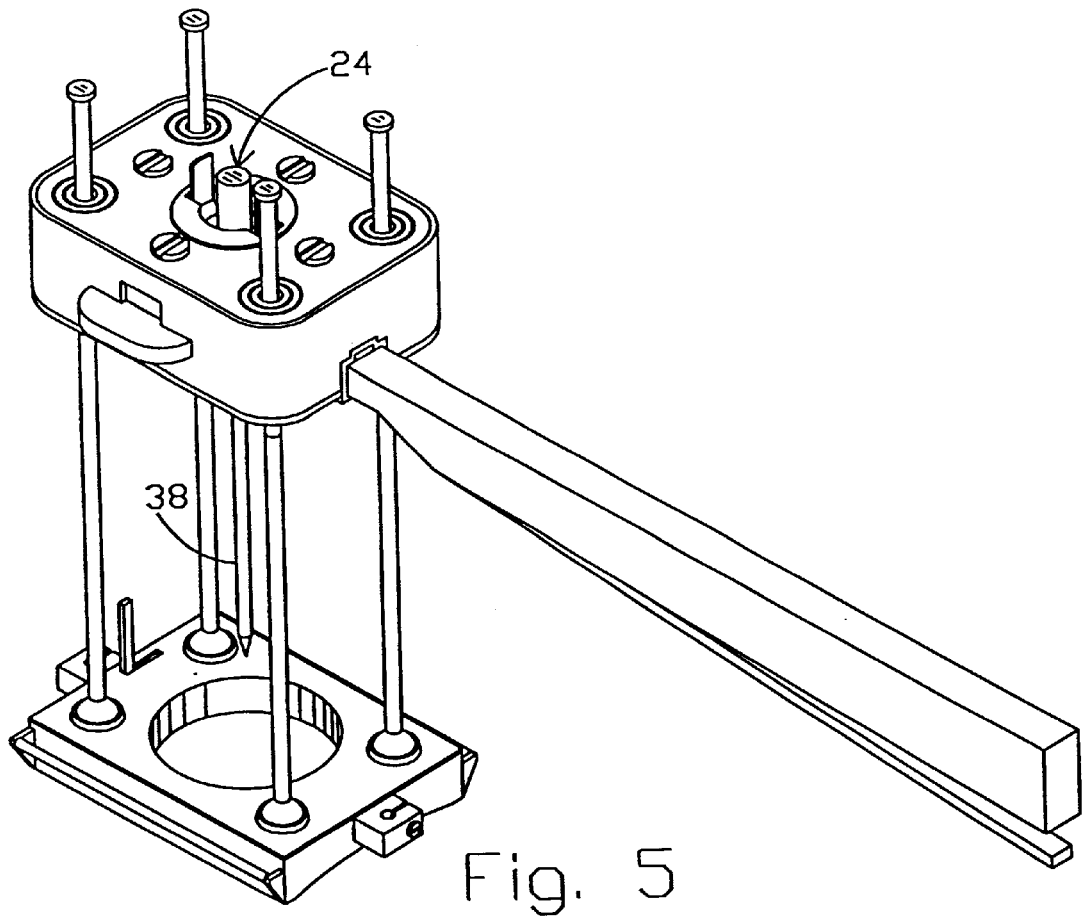
FIG. 5 is a diagram of the apparatus of FIG. 4 with a targeting insert.

An apparatus for targeting and/or installing screws into an intramedullary nail according to an embodiment of the present invention is illustrated in FIGS. 1 and 4. As shown therein, such apparatus 1 generally includes a foundation 10, a locking-targeting-guide 12, and a handle 14. The foundation 10 may be attached to a patient and may support the locking-targeting-guide 12. The locking-targeting-guide 12 may be moved to a desired position or alignment when supported by the foundation and may lock onto the foundation by use of a locking mechanism when the desired alignment is obtained. The handle 14, which may be detachably coupled to the locking-targeting-guide 12, serves to position the locking-targeting-guide and trigger the locking mechanism within the locking-targeting-guide 12 when the desired alignment is achieved.

Figure 6A:
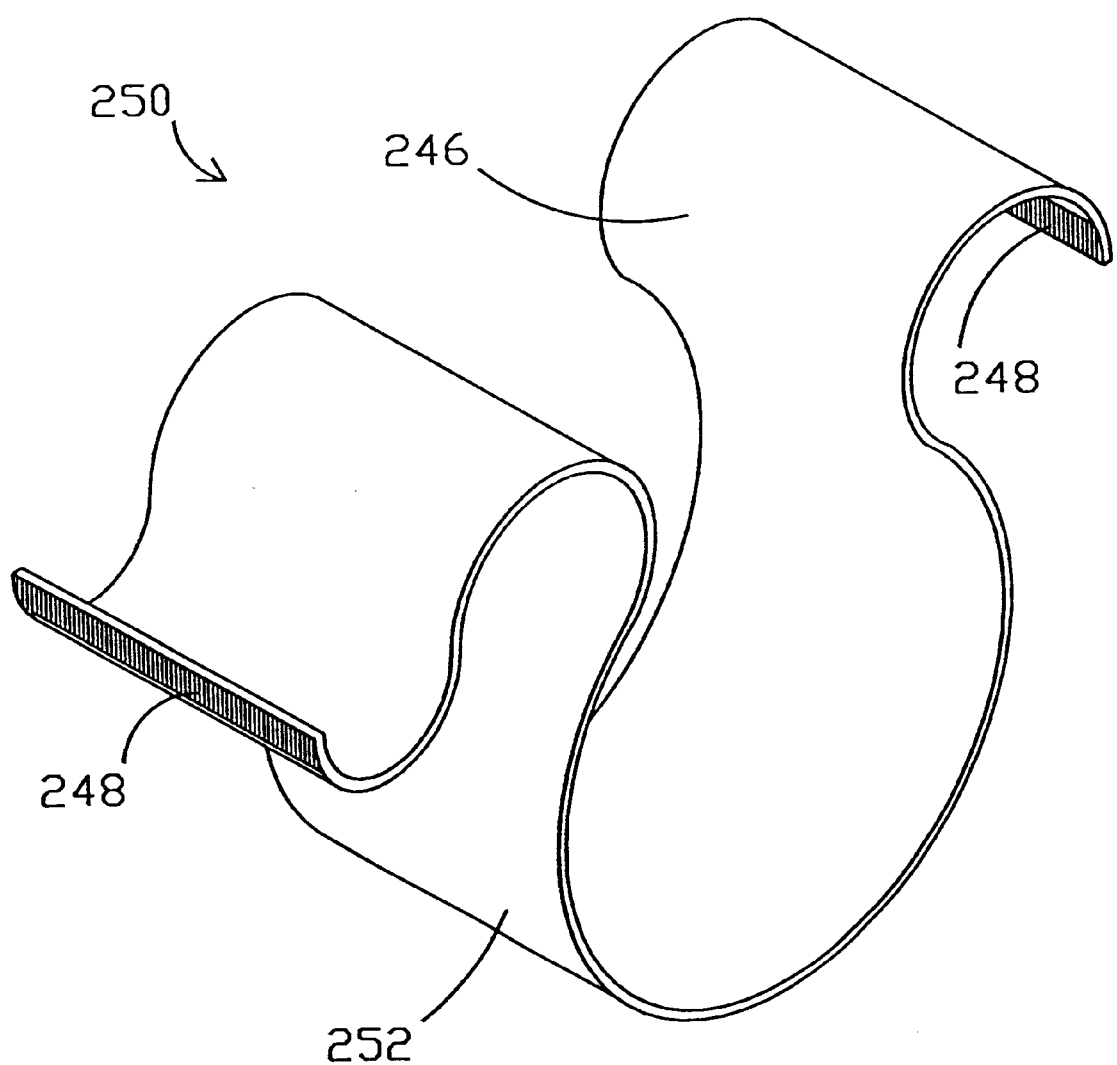
FIG. 6a is an isometric view of a neoprene fixation strap.
Figure 6B:
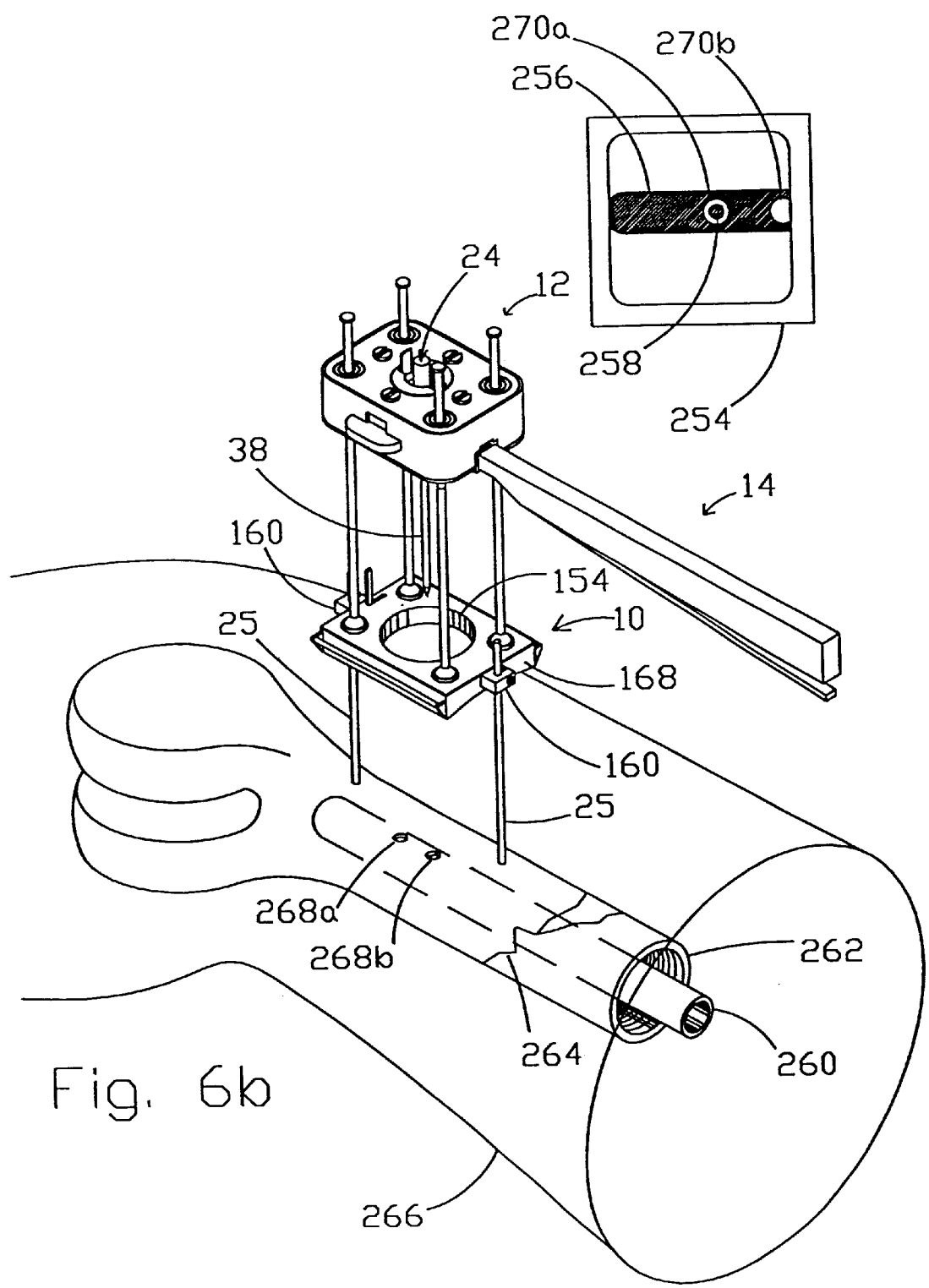
FIG. 6b is an isometric view of the present apparatus of FIG. 1 attached to a broken femoral bone by metal fixation pins.

With reference to FIGS. 6A and 6B, apparatus 1 is used after an intramedullary nail 260 has been implanted into a fractured femur 262, stabilizing the fracture 264. X-rays emitted from an X-ray machine have been aligned with a respective distal screw hole or holes 268a or 268b. The position of the screw hole(s) are noted and a line is drawn on the skin over the screw hole(s). Such line provides a relative guide mark for positioning the foundation 10 on the patient.

The implanted intramedullary nail 260 is visualized on an X-ray monitor 254 as a radio-opaque black bar 256. The two screw holes 268a and 268b are seen on the X-ray monitor 254 as two circles 270a and 270b. When an alignment spike 38 (which may be fabricated from a metal material) of a targeting insert 24 is aligned over the hole 268a, the spike 38 is seen as a radio-opaque black circle centered within the X-ray image 270a of screw hole 268a.

The foundation 10 has a relatively large central fenestration 154 which is centered over the lines or marks drawn on the patient. A foundation frame 168 of foundation 10 can be fixed on the skin over the distal screw holes of the implanted intramedullary nail by strapping it in place with a wide elastic neoprene band 250. The outer surface of the neoprene band 250 may have a Velco knapped surface 252 and may have Velcro hook attachments 248 at the terminal ends of the outer surface. The inner surface 246 of the neoprene band may be smooth. The foundation 10 may be strapped in place with other types of elastic devices or the like. Alternatively, the foundation can be held in place by use of a number of metal fixation pins 25 that are each placed or drilled through a fenestration 164 (FIG. 28) of a clamp 160 in the foundation 10 into the underlying bone. In this later situation, after the fixation pin or pins 25 have been drilled into the bone, the clamp or clamps 160 are tightened so as to rigidly hold the fixation pin or pins 25. As a result, the foundation 10 is held to the underlying bone.

In a relatively thin individual or patient; the elastic neoprene strap 250 alone may provide a stable attachment of the foundation 10 to the limb. In a larger patient or one with more fat, a number of fixation pins 25 may be needed to provide a stable attachment between the foundation 10 and the underlying bone. Alternatively, the elastic neoprene strap and fixation pins 25 can also be used together for optimum attachment between the foundation 10 and the limb and underlying bone.

With reference to FIGS. 28–32, the foundation 10 has a plurality of vertical alignment rods 146 that are releasably rigidly held normal to a surface of a frame 170 of the foundation 10. The plurality of alignment rods 146 are basically positioned at the corners of the frame 170 and are arranged such that the ends of the vertical alignment rods are seated in spherical bases 150 which, in turn, are arranged or restrained in sockets 174 of a socket frame 172 by restraining collars 152 so as to create respective ball joints.

Each of the spherical bases 150 has a flat bottom surface 175 which is in contact with a flexible restraining plate 180 within the foundation 10. Each of the vertical alignment rods 146 may be held in a vertical position by pressure of the restraining plate 180 against the flat bottom 175 of the respective spherical base 150.

A freedom lever 158 in the foundation can lower the restraining plates 180 away from the spherical bases 150. The same freedom lever 158 can also be used to raise the flexible restraining plates 180 against the spherical bases 150.

Simple manipulation of the alignment rods can bring the flat surfaces of the spherical bases 175 into proper contact with the raised restraining plates 180. Such manipulation or maneuver may realign, if necessary, the vertical alignment rod or rods 146 into a rigid vertical position. When the restraining plates 180 are lowered away from the spherical bases 150, the vertical alignment rods 146 can freely rotate through a relatively large spherical like arc.

On opposite sides of the frame 170 of the foundation 10 are bars 166 over which the neoprene strap 250 can be passed to fix the foundation to the injured limb.

The foundation 10 has a plurality of pivotable clamps 160 to accept fixation pins 25. Each of the fixation pins 25 may be held in a respective clamp 160 by tightening a screw 162. The clamps 160 can pivot to enable proper positioning of the fixation pins 25 into the underlying bone. In addition to holding the fixation pin, tightening the screw 162 will also prevent rotation of the clamp 160.

The freedom lever 158 is pivotally coupled to the foundation 10 at 186a and a conjoined lock/release ring 176. Moving the freedom lever 158 lifts and lowers the conjoined lock/release ring 176 which brings the restraining plates 180 in contact with or moves them away from the spherical bases 150 of the vertical alignment rods 146.

The conjoined lock/release ring 176 is pivotally coupled to the foundation lo by a plurality of pivot bars 184. Such pivot bars 184 are attached to the foundation at 186a, 186b, 186c, 186d and attached to the conjoined lock/release ring 176 at pivot recesses 188.

The freedom lever 158 is arranged so as to move within an oblique slot 156 on the surface of the foundation. The long axis of the slot 156 may not be parallel to the plane of rotation of the freedom lever 158. Rotation of the freedom lever 158 in slot 156 may cause the freedom lever to experience a spring deformation slightly toward the center of the foundation 10. At an end of the slot 156 is a recess 157 that is in parallel alignment with the rotation plane of the freedom lever 158. When the freedom lever 158 reaches the recess 157 the spring deformation produced by the oblique orientation of the slot 156 is released. Upon such movement, the freedom lever 158 will snap into the recess 157.

When the freedom lever 158 is placed in a vertical position in the slot 156, which lifts the conjoined lock/release ring 176, it may contact a tension post 182 slightly before it is fully vertical. The freedom lever 158 may experience a slight spring deformation against the tension post 182 when it is completely vertical. Such spring deformation may hold the freedom lever 158 in the recess 157.

Figure 33:
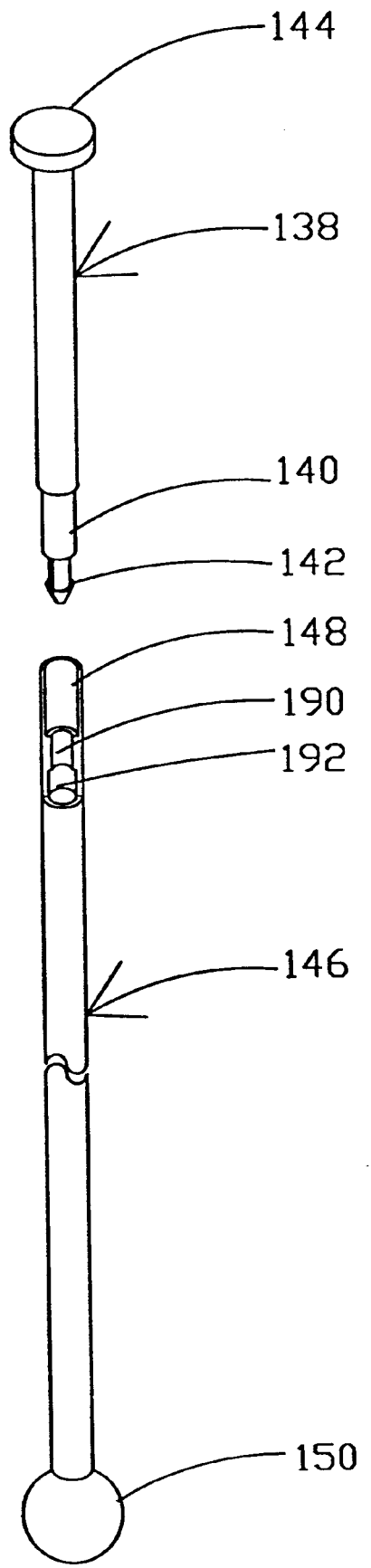
FIG. 33 is an isometric diagram of upper and lower vertical alignment rod segments.

With reference to FIG. 33, each vertical alignment rod 146 may have coupled thereto a corresponding upper alignment rod segment 138, which may be shorter in length than the vertical alignment rod. Unlike the alignment rod 146 which rises from spherical base 150 held in the foundation 10, the upper vertical alignment rod segment 138 is contained within the locking-targeting-guide 12.

At an upper end of the lower alignment rod segment 146 there is a receptacle 148 to receive the tines of a snap/lock 142 extending from the bottom of the upper alignment rod segment 138. The snap/lock tines 142 may be compressed together when passed through a cylindrical recess 190 and may re-expand in a recess 192, whereupon the snap/lock tines may be locked in place.

Figure 28:
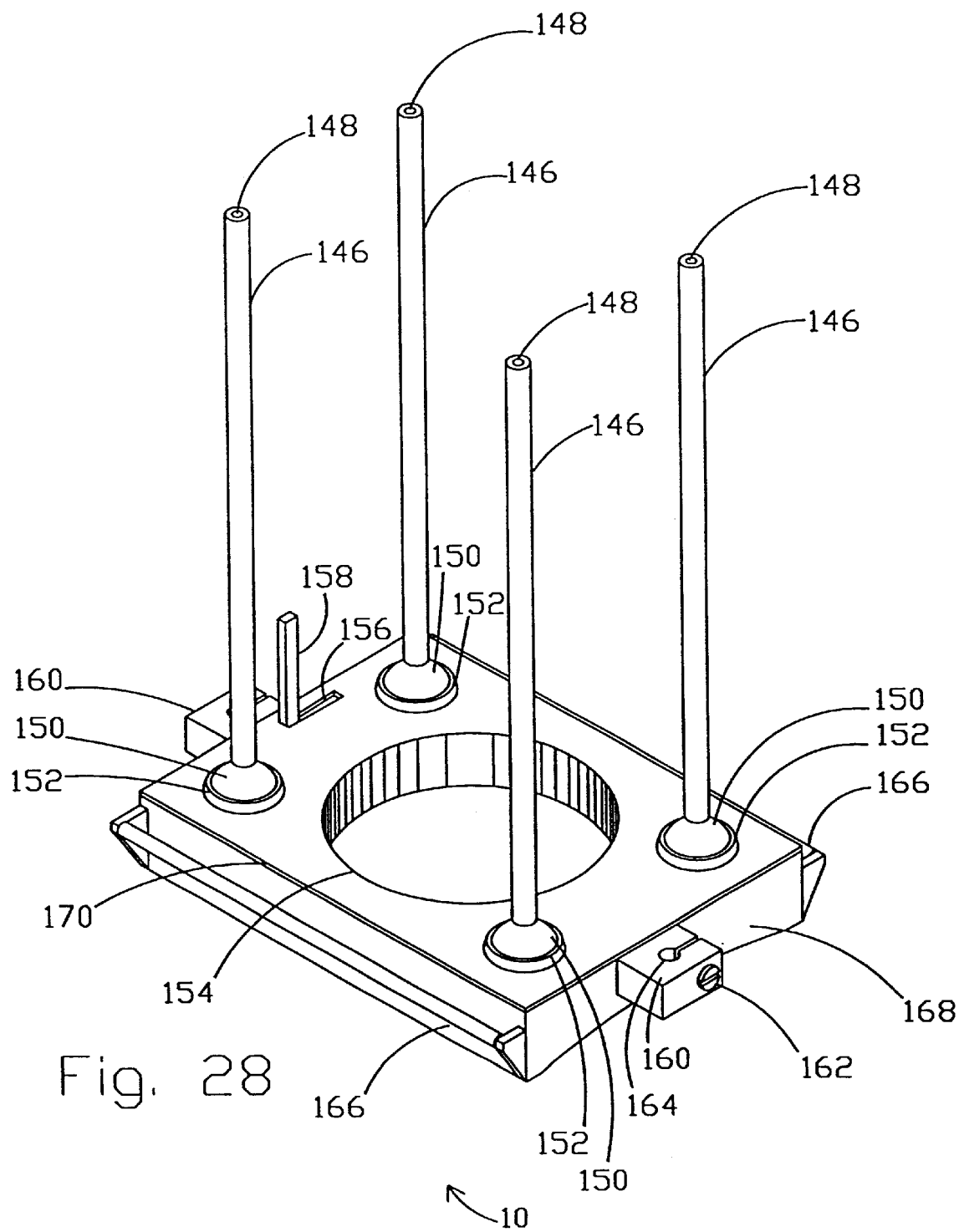
FIG. 28 is an isometric diagram of a foundation of the apparatus of FIG. 1.
Figure 29:
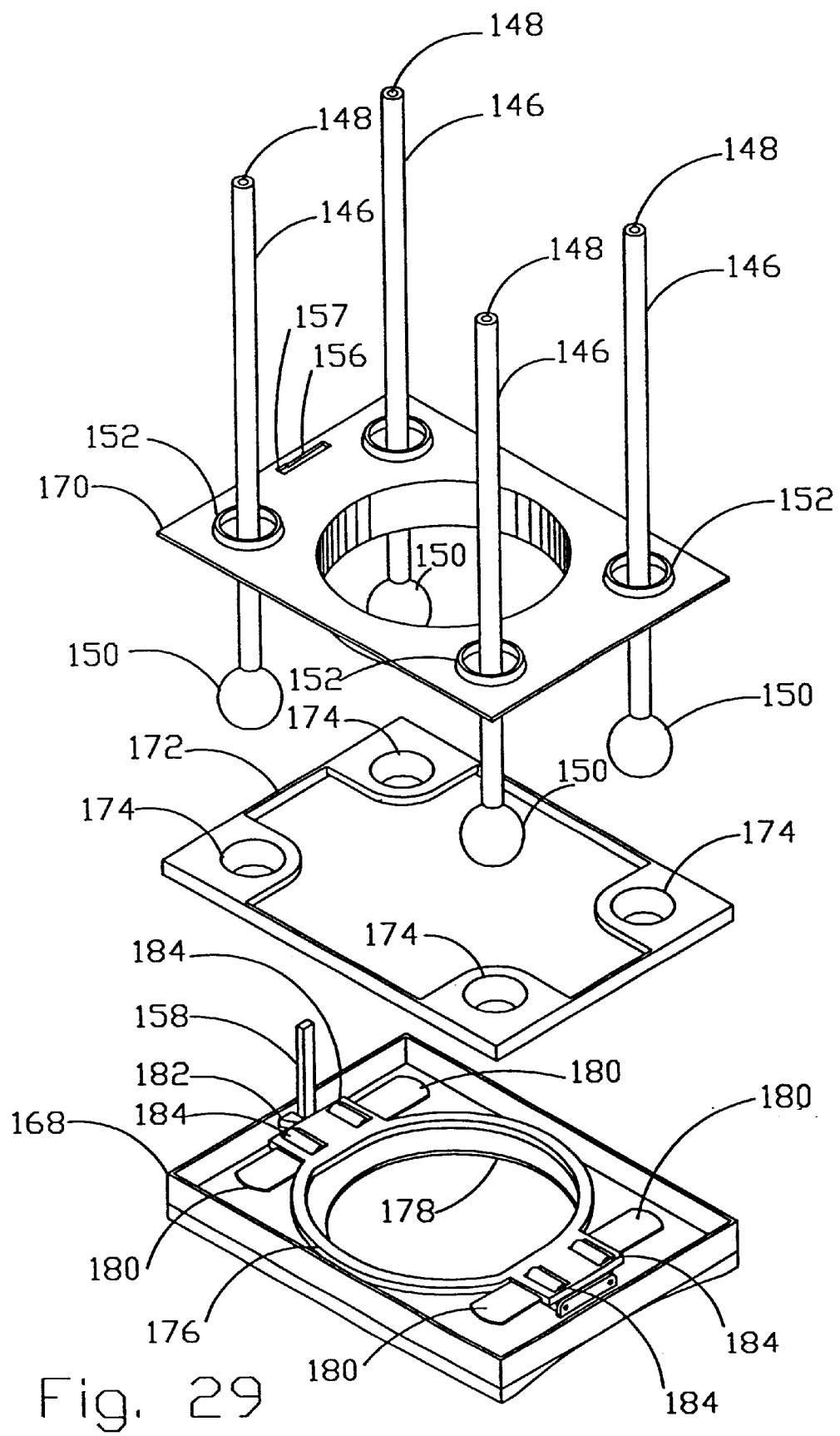
FIG. 29 is an exploded isometric diagram of the foundation of FIG. 28.
Figure 30:
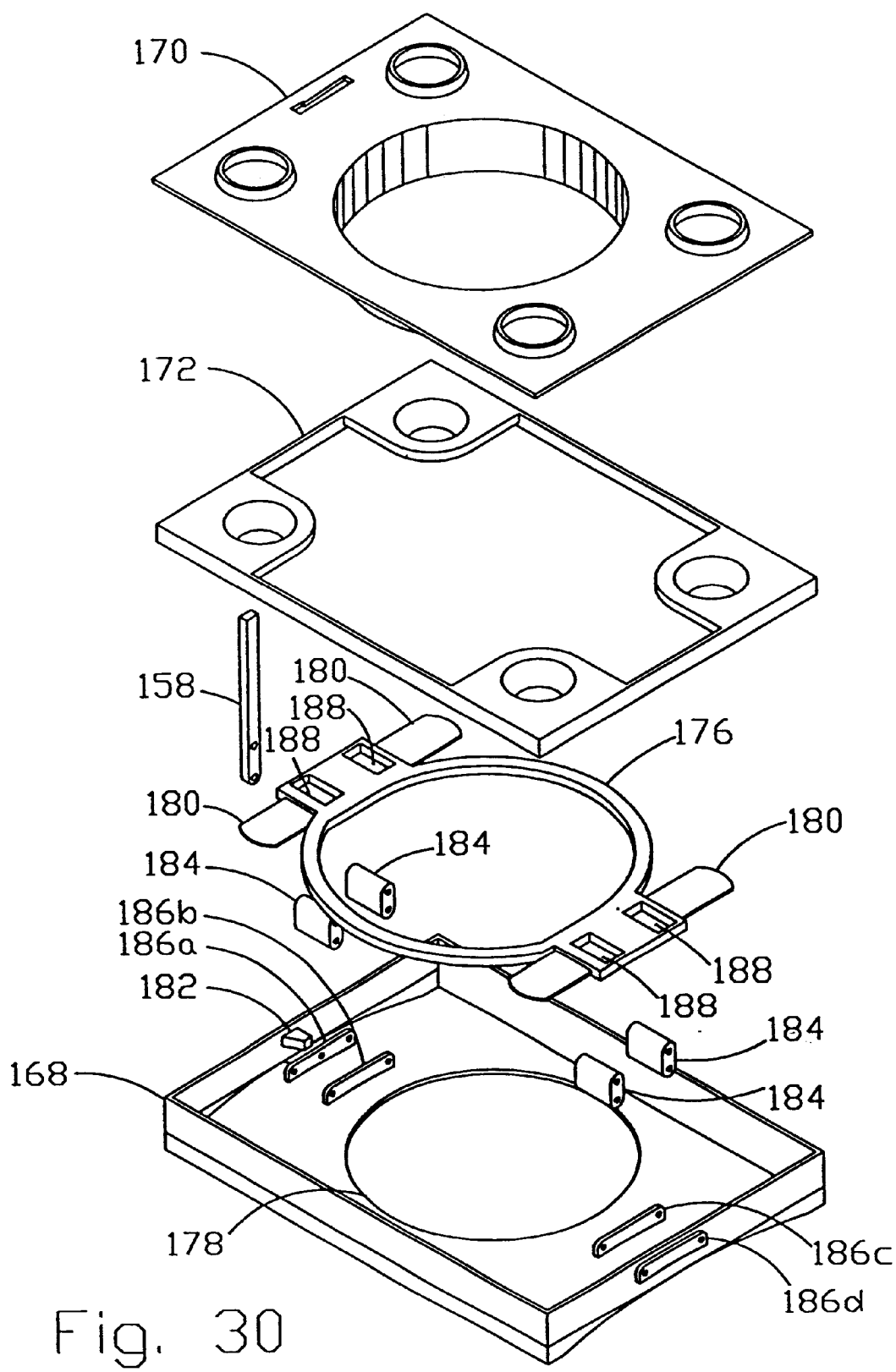
FIG. 30 is a partial exploded isometric diagram of the foundation of FIG. 28 which shows a lock release mechanism.
Figure 31:
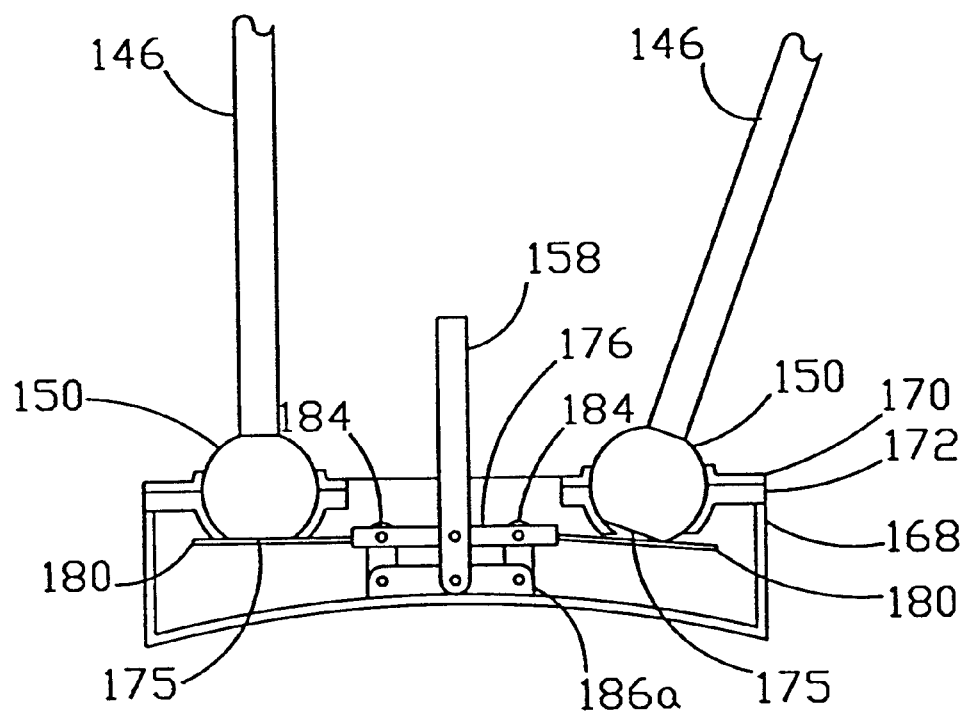
FIG. 31 is a diagram of the lock release mechanism of the foundation of FIG. 30 wherein lower vertical alignment rods are erect.
Figure 32:
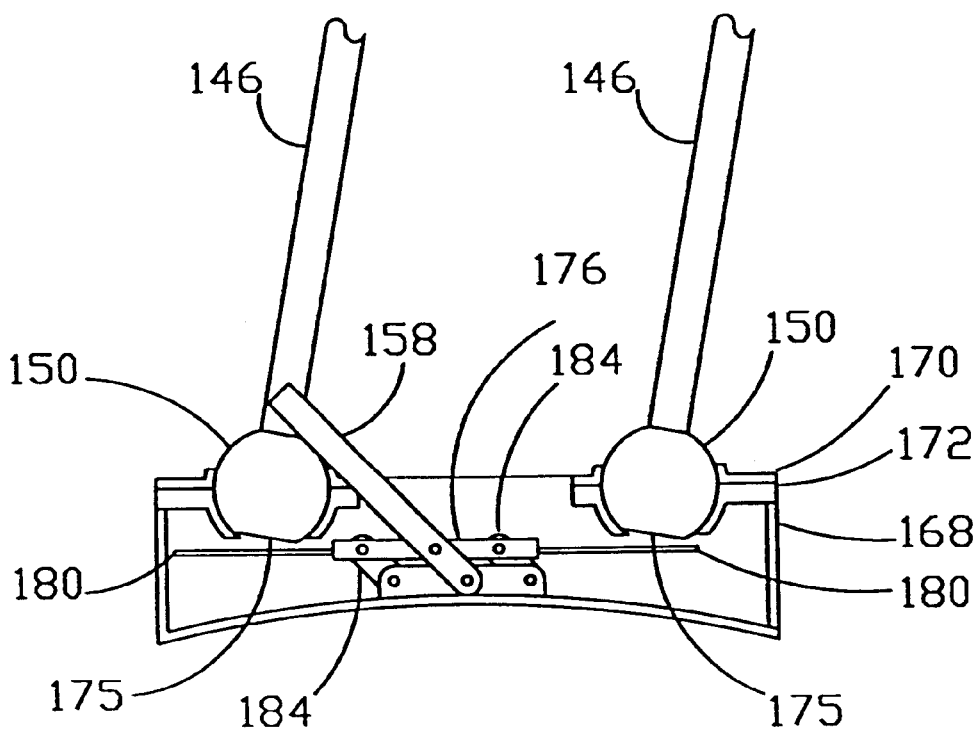
FIG. 32 is a diagram of the lock release mechanism of the foundation of FIG. 30 wherein the lock has been lowered and the vertical alignment rods are able to move.

With reference to FIGS. 1, 28, and 29, the lower vertical alignment rod segments 146 should be held in a vertically normal position to facilitate the attachment of the upper alignment rod segments 138 thereto. That is, if each lower alignment rod segment 146 were free to independently move such attachment of rod segment 138 would be exceedingly difficult. Spherical base restraining plates 180 help to ensure that the vertical alignment rods are kept vertical.

Figure 24:
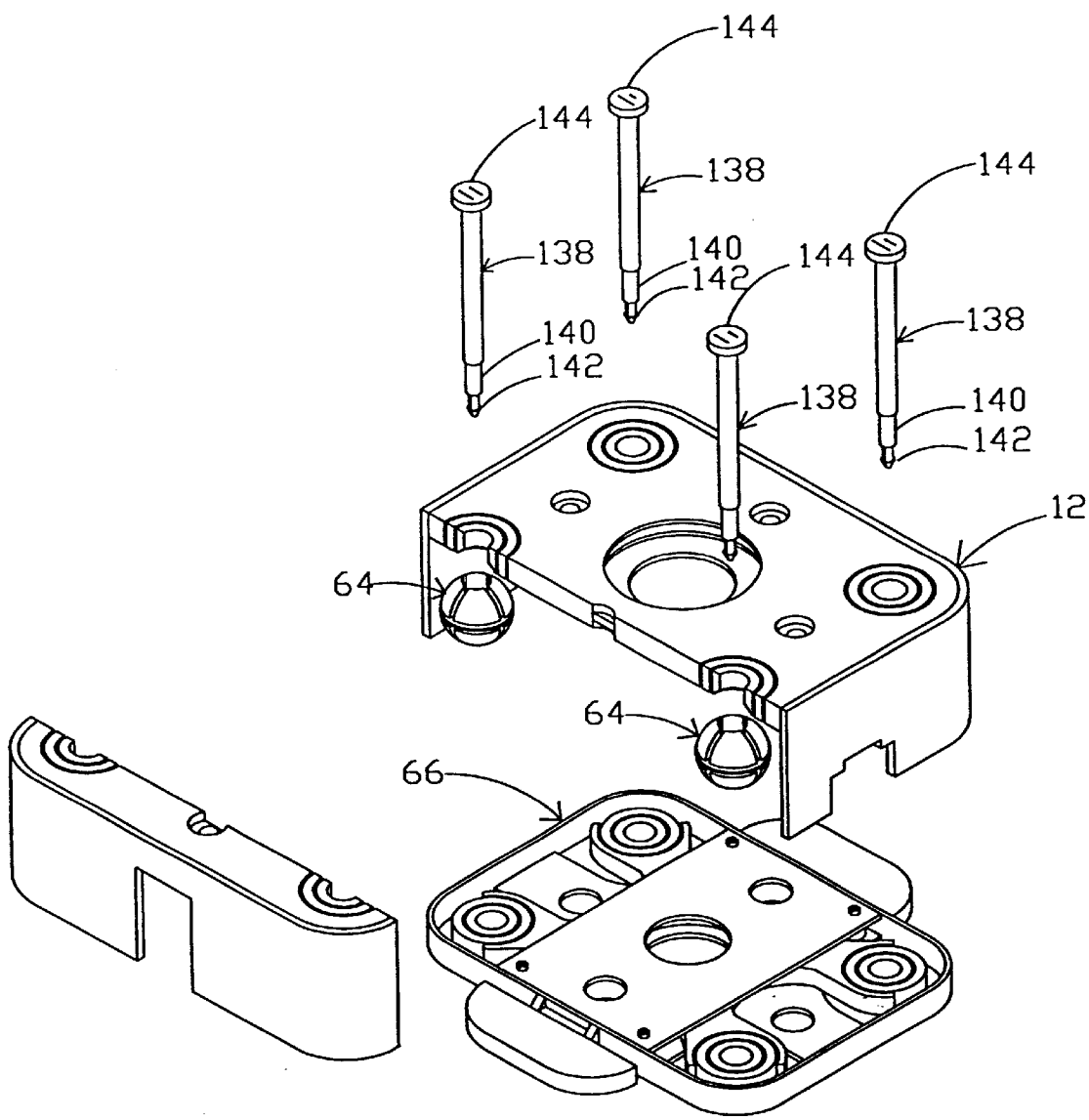
FIG. 24 is a partial isometric exploded diagram of the locking-targeting-guide of FIG. 10.
Figure 25:
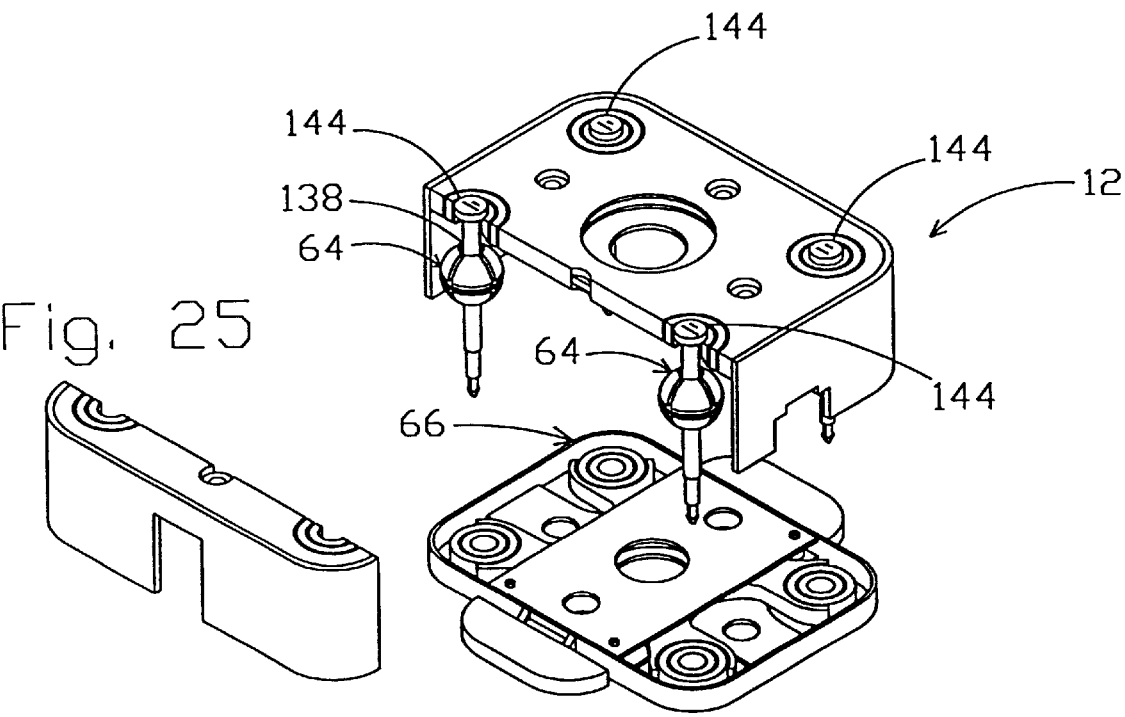
FIG. 25 is another partial isometric exploded diagram of the locking-targeting-guide of FIG. 10 which shows upper vertical alignment rod segments passing through upper universal joints and brake bearings.
Figure 26:
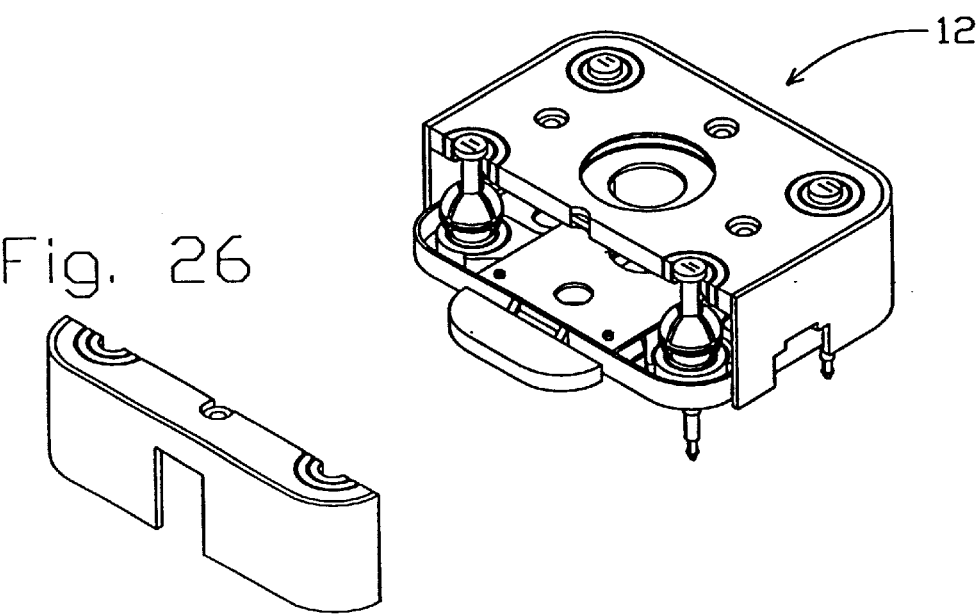
FIG. 26 is another partial isometric exploded diagram of the locking-targeting-guide of FIG. 10 which shows upper vertical alignment rod segments passing through upper universal joints, brake bearings, and lower universal joints.

With reference to FIGS. 24 and 25, the upper alignment rod segments 138 are restrained in the locking-targeting-guide 12. Each upper alignment rod segment 138 has a wide flattened cap 144 on one end thereof that rests on the top surface of the locking-targeting-guide 12 and prevents the upper alignment rod segment 138 from falling therethrough. The opposite end of each upper segment has a reduced diameter shaft 140 and snap/lock tines 142. The reduced diameter shaft 140 and the snap/lock tines enter into the receptacles 148 in the top of the lower alignment rod segments 146 (FIG. 33). The snap/lock tines 142 from the upper alignment rod segments 138 protrude from the lower surface of the locking-targeting-guide 12.

Figure 2:
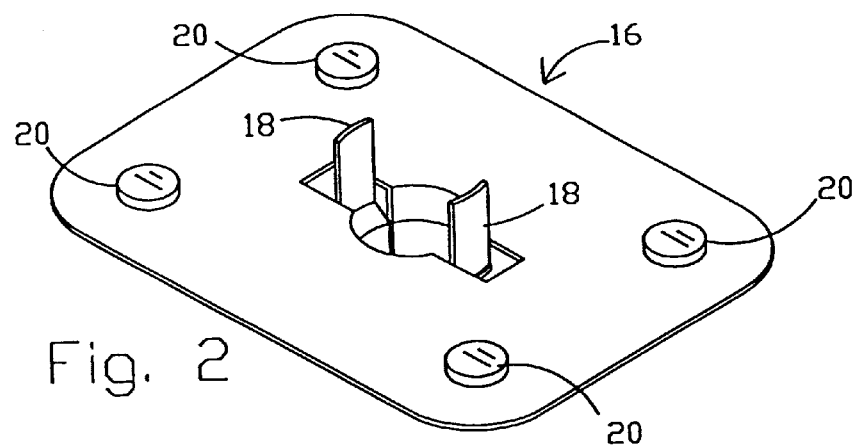
FIG. 2 is a diagram of an alignment rod restraining plate.
Figure 3:
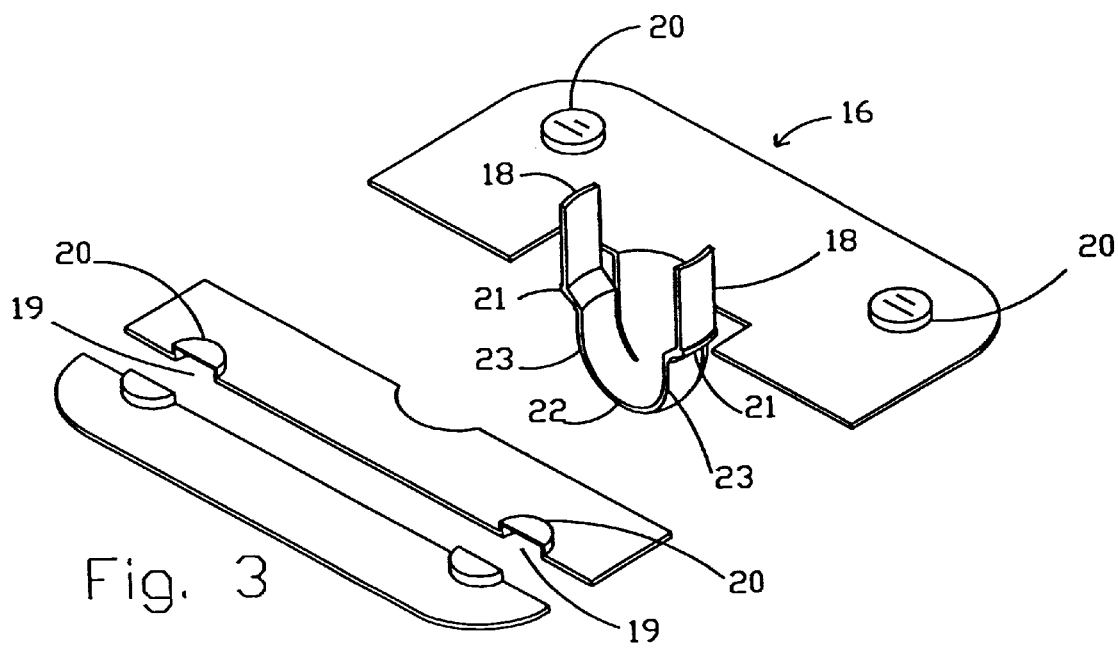
FIG. 3 is a diagram of a restraining plate locking and release mechanism of an alignment rod restraining plate of FIG. 1.
Figure 27:
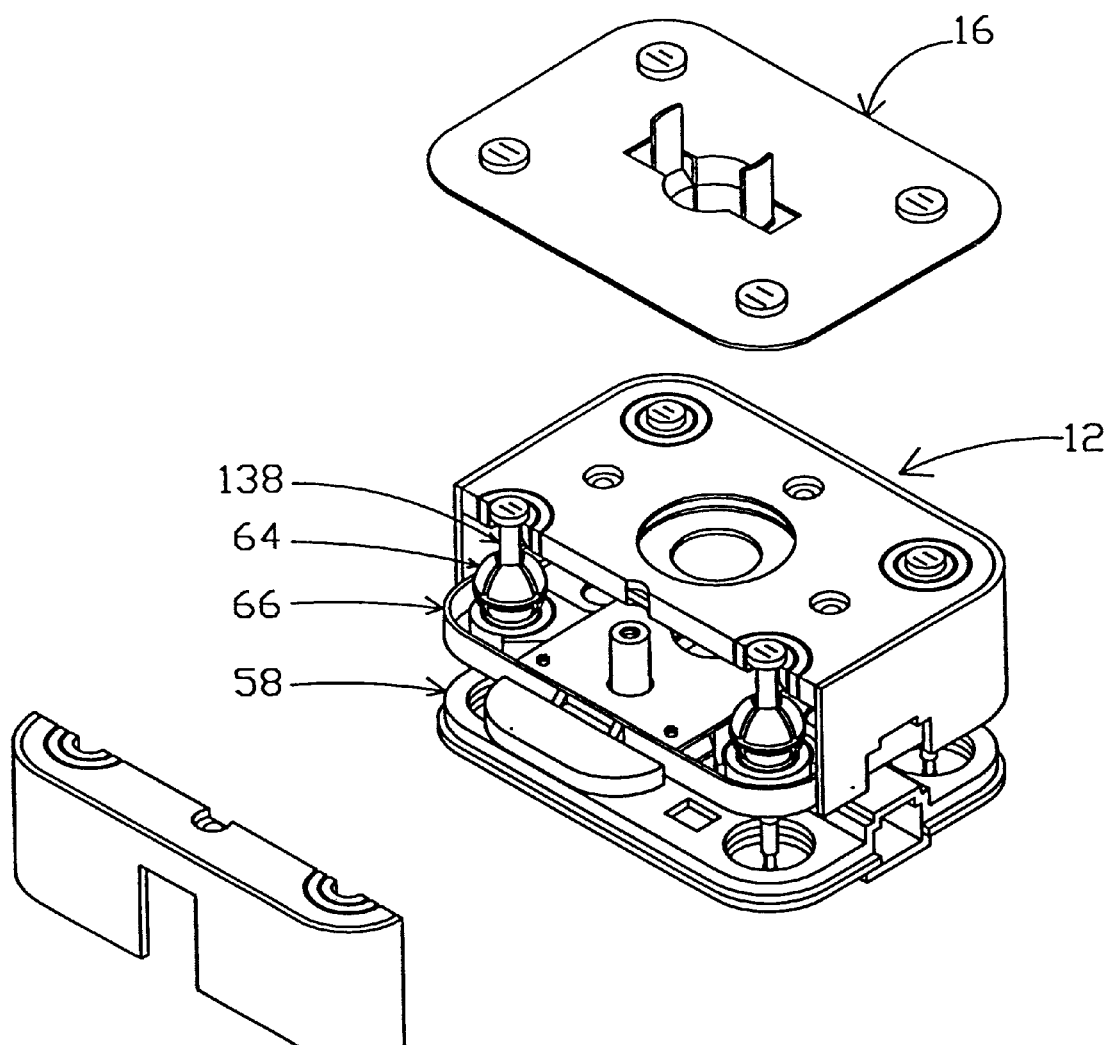
FIG. 27 is a diagram of the locking-targeting-guide of FIG. 10 and a vertical alignment rod restraining plate which shows upper vertical alignment rod segments passing through upper universal joints, brake bearings, lower universal joints and a base component.

With reference to FIGS. 2, 3 and 27, an alignment rod restraining plate 16 is snapped onto the top surface of the locking-targeting-guide 12. The restraining plate 16 holds the upper alignment rod segments 138 within the locking-targeting-guide 12, until the upper alignment rod segments 138 are joined to the lower alignment rod segments 146 and the locking-targeting-guide 12 is ready to be positioned. The alignment rod restraining plate 16 may also prevent motion of the locking-targeting-guide 12 on the assembled alignment rods until the locking-targeting-guide 12 is to be used.

With reference to FIGS. 1, 2, 3, 10, and 27, the alignment rod restraining plate 16 is clipped onto the top of the locking-targeting-guide 12. That is, the alignment rod restraining plate 16 snaps into the large central fenestration 45 on the top surface of locking-alignment-guide. Finger grips 18 extend from a flexible spring plate 23 which rises from an inverted hemispherical shell 22 that descends from the lower surface of the alignment rod restraining plate 16. When the hemispherical shell 22 is placed into the central fenestration 45 of the locking-targeting-guide 12 locking edges 21 engage insert locking groove 52. When the finger grips 18 are compressed together against the force of the spring plate 23, the locking edges 21 disengage from the insert locking groove 52, and the alignment rod restraining plate 16 can be lifted from the top of the locking-targeting-guide 12. The alignment rod restraining plate 16 has a plurality of cylindrical bosses 20 on the top surface that correspond to recesses 19 on the bottom surface. The flattened tops 144 of the upper vertical alignment rod segments 138 fit into the plurality of matching recesses 19.

With reference to FIGS. 5, 6, 7, 8, 9 and 10, after the alignment rod restraining plate 16 has been removed from the locking-targeting guide, targeting insert 24 is placed into the central fenestration 45. The targeting insert 24 may have a locking mechanism for holding it into the central fenestration 45 similar to that previously described for the alignment rod restraining plate 16. Such locking mechanism may include insert finger grips 28 which extend from a flexible spring plate 32 which rises from inverted hemispherical shell 30 that descends from the lower surface of the support plate 26. The targeting insert 24 has metal alignment spike 38 that protrudes from a solid central support cylinder 36. When the metal alignment spike 38 is pointing directly at a screw hole and the long axis of the spike is aligned parallel with the x-ray beam it will appear as a circular spot on an x-ray-monitor.

When the locking-targeting-guide 12 has been positioned, the targeting insert 24 is removed from the central fenestration 45 and replaced with cannulated insert 34. The cannulated insert has a centrally located cylinder 40 that has a cannulated center 41. A drill, a depth gauge, a screw driver, and so forth may be guided to the respective screw hole by use of the cannulated insert 34. As is to be appreciated, a plurality of cannulated inserts may be used each having respective dimensions and/or features so as to accommodate different size drills, depth gauges, screw drivers and the like. Alternatively, a single cannulated insert 34 may be used with a drill, depth gauge, and screw driver that have identical diameters.

The locking-targeting-guide 12 will now be further described with reference to FIGS. 10–18.

The locking-targeting-guide 12 may be considered as having four major components. Such components include an outer frame 46, a base component 58, a movable middle plate 66 and a plurality of brake-bearings 64. Each of the four components will now be described.

The outer frame 46 is ideally formed from a radiolucent plastic type material and has a top surface and side surfaces. Two opposing sides each have a relatively large slot 56 through which reset handles 54 of the middle plate 66 project and move. Another side has a docking bay slot 59 where the outer frame 46 engages a docking bay 60 of the base component 58. Such docking bay is where the positioning handle 14 attaches to the locking-targeting-guide 12. On the top surface of the outer frame 46 a plurality of centrally cannulated universal joints 42a are mounted.

Each of the upper universal joints 42a have an outer ring 42b and an inner ring 42c. The lower surface of the inner ring 42c is hemispherical in shape and contacts a respective brake-bearing 64. The upper vertical alignment rod segment 138 passes through the central cannulation of the inner ring 42c of the upper universal joint 42a. In this embodiment, the number of assembled vertical alignment rods, brake-bearings 64, and universal joints are equal.

The top of the outer frame 46 has the large central fenestration 45 which receives the vertical alignment rod restraining plate 16, the targeting insert 24 and the cannulated insert 34. The central fenestration 45 may not extend through the complete thickness of the top surface of the outer frame 46 and may have a shallow cylindrical shape. On the wall of the cylinder is locking groove 52 into which locking edge 21 (FIG. 3) of the alignment rod restraining plate 16 and locking edge 29 (FIG. 9) of the inserts lock. The cylinder 45 terminates in insert block plate 50 having a relatively small central fenestration 48.

The outer frame 46 of the locking-targeting-guide 12 is joined to the base component 58 by a plurality of assembly screws 44. Alternatively, the frame 46 may be coupled to the base component 58 by other types of fasteners or by other means of attachment. The plurality of screws 44 are arranged in recesses 62 so as to be recessed into the top surface of the locking-targeting-guide 12. These screws engage matching threaded recesses 100 located in the top of spring support pillars 70 of the base component 58. The open end of the bottom of the outer frame 46 of the locking-targeting-guide 12 may be coupled to a skirt 111 circumferentially extending around the base component 58.

A further description of the base component 58 of the locking-targeting-guide will now be provided with reference to. FIGS. 15–18. The base component has a top plate 112 and a base plate 110 that are joined together. A slidable lock plate 105 is arranged between the top plate 112 and the base plate 110.

Figure 11:
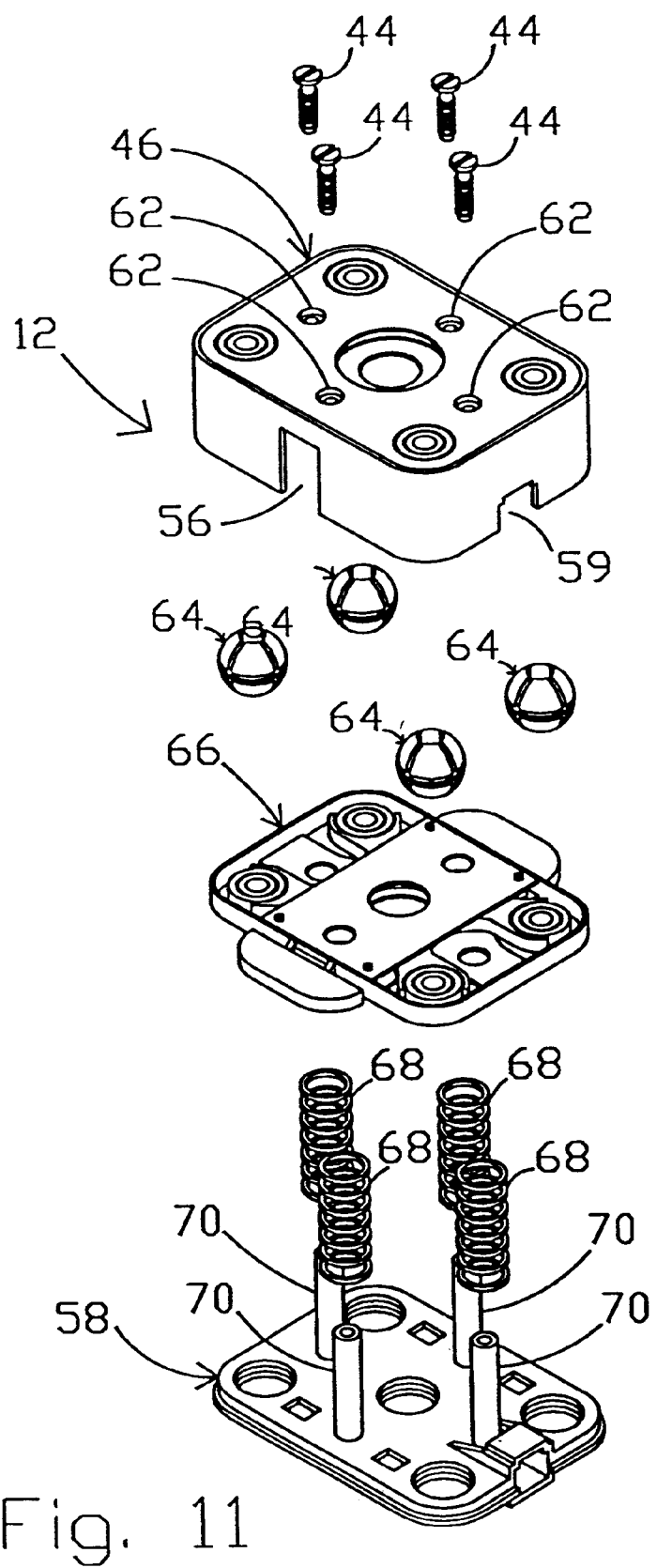
FIG. 11 is an exploded diagram of the locking-targeting-guide of FIG. 10.
Figure 12:
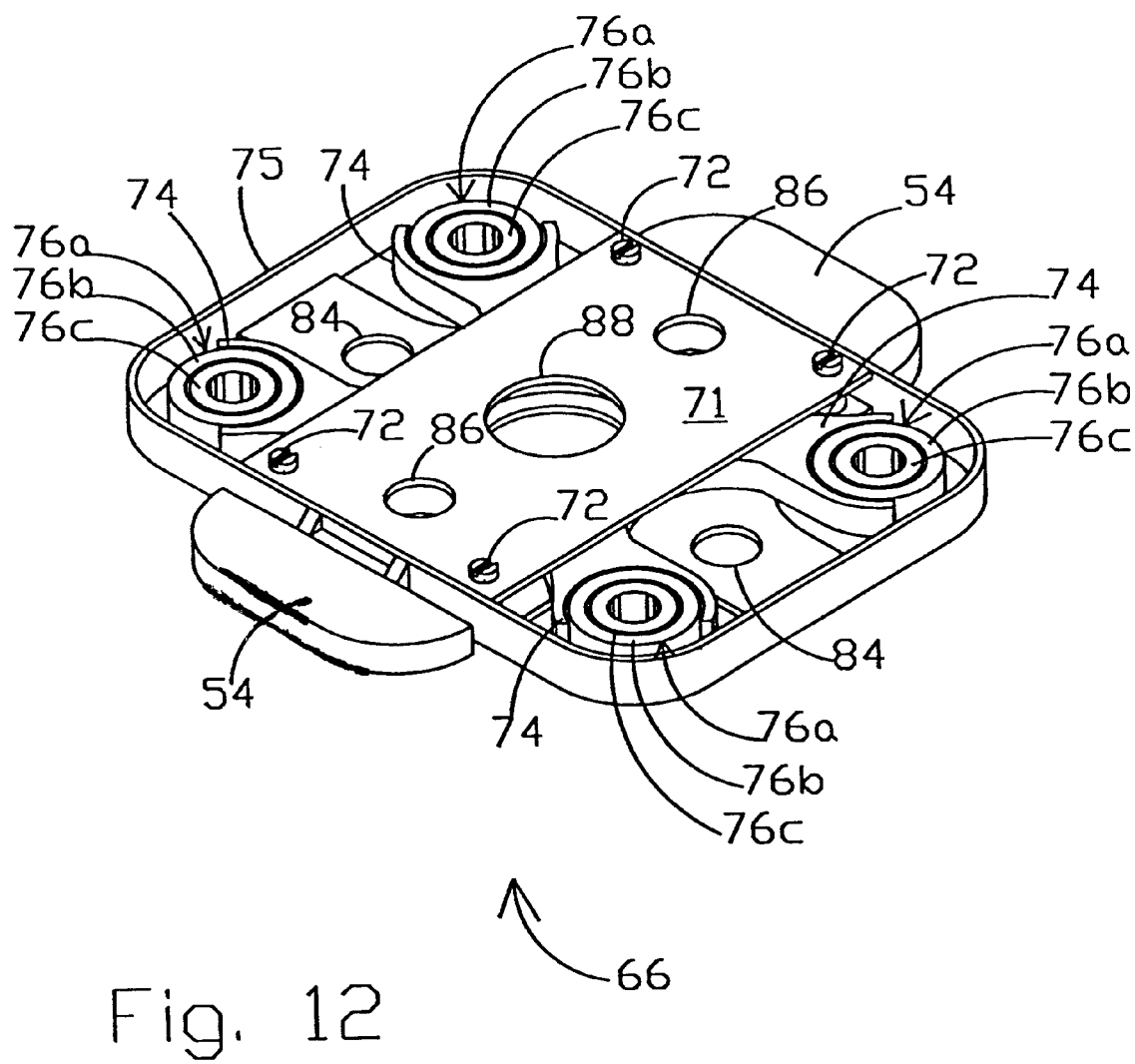
FIG. 12 is a diagram of a middle plate assembly of the locking-targeting-guide of FIG. 10.

The top plate 112 has a plurality of spring support pillars 70 each surrounded by a locking spring 68 (FIG. 11). The spring support pillars 70 extend internally through the locking-targeting-guide so as to contact (or be adjacent to) the inner bottom surface of the outer frame 46 to receive the assembly screws 44.

The top plate 112 and the base plate 110 have a plurality of matching fenestrations or holes. That is, such plates have fenestrations 102 and 114 through which the vertical alignment rods may pass; central fenestrations 104 and 98 through which the alignment spike 38 of the targeting insert 24, the depth gauge, screwdriver and locking screw may pass; and a plurality of matching rectangular catch fenestrations 106 and 108 into which catches 94 (FIG. 14) from the bottom of middle plate 66 enter.

As previously mentioned, the sliding lock plate 105 is arranged in a space between the top plate 112 and the base plate 110. The sliding lock plate 105 may have two degrees of limited horizontal freedom. An elastic or rubber band 122 or the like may be arranged in a band groove 120 on the sliding lock plate 105 and may push the sliding lock plate 105 against restraining ridges 109 such that contact surfaces 107 of the lock plate 105 engage the restraining ridges 109. The elastic band 122 is supported on the inner surface of the base plate 110 by two elastic band posts 115.

Extending from two sides of the sliding lock plate 105 are a plurality of horizontal locking bars 116. The horizontal locking bars 116 are positioned between the matching rectangular catch fenestration 106 and 108. When the plurality of catches 94 descend through the fenestrations 106 they will engage the horizontal locking bars 116.

Figure 34:
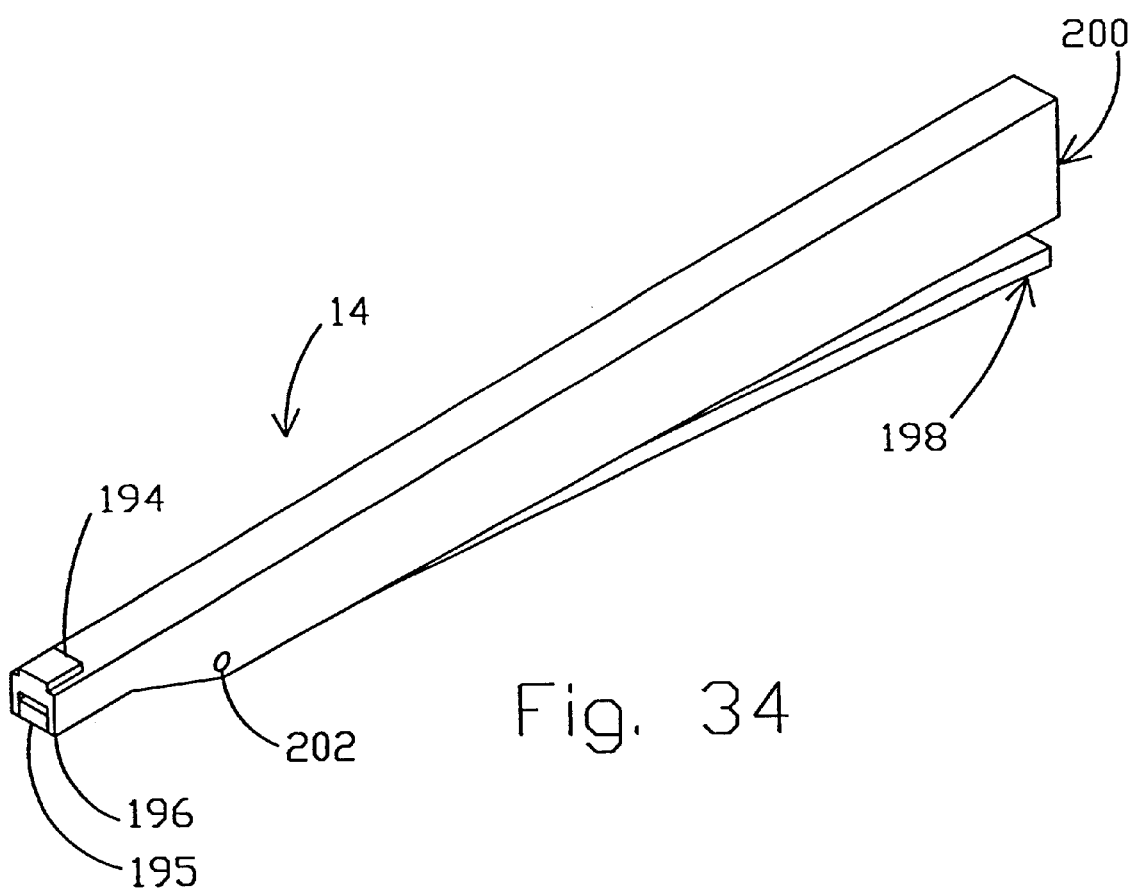
FIG. 34 is an isometric diagram of a handle of the apparatus of FIG. 1.
Figure 39A:
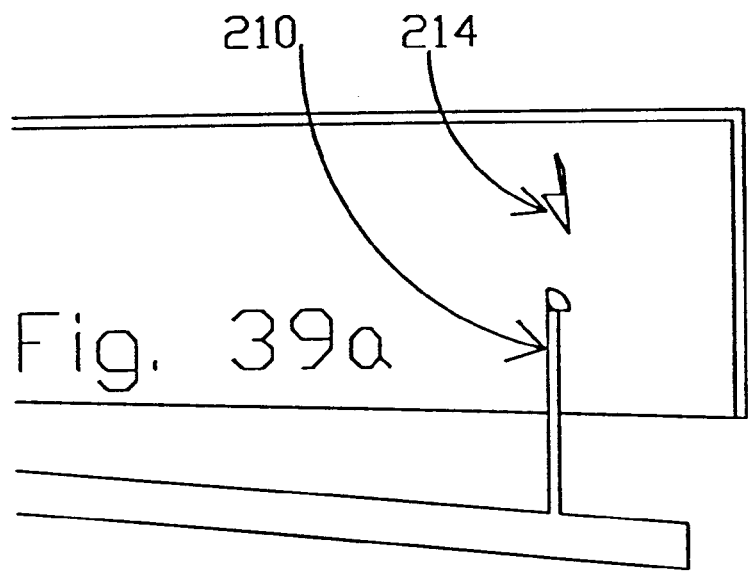
FIG. 39a is a diagram of the lock release reset mechanism of the handle in which the latch and lock/release controller are not engaged.
Figure 39B:
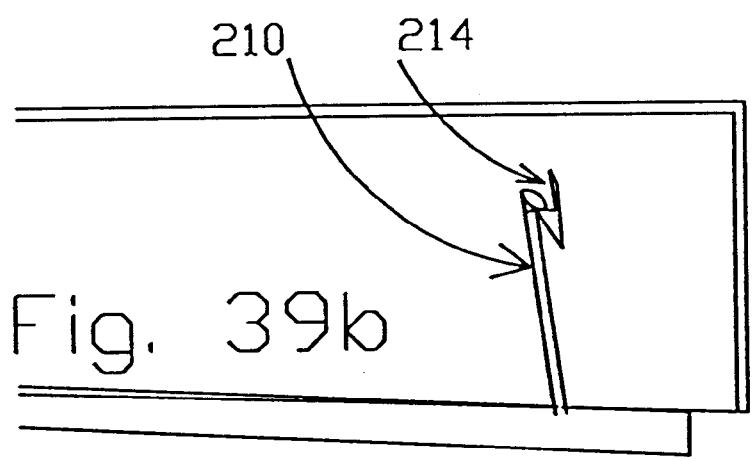
FIG. 39b is a diagram of the lock release reset mechanism of the handle in which the latch and lock/release controller are engaged.
Figure 39C:
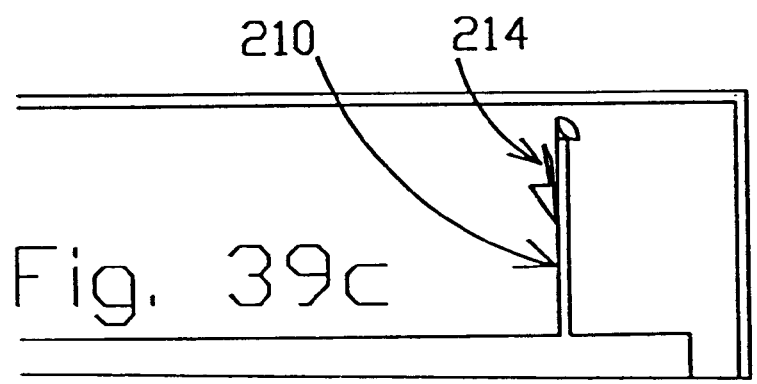
FIG. 39c is a diagram of the lock release reset mechanism of the handle in which the latch and lock/release controller have disengaged and the latch is behind the lock/release controller.
Figure 40:
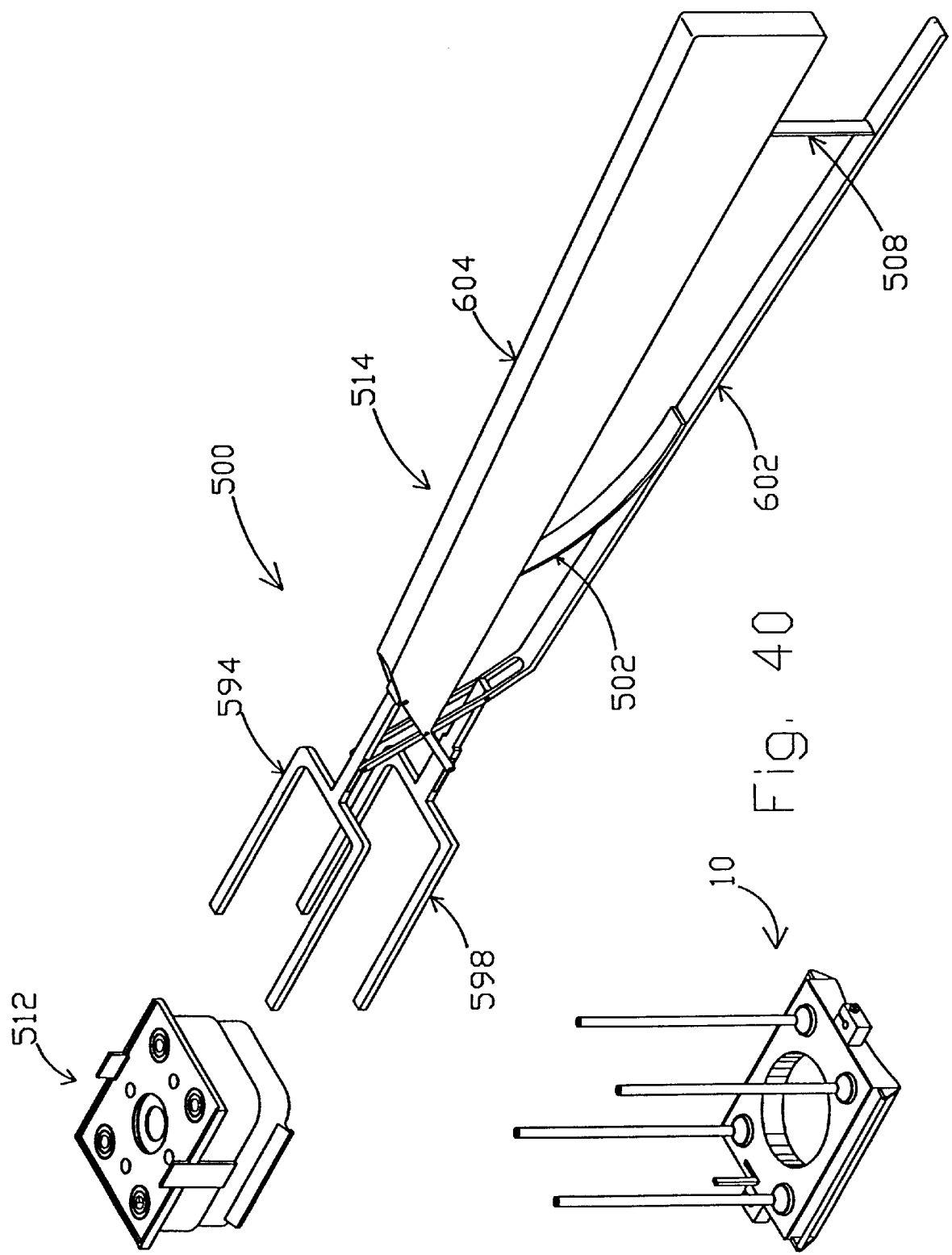
FIG. 40 is a diagram of a handle and locking-targeting-guide according to another embodiment of the present invention.
Figure 41:
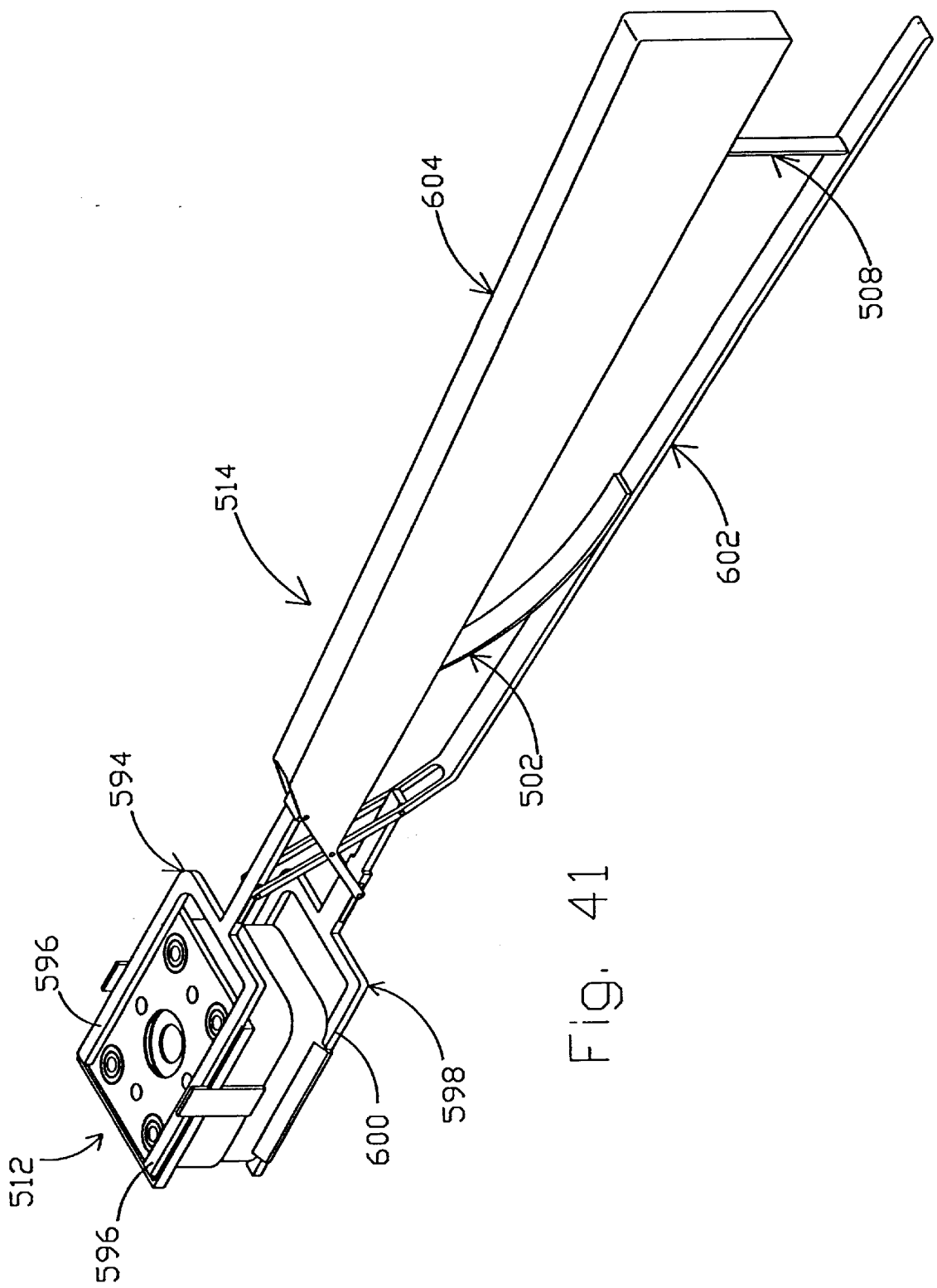
FIG. 41 is a diagram to which reference will be made in explaining the operation of the handle and locking-targeting-guide of FIG. 40.

The top plate 112 has the docking bay 60 into which a handle docking rostrum 196 (FIG. 34) is inserted. The docking bay 60 has a rostrum recess 61 into which a rostrum key 194 (FIG. 34) is inserted. The rostrum recess 61 and rostrum key 194 provide increased contact surface area between the docking bay 60 and the handle docking rostrum 196. Such increased surface area may improve the stability and control of the handle 14 in the locking-targeting-guide 12.

The docking bay 60 fits into docking bay recess 113 of the base plate 110. An open or trigger slot 19 is arranged on the back surface of the docking bay 60. Trigger edge 118 of the sliding lock plate 105 enters the docking port 60 through the trigger slot 119. Pressure against the trigger edge 118 will displace the sliding locking plate 105 against the force of the elastic band 122. Such displacement of the sliding locking plate 105 may release the plurality of catches 94 held by the horizontal locking bars 116. This release would then permit the middle plate 66 to be propelled upwards by the locking springs 68.

The middle plate 66 will now be further described with reference to FIGS. 11–14. The middle plate 66 is located within the locking-targeting guide 12. Spring support pillars 70 pass through fenestrations 84 in the middle plate 66, and two of such pillars also pass through fenestrations 86 of the armature restraining plate 71. The middle plate 66 may be supported by the locking springs 68 and may have two degrees of vertical freedom with regard to the spring support pillars 70.

The top of the middle plate 66 has a shallow tray 75 in which an armature 74 is arranged that holds a plurality of universal joints 76a. Each universal joint 76a has an outer cylinder 76b and an inner cylinder 76c which are arranged such that the axes of rotation of the outer cylinder 76b and inner cylinder 76a is normal to each other. The number of universal joints 76a may be equal to the number of vertical alignment rods. A plurality of catches 94 extend from the bottom surface of the middle tray. Depression of the middle plate 66, by pressure applied to the reset plates 54, will compress the supporting locking springs 68 and permit the catches 94 to engage the horizontal locking bars 116 (FIG. 16) of the sliding locking plate 105.

The armature 74 may have 2 degrees of freedom within the constraints of the middle plate tray 75. The armature 74 is substantially prevented from vertical motion by restraining plate 71 which is attached to the middle plate tray 75. In the current embodiment, the restraining plate 71 and tray 75 are attached by a plurality of screws 72 that pass through fenestrations 90 of the armature restraining plate 71 and are placed into screw pillars 92. However, the present invention is not so limited and other means may be used for coupling together the restraining plate 71 and tray 75.

A universal joint 76a is mounted at the end of each arm of the armature 74. Inner ring 76c of each universal joint 76a has a hemispherical depression on its upper surface which may contact a respective brake-bearing 64. Beneath each universal joint is a relatively large alignment rod fenestration 80 in the middle plate 66.

There are concentric central fenestrations in armature restraining plate 88, armature 78, and middle plate 82 through which the alignment spike 38 of the targeting insert 24, the depth gauge, the screwdriver and locking screw will pass. The central fenestration 78 of the armature is larger than the central fenestrations of either the restraining plate 71 or the middle plate 66 to prevent impingement on insert 24, depth gauge or screw driver with motion of the armature 74.

Reset plates 54 are arranged on opposite sides of the middle plate and extend outwardly therefrom. The reset plates 54 enable the locking-targeting-guide 12 to be released and reset. That is, downward pressure applied to the reset plates 54 will depress the middle plate 66 and compress the locking springs 68. Such downward pressure is continued until an audible/palpable click occurs which indicates that the catches 94 on the bottom of the middle plate 66 have engaged the horizontal locking bars 116.

Figure 16:
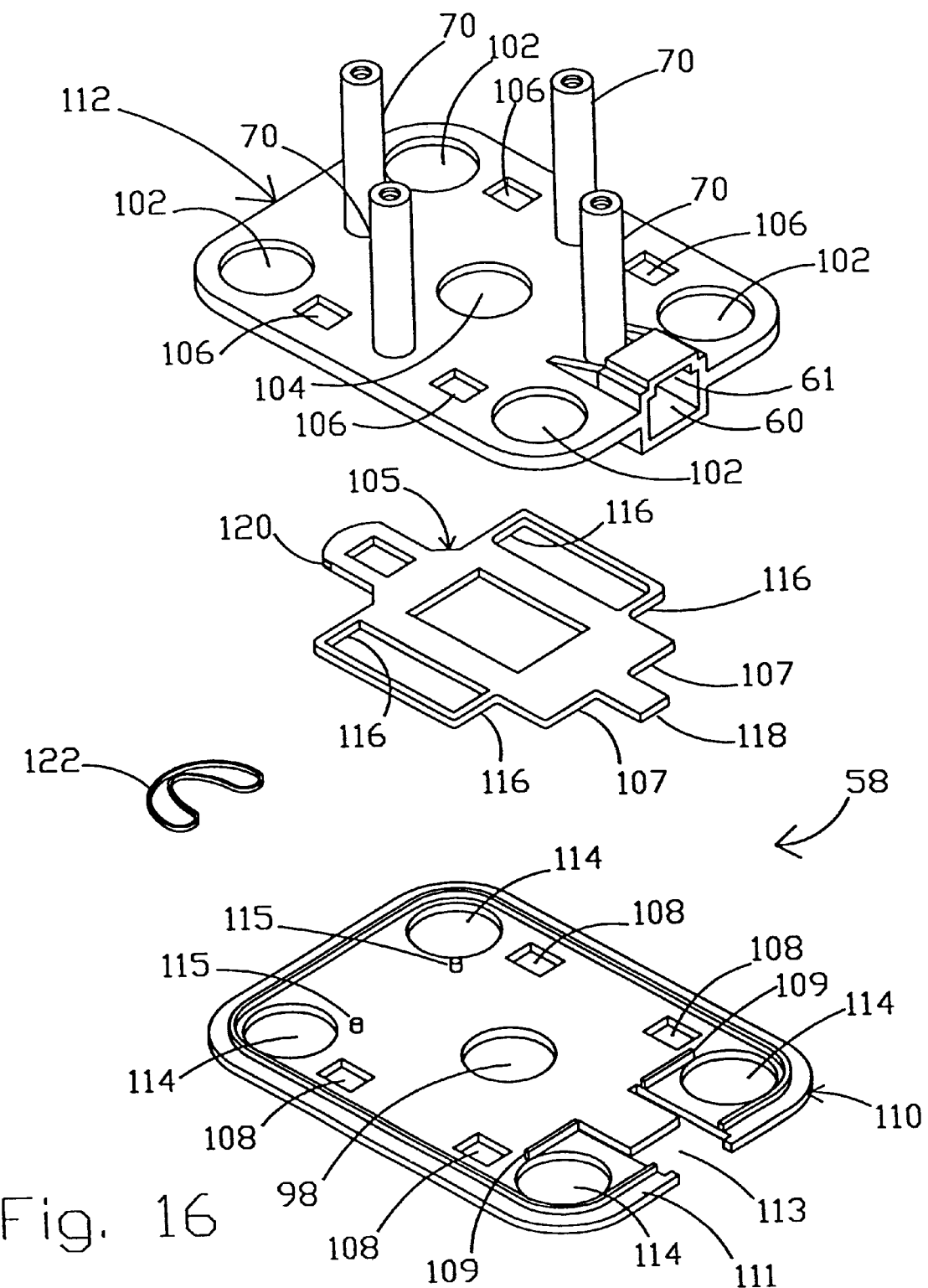
FIG. 16 is an exploded diagram of the base portion of the locking-targeting-guide of FIG. 15.
Figure 17:
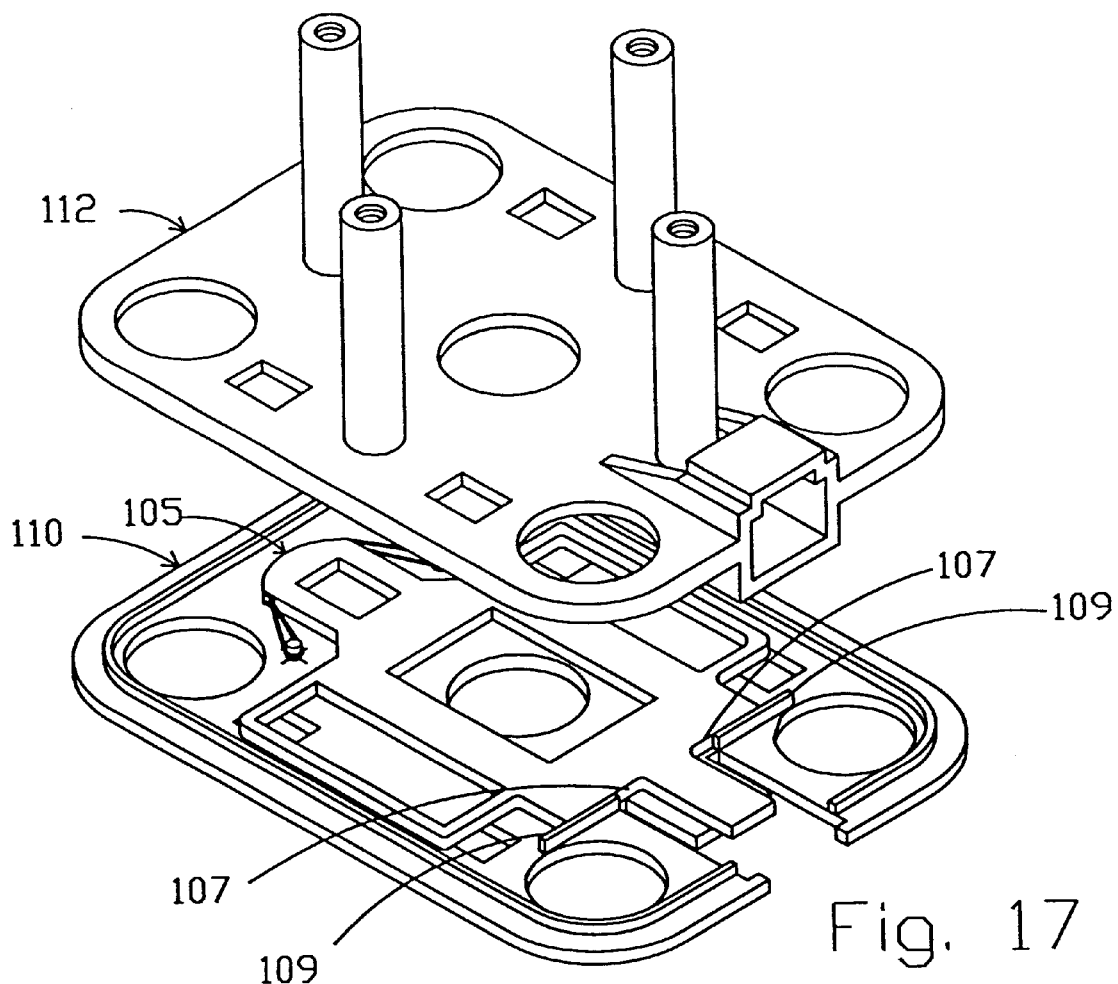
FIG. 17: is a partial exploded diagram of a sliding lock plate within the base portion of the locking-targeting-guide of FIG. 15.
Figure 18:
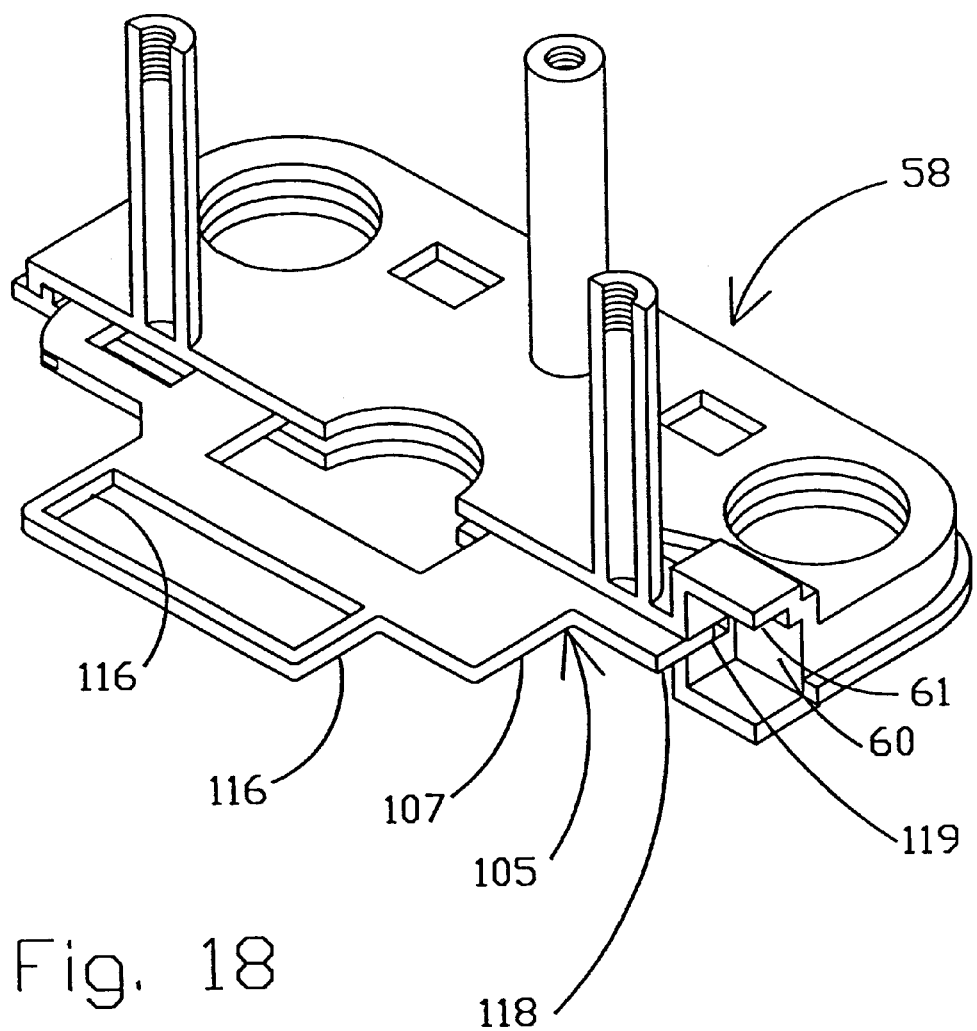
FIG. 18 is a partial diagram of the base portion of the locking-targeting-guide of FIG. 10.

Upon depressing middle plate 66 onto base component 58, engagement edges 95 of catches 94 may contact horizontal locking bars 116 (FIG. 16). Further depression of the middle plate 66 may produce pressure from slide surfaces 97 against the horizontal locking bars 116. The downward pressure on middle plate 66 is continued until the slide surfaces 97 have passed completely below the locking bars 116, whereupon the locking bars snap back to their pre-displacement position and engage locking ledges 96 of catches 94.

Figure 19:
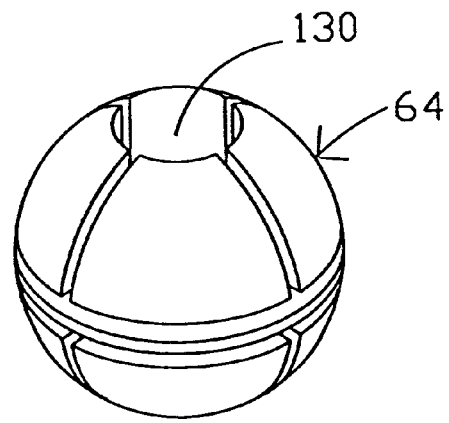
FIG. 19 is a diagram of a brake-bearing.

A locking mechanism within the locking-targeting-guide 12 will now be described with reference to FIG. 19-i. Such locking mechanism may reversibly rigidly grip a vertical alignment rod. The locking mechanism is composed of a cannulated spherical deformable braking-bearing 64 positioned between an upper cannulated universal joint 42a and a lower cannulated universal joint 76a. The upper universal joint 42a is incorporated into the top of the outer frame 46 of the locking-targeting-guide 12 and the lower universal joint 76a is set at the end or extremity of armature 74. A respective vertical alignment rod passes through central cannulation 130 of the brake-bearing 64 and the upper and central fenestrations in the inner rings of the upper and lower universal joints. There is a set of upper and lower universal joints with an interposed brake bearing to grip each vertical alignment rod.

The locking mechanism is activated by compression of the upper and lower universal joints 42a, 76a against the brake-bearing 64. When axial pressure is applied against the brake-bearing 64 by the upper and lower universal joints 42a, 76a the brake-bearing 64 will deform and grip the assembled vertical alignment rod. This will lock the locking-targeting-guide 12 in the selected position. The locked position is sustained for as long as the universal joints 42a, 76a compress the brake-bearing 64.

Deformation of the brake-bearing 64 may occur with axial compression. Such axial compression may be provided by placing the brake-bearing 64 between two universal joints 42a, 76a, in which the lower universal joint 76a mounted on the armature 74 has 4 degrees of horizontal freedom to follow the motion of the assembled vertical alignment rod. The upper and lower universal joints 42a, 76a can produce axial compression on the break-bearing 64 regardless of the position of the assembled vertical alignment rod.

Sustained compression of the upper and lower sets of universal joints 42a, 76a against the brake-bearing 64 is provided by the locking springs 68 that support the middle plate 66. However, when the catches 94 of the middle plate 66 have engaged the horizontal locking bars 116, the middle plate is held distracted or removed from the outer frame 46. In such situation, the upper and lower universal joints 42a, 76a are held apart, whereupon the brake-bearings 64 may rest upon the upper hemispherical surfaces of the inner ring 76c of the lower universal joint 76a.

Release of the catches 94 will permit the compressed locking springs 68 to forcibly expand. The springs will forcibly lift the middle plate 66 (with lower universal joints 76a) and brake-bearings 64 against the upper universal joints 42a. The sustained force of the released springs 68 will produce axial compression on the upper and lower universal joints 42a, 76a against the brake-bearings 64. The compression of the brake-bearings 64 will cause the brake-bearings to deform and grip the centrally located assembled vertical alignment rods. Such grip of the brake-bearings 64 against the assembled vertical alignment rods will lock the locking-targeting-guide 12 in the desired position. The brake-bearings 64 will remain locked against the assembled vertical alignment rods until the locking springs 68 are compressed such as which may occur when the middle plate 66 is lowered.

Lowering of the middle plate 66 and compression of the locking springs 68 is accomplished by applying downward pressure on the reset plates 54. Such pressure on the reset plates 54 will terminate the axial compression of the universal joints 42a, 76a against the brake-bearing 64.

When the axial compression is terminated the deformation of the brake-bearing 64 may be reversed so as to return to its original shape. When the brake-bearing 64 returns to its original or resting shape, it may not grip the centrally located assembled vertical alignment rod. To release or terminate the axial compression, the reset plates 54 are depressed until an audible/palpable click occurs indicating that the catches 94 have engaged the horizontal locking bars 116. As a result, the locking-targeting-guide is reset and again has a number (such as six) of degrees of freedom with regard to the assembled vertical alignment rods.

The brake-bearing 64 will now be further described with reference to FIGS. 19–23. As previously indicated, the present embodiment utilizes a brake-bearing 64 for each assembled vertical alignment rod. As previously described, when axial compression is applied to the brake-bearing 64, it will reversibly deform from a spherical shape and grip an assembled vertical alignment rod that passes through the brake bearing center. The brake-bearing 64 will return to a resting spherical shape when such compression is terminated.

The brake-bearing 64 is divided into upper and lower hemispheres, which, in turn, are divided into a plurality of substantially identical spherical segments 124. Each spherical segment 124 has a rubberized braking surface 125 that will contact and grip the shaft of a vertical alignment rod. In place of the rubberized braking surface, other types of non-slip gripping surfaces may be used. A cannulated discoid equatorial spring plate 126 is located between the upper and lower hemispheres. The equatorial spring plate has a central fenestration 132 which permits passage of the alignment rod.

Each brake-bearing spherical segment 124 is pivotally attached to an individual spring 128. The springs 128 are fixed to and arise from the equatorial spring plate 126 and have a pivot barrel 136 at one end thereof. The pivot barrel 136 of each spring 128 is arranged within a pivot trough 134 of the spherical segment 124. There is one spring 128 for each spherical segment 124. An axle or rod is placed through each spherical segment 124 and each pivot barrel 136, pivotally joining each spherical segment 124 to each spring 128.

The springs 128 hold the spherical segments 124 away from each other, away from the centrally located assembled vertical alignment rod, and away from the equatorial spring plate 126. In the resting position when there is no compression on the brake-bearing 64 it has a spherical shape. When axial compression is applied to either hemisphere, the springs 128 will compress. In such situation, the springs 128 will bend in a central direction bringing all the spherical segments 124 of the hemisphere(s) closer together. When the spherical segments 124 are brought closer together, their braking surfaces 125 will be pressed against the centrally positioned vertical alignment rod. The pivot 136 attachment of each spherical segment 124 to the spring 128 held to ensure contact of each braking surface against the vertical alignment rod.

A description of the handle 14 will now be provided with reference to FIGS. 34–39C. The handle 14 has a body 200 and a handle-trigger 198 which is pivotally attached to the handle body 200 at 202. One end of the handle 14 or rostrum 196 is insertable into the locking-targeting-guide 12. The opposite end of the handle may be grasped by the surgeon or operator to manipulate the locking-targeting-guide 12.

More specifically, the rostrum 196 is adapted to be inserted into the docking bay 60 (FIG. 10) of the locking-targeting-guide 12. The top surface of the rostrum 196 has a rostrum key 194 which provides increased contact surface area and stability with the docking bay 60. A pressure/lock plate 195 is arranged at the rostrum end 196 of the handle-trigger 198. When the rostrum 196 is inserted into the docking bay 60, the pressure lock plate 195 is concealed within the rostrum 196. When the rostrum 196 is completely seated in the docking bay 60, the handle-trigger 198 may be squeezed or compressed so as to rotate about the pivot 202. Such rotation of handle-trigger 198 will deploy the pressure lock plate 195 concealed within the rostrum 196. The pressure lock plate 195 effectively expands the rostrum 196 within the docking bay 60 creating a rigid reliable or secure connection between the locking-targeting-guide 12 and the handle 14.

The shaft of the handle-trigger 198 is divided into three regions, that is, a first portion or handle-trigger pivot region 219, a second portion or handle-trigger spring region 221, and a third portion or handle-trigger lock/release/rest region 223. The pivot region 219 is from the pressure lock plate 195 to where the handle-trigger shaft contacts spring post 204. The spring region 221 is the region of the handle-trigger shaft extending from the contact point with the spring post 204 to flexible latch support 208. The lock/release/reset region 223 is the portion of the handle-trigger shaft that supports the flexible latch support 208.

Squeezing or compressing the handle-trigger 198 is initiated after the handle rostrum 196 has been inserted into the docking bay 60. The compression of the handle-trigger 198 is divided into four phases. The first and second phases of handle-trigger 198 compression are utilized to join the handle 14 to the locking-targeting-guide 12, and the third and fourth phases of handle-trigger compression are utilized to activate a locking mechanism within the locking-targeting-guide 12 and release the handle 14 from the locking-targeting-guide 12, as hereinbelow more fully described.

The first phase of handle-trigger compression will produce rotation of the handle trigger 198 around axle 228 which is positioned in bushing 230 of the handle-trigger. Such first phase is completed when the handle-trigger shaft contacts the spring post 204. The second phase of compression forces the handle-trigger 198 to bend against the spring post 204. In this situation, the handle-trigger 198 may bend and behave like a spring. Such compression of the handle-trigger 198 is continued until a palpable/audible click occurs. This click indicates that the handle-trigger 198 has been locked in the bent spring position. The audible/palpable click indicates that the first and second phases of handle-trigger compression have been completed.

The audible/palpable click may further indicate that a locking mechanism within the handle 14 has been activated to sustain a pressure attachment of the pressure lock plate 195 within the docking bay 60. Once the handle 14 has been pressure locked to the locking-targeting-guide 12, the handle 14 and locking-targeting-guide 12 may effectively behave as a single unit. As a result, the handle 14 can be manipulated to position the locking-targeting-guide 12 in a desired position.

The third and fourth phases of handle-trigger compression are initiated when it is desired to lock the locking-targeting-guide 12 in a selected-or desired position. In the third and fourth phases, the handle-trigger 198 may be maximally or further compressed and then released. The release of the handle-trigger 198 will simultaneously release the handle 14 from the locking-targeting-guide. The handle 14 will also be reset so as to be ready for re-attachment to the locking-targeting-guide 12 when locating another distal locking screw.

The third phase of handle-trigger 198 compression activates the locking mechanism in the locking-targeting-guide 12. The third phase of compression will deploy a probe 232 from within the handle 14. The probe 232 will pass out of the handle rostrum 196 and forcibly press against trigger edge 118 of the sliding lock plate 105 (FIG. 16). The sliding lock plate 105 may be displaced against the force of elastic band 122 by the pressure or force of the probe 232. The displacement of the sliding lock plate 105 will move the horizontal locking bars 116 which will release the catches 94 that extend from the bottom of the middle plate 66. The release of the catches 94 will permit the compressed locking springs 68 to expand which will lift middle plate 66, lower universal joints 76a, and brake-bearings 64. This will cause the brake-bearings 64 to become compressed between the upper and lower universal joints 42a, 76a. The compressed brake-bearings 64 will deform and grip the assembled vertical alignment rods locking the locking-targeting-guide 12 in the selected position. This sequence will occur very rapidly.

Within body 200 of the handle 14 is spring mounted probe 232 which has a long flattened probe bar 242 held in horizontal guide tracks 240. The guide tracks 240 are located on opposite inner walls 218 of the handle body 200. The guide tracks permit the probe 232 to have 2 degrees of horizontal freedom. The end of the probe 232 at the rostrum of the handle 196 is substantially flat and normal to the long axis of the probe. Such rostrum end of the probe is activation end 238. The opposite end of the probe bar 242 terminates in a cylindrical spring barrel 224. The spring barrel 224 terminates in a discoid spring compression plate 222. A coiled probe spring 220 surrounds the spring barrel 224. The probe spring 220 is positioned in a cylindrical spring chamber 234 of the handle 14. The hemicylindrical walls of the spring chamber 234 may be molded into the opposite inner walls 218 of the handle body 200.

When the handle rostrum 196 is inserted into the docking bay 60, the probe activation end 238 is recessed within the rostrum. The probe 232 is recessed in the handle by the force of probe spring 220. The probe spring 220 pushes against the inner wall of the spring chamber 234 and the opposite spring compression plate 222 coupled to the probe 232. The pressure of the spring 220 against the spring compression plate 222 keeps the probe 232 positioned within the handle body 200 until the handle-trigger 198 is compressed.

On the lower surface of the probe bar 242 is a set of brackets 226. A linking bar 206 is pivotally attached to the brackets 226 by use of an axle 236. The linking bar 206 is also pivotally attached to a second set of brackets 216 on the upper surface of the handle-trigger 198 by use of an axle 237. The linking bar 206 extends between the handle-trigger 198 and the probe bar 242.

When the handle-trigger 198 is compressed, the linking bar 206 will push the probe bar 242 forward toward the handle rostrum 196. During the first and second phases of handle-trigger compression, the probe bar 242 is advanced through the rostrum so that activation end 238 just contacts the trigger edge 108 of the sliding lock plate 105. The third and fourth phases of handle-trigger compression will further deploy the activation end 238 of the probe 232 out of the rostrum 196. The additional or maximum compression of the handle-trigger 198 will produce such further or minimum deployment of the activation end 238 of the probe bar 242 into the locking-targeting-guide 12. Such deployment of the activation end 238 of the probe 232 will shift the sliding lock plate 105 and activate the locking mechanism in the locking-targeting-guide 12.

The handle-trigger mechanism which locks after the first and second phases of handle-trigger compression and releases with the conclusion of the third and fourth phases of handle-trigger compression will now be further described with reference to FIGS. 35 and 36. Arising from the rear top surface of the handle-trigger 198 is a vertical flexible latch stem 208 which is substantially normal to the long axis of the handle-trigger. The latch stem 208 is substantially narrower than the width of the handle-trigger 198, and is centered in the handle-trigger 198. One end of the latch stem 208 has a horizontal transverse latch 210. The width of latch 210 may be substantially equal to the width of the handle-trigger 198.

Compression of the handle-trigger 198 forces the latch 210 to make contact with a lock/release controller 214. There are two identical lock/release controllers 214 arranged or molded into opposites sides of the inner walls 218 of the handle body 200. During compression or squeezing of handle-trigger 198, the transverse latch 210 contacts both lock/release controllers 214 and the flexible latch stem 208 will pass through the space between the lock/release controllers 214.

Compression of the handle-trigger 198 will force curved latch slide surface 209 against angled guide contact surface 212 of controllers 214. The angled guide surfaces 212 of the lock/release controllers 214 will force the flexible latch stem 208 to bend toward the handle rostrum 196. The slide surface 209 will follow the guide surfaces 212 of the lock/release controllers 214 through the first and second phases of handle-trigger compression. The second phase of handle-trigger compression is concluded when the slide surface 209 reaches a termination portion of guide contact surfaces 212. That is, each guide contact surface 212 terminates in a flat controller lock surface 215 which is substantially parallel with the long axis of the handle 14. The flexible latch stem 208 was progressively bent towards the handle rostrum 196 as the latch slide surface 209 followed the guide contact surfaces 212 during the first and second phases of handle-trigger compression. When latch lock surface 211 reaches the controller lock surface 215, the bent latch stem 208 will snap back to its original vertical position and the latch lock surface 211 will be locked against the controller lock surface 215. At such time, a palpable/audible snap may occur as the two surfaces engage.

The latch 210 will remain firmly locked against the controller 214 by the spring deformation of the handle-trigger 14. That is, the second phase of handle-trigger compression progressively bent the handle-trigger 198 against the spring post 204. Therefore, the second phase of handle-trigger compression produces spring deformation in the handle-trigger which produces a reliable pressure lock of the latch lock surface 211 against the controller lock surfaces 215.

When the third and fourth phases of handle-trigger compression are initiated, the latch slide surface 209 will be forced against second angled guide surfaces 213 of the lock/release controllers 214 which will force the flexible latch stem 208 to bend towards the handle rostrum 196. The third and fourth phases of handle-trigger compression are concluded when the latch slide surface 209 reaches the apex of the second guide surfaces 213.

At the termination of the second guide surfaces 213, the bent latch stem 208 may snap back to its original vertical position. At such time, an audible/palpable snap may occur which may be detected by the surgeon. As such, the surgeon will also recognize that the handle-trigger 198 may not be further compressed.

When compression of the handle-trigger 198 has been completed but compression has not yet been released, the latch stem 208 will have returned to its original vertical position. The latch 210 will be located behind the lock/release controllers 214. When compression of the handle-trigger 198 is released, the latch 210 will ride against controller release/reset surfaces 217 which will force the latch stem 208 to bend towards the rear of the handle 14, away from the rostrum 196. The latch 210 will follow the controller release/reset surfaces 217 as the handle-trigger 198 is released.

When the latch 210 reaches the lower termination of the controller release/reset surfaces 217, the latch stem 208 will snap back to its original vertical position. As such, the latch 210 will be reset to its original position beneath the lock/release controllers 214. The handle-trigger 198 is returned to its original position by the combined release of the spring deformation of the handle-trigger 198 and the force of the expanding probe spring 220.

The return of the handle-trigger 198 to its original non-compressed position terminates the pressure grip of the handle-trigger pressure lock plate 195 within the docking bay 60 of the locking-targeting-guide 12. As a result, the handle 14 may be easily detached from the locking-targeting-guide 12.

A description of an operation involving the present apparatus, will now be provided.

The present apparatus may be used after the intramedullary nail has been placed into the bone. More specifically, initially the foundation 10 of the present apparatus is attached to the injured limb, over the distal screw holes of the implanted intramedullary nail. Brief intraoperative x-rays may be used to position the foundation 10 on the skin over the distal screw holes of the implanted intramedullary nail. The foundation 10 may then be attached to the underlying bone with a plurality of metal fixation pins 25 placed between the foundation and the patient and which may be drilled into the underlying bone. Alternatively, the foundation 10 may be fixed to the limb with a relatively wide neoprene strap 250.

After the foundation 10 is rigidly attached to the limb, the locking-targeting-guide 12 is snapped onto the foundation 10. The removable handle 14 is then snapped into the locking-targeting-guide 12. Next, the factory or pre-assembled restraining plate 16 (which prevented premature motion of the locking-targeting-guide) may be removed from the top of the locking-targeting-guide 12 and replaced by the removable targeting insert 24. After the targeting insert 24 is snapped into the locking-targeting-guide 12, the freedom lever 158 may be released on the foundation 10. Such foundation freedom lever also prevented premature motion of the locking-targeting-guide 12.

The release of the foundation freedom lever 158 permits the locking-targeting-guide 12 to have substantially unrestricted motion through a number (such as six) of degrees of freedom as directed by the handle 14. Brief intraoperative x-rays may be used to guide the positioning of the locking-targeting-guide 12 over a distal screw hole. As a result, the targeting insert 24 may be easily positioned directly over a distal screw hole in the implanted intramedullary nail.

The intraoperative portable x-ray is positioned such that the path of the x-ray beam is parallel with a selected distal screw hole. As such, the screw hole will appear as a substantially perfect clear circle on the x-ray monitor. When the targeting insert 24 is positioned over the screw hole it will appear as a circular black spot centered in the screw hole.

When the targeting insert 24 is properly positioned over the screw hole, the handle 14 is rapidly but gently squeezed. The handle 14 will activate the locking mechanism in the locking-targeting-guide 12 so as to fix the locking-targeting-guide directly over the screw hole.

The handle 14 may perform three functions. That is, the handle may be used to position the locking-targeting-guide 12, to trigger the locking mechanism within the locking-targeting-guide 12, and to spontaneously detach from the locking-targeting-guide after the locking mechanism of the locking-targeting-guide has been triggered. Since, the weight of the handle 14 extending from the locking-targeting-guide 12 may represent a potential deforming force, it is advantageous to remove the handle after the locking-targeting-device has been locked in a selected position.

After the handle 14 has been detached from the positioned locking-targeting-guide 12, the targeting insert 24 may be removed and replaced with the cannulated drill insert 34. The cannulated drill insert 34 may be used to guide a drill to bore a hole properly across the bone and through the screw hole of the intramedullary nail. The same cannulated drill insert 34 can be used to guide a depth gauge across the bone so as to measure the optimum length of the distal locking screw. Additionally, the same cannulated drill insert 34 may be used to guide a screw driver with the selected locking screw. X-rays are not required for such steps which use the drill insert.

After the first distal screw has been implanted, the portable x-ray machine is repositioned to place the x-ray beam parallel with the long axis of the second distal screw hole. (Interlocking intramedullary nails may use at least two distal locking screws.) The present apparatus is then reset so as to be positioned over the second distal screw hole. When locating the second distal screw hole, the foundation 10 does not need to be adjusted. The locking mechanism in the locking-alignment-guide 12 is released and reset. Such releasing and resetting of the locking mechanism in the locking-targeting-guide 12 is achieved by manually compressing two plates 54 that extend from opposite sides of the locking-targeting-guide. The handle 14 is once again snapped onto the locking-targeting-guide 12, and the targeting insert 24 is set in place. The present apparatus is then ready to locate the second distal screw hole and facilitate the implantation of the second distal locking screw in a manner similar to that involving the first distal screw. Accordingly, the present device enables a rapid and easy reset to guide the drilling of the second screw hole, to guide the measurement of the second locking screw, and to guide the insertion of the second locking screw.

Other embodiments of the present invention will now be discussed with reference to FIGS. 40–48.

Apparatus 500 includes a locking-targeting-guide 512 and a positioning handle 514. The locking-targeting-guide 512 may function with the previously described foundation 10 or with foundations 516 or 518, hereinafter described, in a substantially similar manner to that of locking-targeting-guide 12 and locking-targeting-guide 512 may include mechanical elements that are substantially similar to those of locking-targeting-guide 12.

Figure 20:
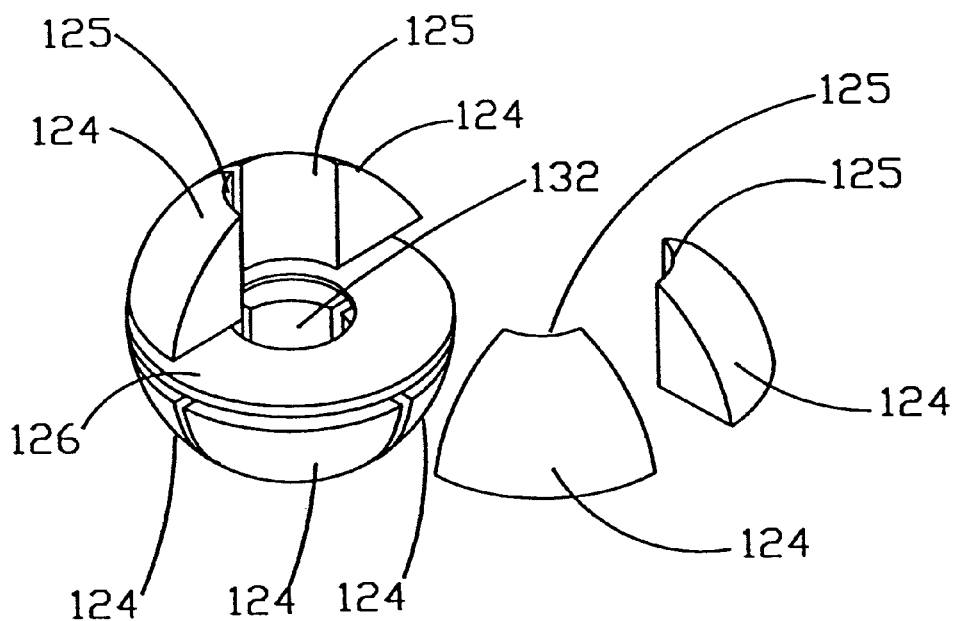
FIG. 20 is a partial isometric exploded diagram of the brake-bearing of FIG. 19.
Figure 21:
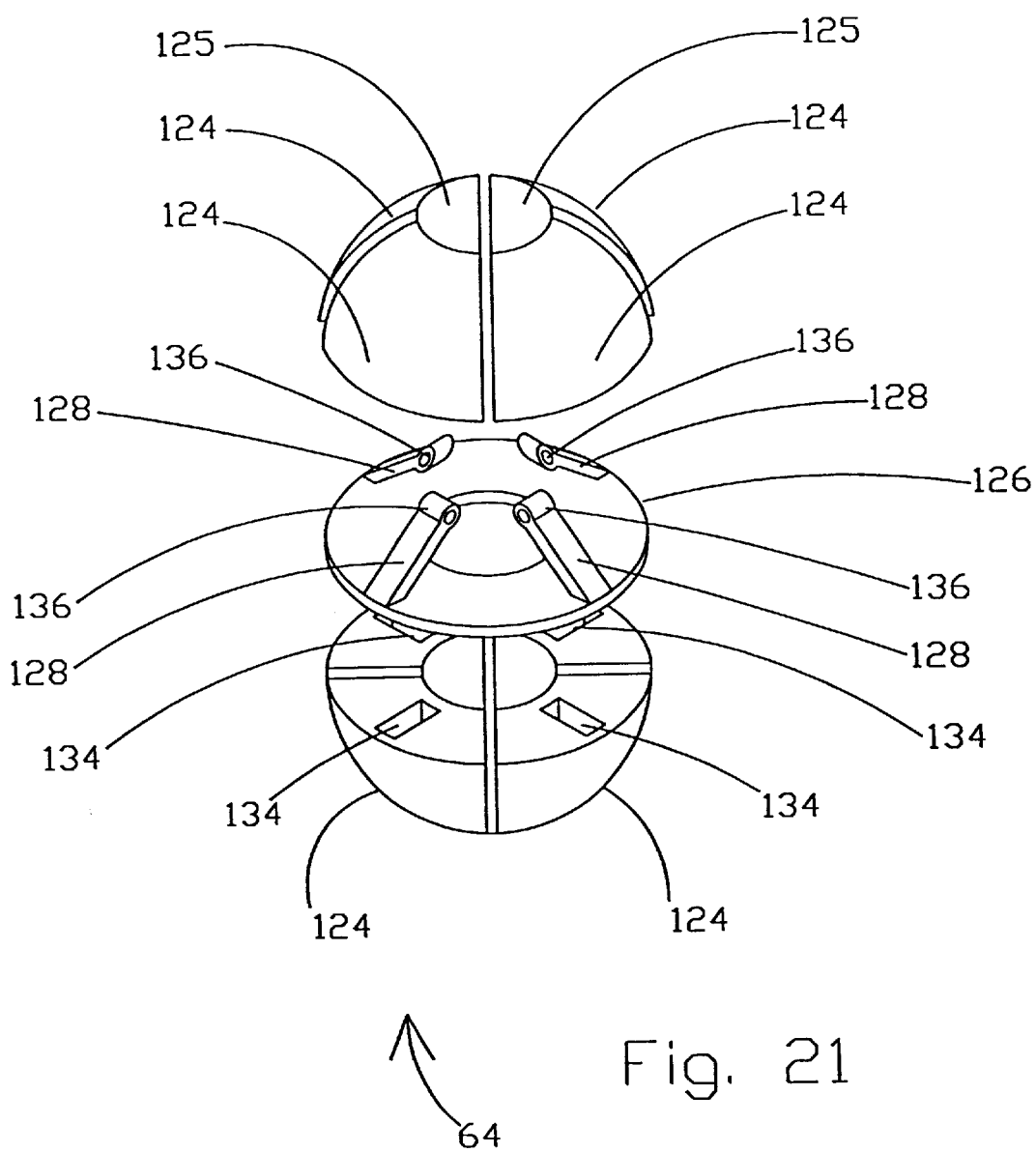
FIG. 21 is an isometric exploded view of the brake-bearing of FIG. 19.
Figure 22:
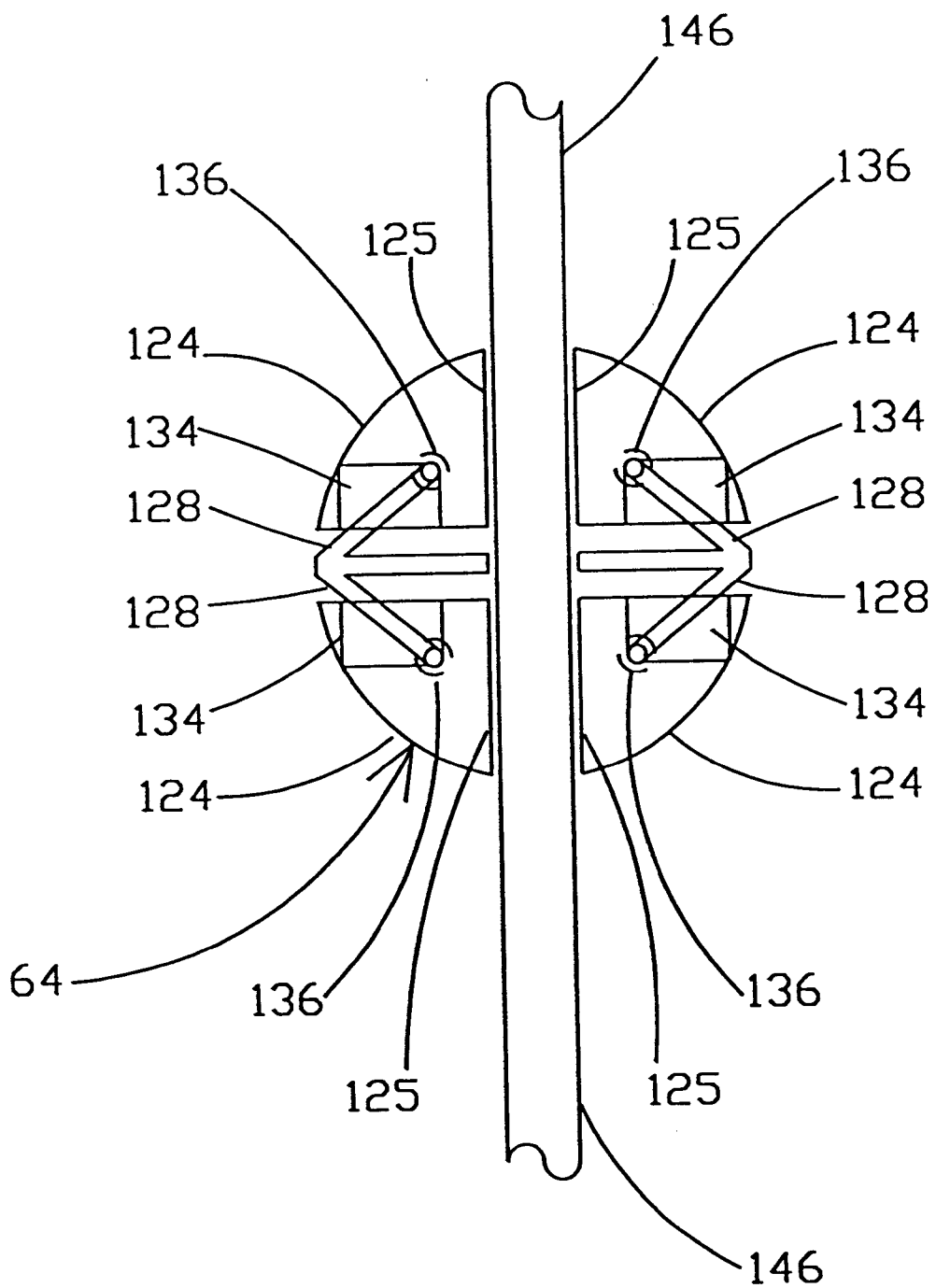
FIG. 22, is a diagram of the brake-bearing of FIG. 19 arranged on a vertical alignment rod in which the brake-bearing has not been compressed and is not gripping the vertical alignment rod.
Figure 23A:
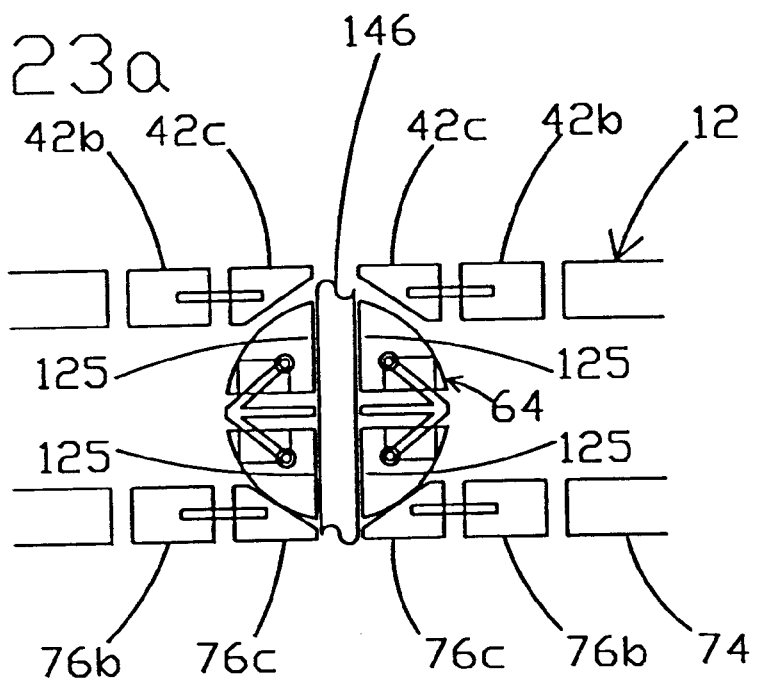
FIG. 23a is a diagram of a non-compressed brake-bearing positioned between upper and lower universal joints wherein the brake-bearing has not been compressed and is not gripping the vertical alignment rod.
Figure 23B:
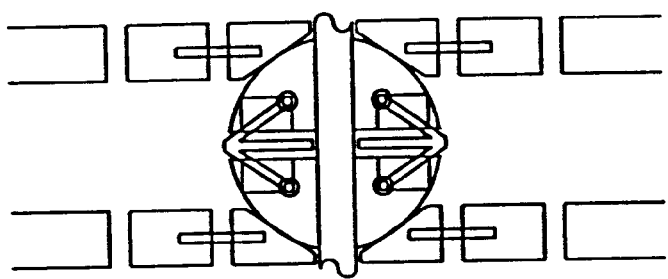
FIG. 23b is a diagram of an activated brake-bearing compressed between the upper and lower universal joints wherein the compressed brake-bearing is gripping the vertical alignment rod.
Figure 23C:
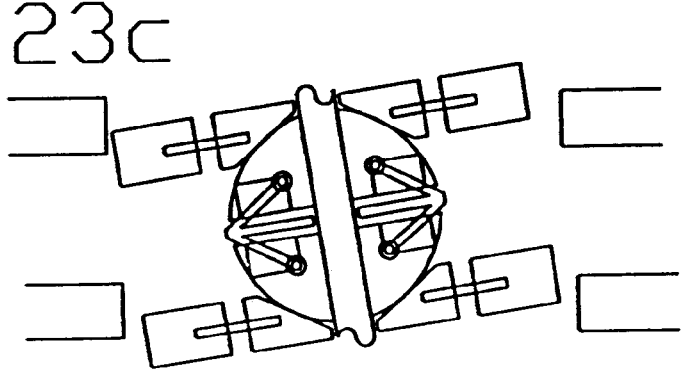
FIG. 23c is a diagram of the activated brake-bearing which has followed and gripped the angled vertical alignment rod.

With reference to FIGS. 43–46, features/elements of locking-targeting-guide 512 will now be described. The locking-targeting-guide 512 has a top frame 546 and a bottom frame 575 which may be compressed together. Such compression of bottom frame 575 and top frame 546 will activate mechanisms that will releasably lock the frames 546 and 575 together and releasably compress brake-bearings 564 onto vertical alignment rods 146 (FIG. 28). The brake-bearings 564 are substantially similar to and function in a substantially similar manner to the brake-bearings 64 (FIGS. 20, 21, 22).

The top frame 546 and bottom frame 575 are forcibly separated by a plurality of springs 568. Compression of the bottom frame 575 and the top frame 546 is resisted by the springs 568. Complete dissociation of the top frame 546 from the bottom frame 575 produced by the pressure of the springs 568 against the under side of surface 520 is prevented by assembly screws 544, or other types of fasteners, that are screwed (or arranged) into spring support pillars 570. The diameter of the head of the assembly screw 544 (or fastener) may be larger than the diameter of the spring support pillar 570. The assembly screw head may rest on the surface 520 or may be recessed into the surface 520. When the top plate 546 and the bottom plate 575 are compressed together, the spring support pillars 570 may be permitted to rise through the fenestrations 562.

The top frame 546 has a plurality of lock-release levers 554 that are pivotally attached to top frame 546 in recesses 504. Each lock-release lever 554 may have an axle 560 and a spring 566 or similar mechanism to forcibly maintain a vertical orientation of the lock-release lever 554. Pressure against upper outer surface 506 of lock-release lever 554 will pivot the lock-release lever about the axle 560.

Figure 43:
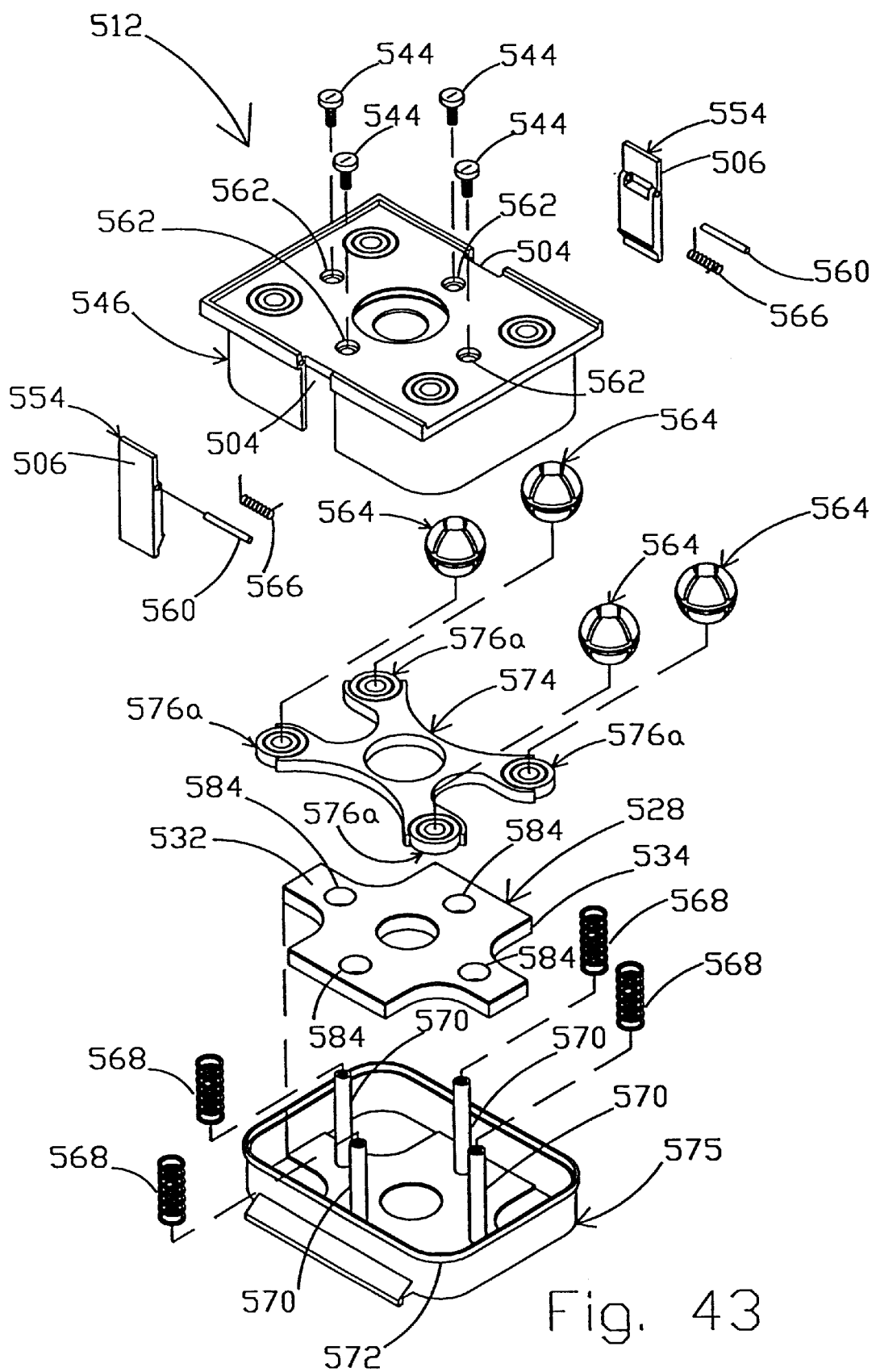
FIG. 43 is an exploded diagram of the locking-targeting-guide of FIG. 42.
Figure 44B:
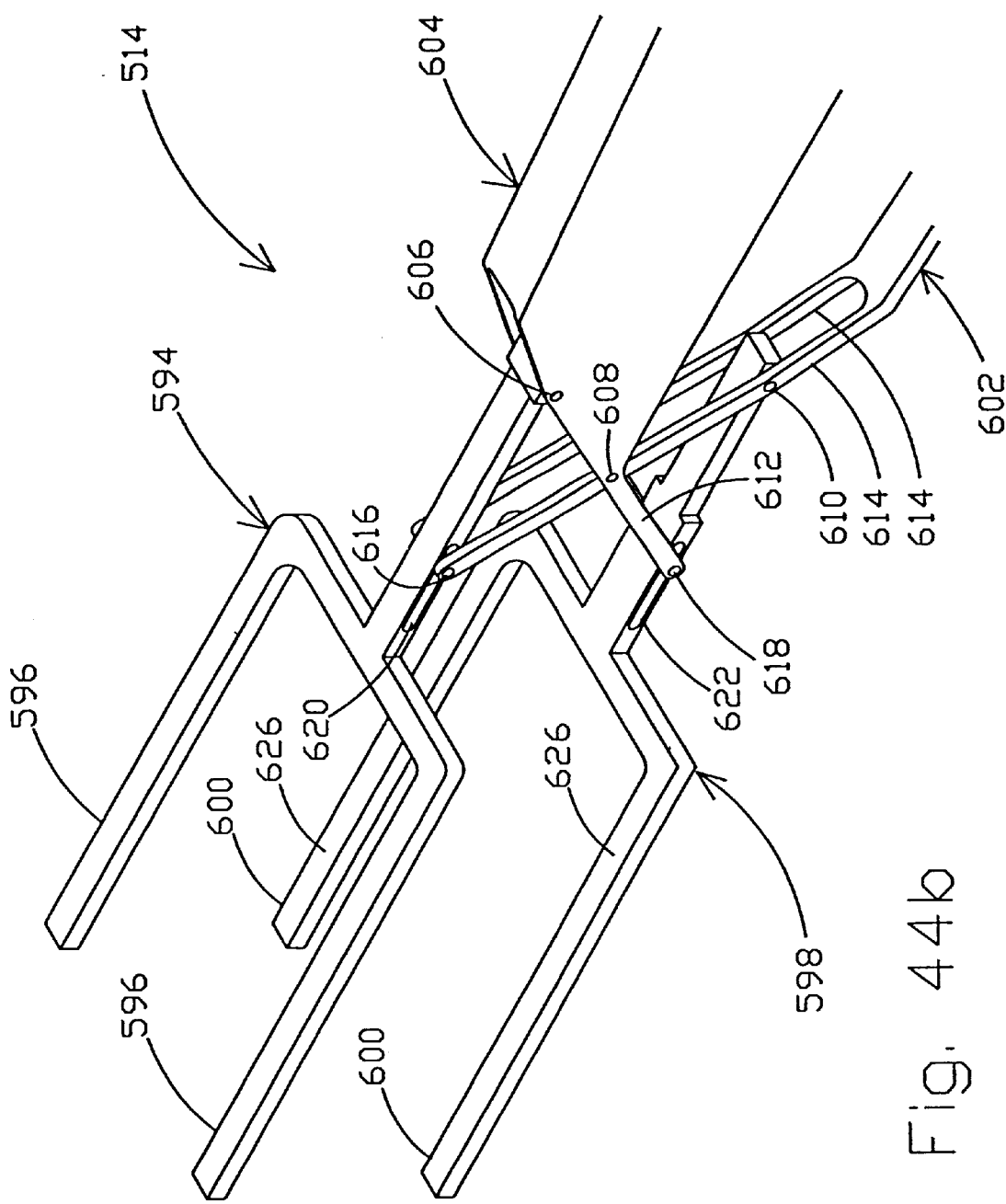

With reference to FIGS. 43, 45 and 46, the bottom frame 575 has a locking rim 572 that is in contact with the inner surface of the top frame 546 when the locking-targeting-guide 512 is properly assembled. When compression is applied to the locking-targeting-guide 512, the locking rim 572 will contact the lever slide 582. Compression of the bottom frame 575 and the top frame 546 will cause the lock-release lever 554 to pivot about the axle 560 against the force of the spring 566. Such compression is continued until undersurface 586 of the locking rim 572 engages lock lever catch 580 of the lock-release lever 554.

When the undersurface 586 of the locking rim 572 meets the lock lever catch-580, the spring 566 will forcibly pivot the lock-release lever 554 to a vertical position. Such movement of the lock-release lever 554 to a vertical position will releasably engage the lock lever catch 580 against the undersurface 586 of the locking rim 572 so as to lock the bottom frame 575 and the top frame 546 together.

The bottom frame 575 may be released from the top frame 546 by applying pressure against upper outer surfaces 506 of the lock-release levers 554 which causes catch surfaces 580 to pivot away from the locking rims 572. When the catch surfaces 580 are pivoted away from the locking rims 572, the springs 568 will expand and displace the top frame 546 from the bottom frame 575.

Figure 13:
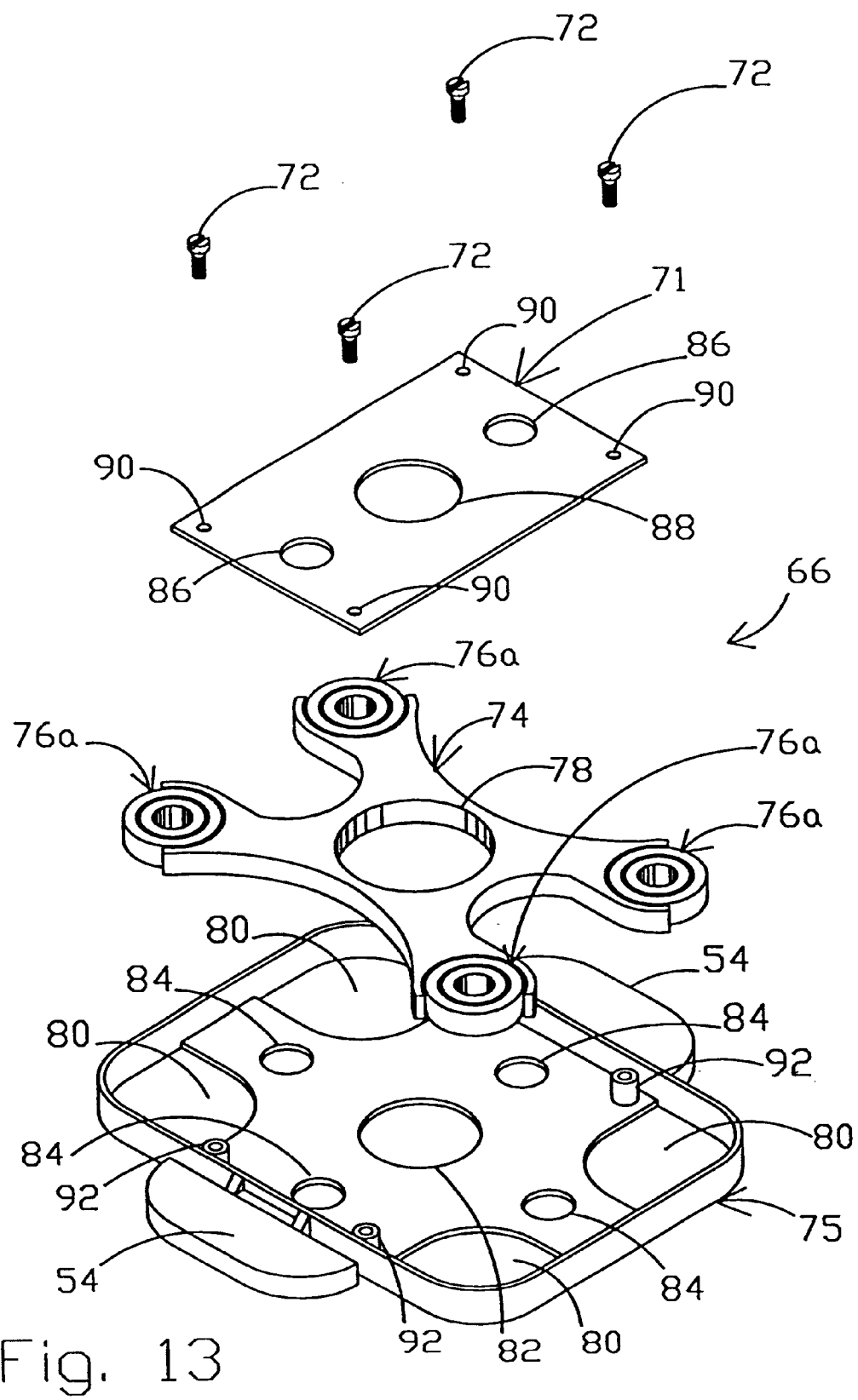
FIG. 13 is an exploded diagram of the middle plate of FIG. 12.
Figure 14:
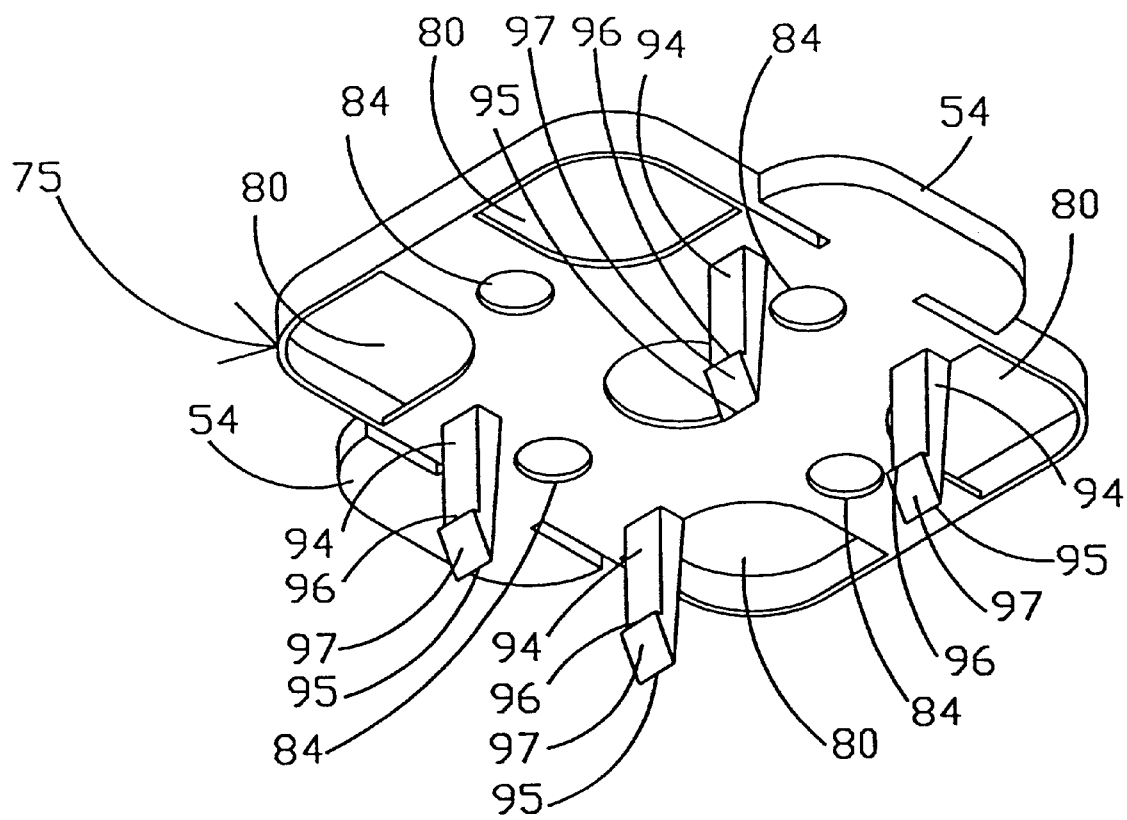
FIG. 14 is a diagram of the bottom of the middle plate of FIG. 12.
Figure 15:
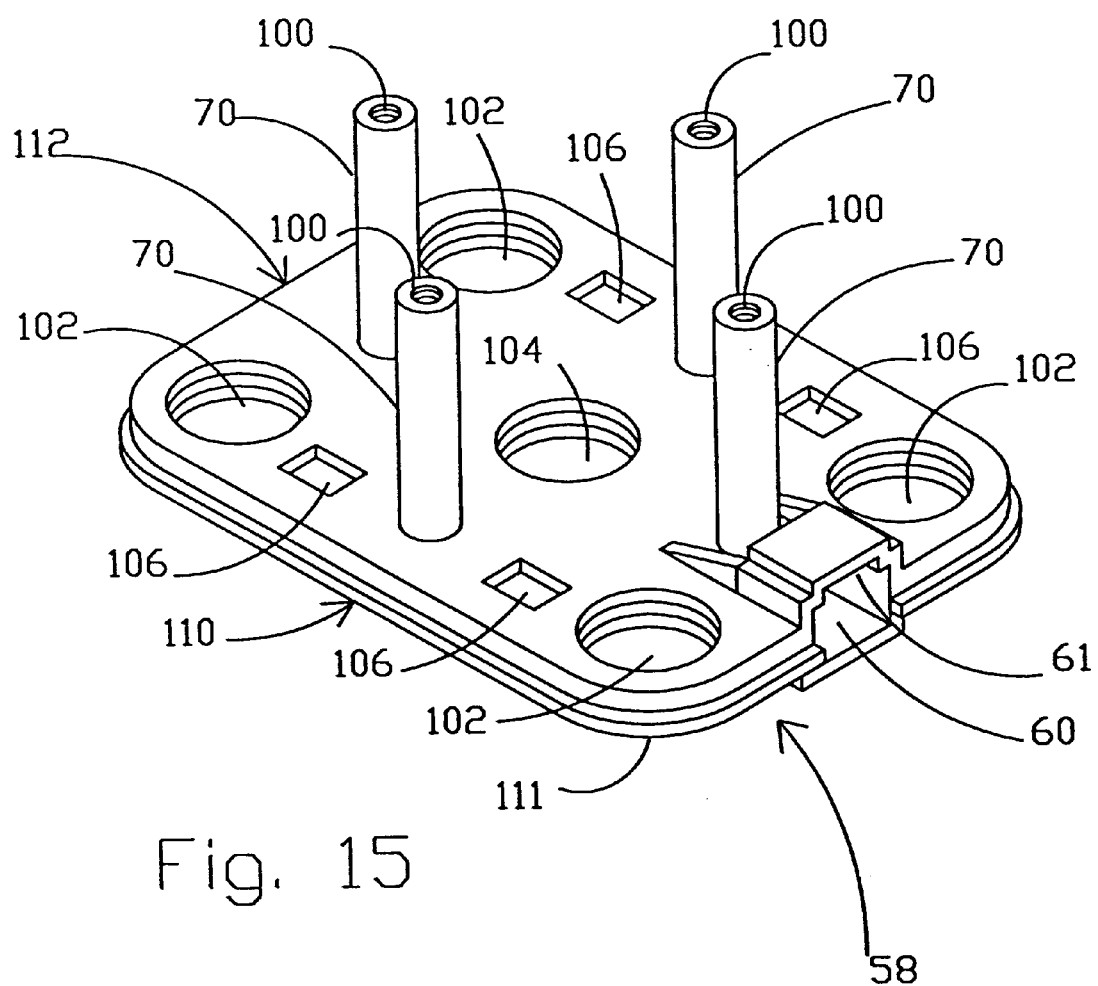
FIG. 15 is a diagram of the base portion of the locking-targeting-guide of FIG. 10.

Within the bottom frame 575 there is an armature 574 that has a plurality of universal joints 576a. Above each universal joint 576a is a respective brake-bearing 564. Armature 574 and universal joints 576a are substantially similar to armature 74 and lower universal joints 76a (FIGS. 11 and 13). The armature 574 is positioned above a uniform compression distributor 528.

The uniform compression distributor 528 may be formed from a sheet of firm compressible closed cell foam 534 or similar compressible expandable material that will deform when pressure is applied to it but exert pressure against the deforming force. Release of the deforming force will permit the closed cell foam 534 to expand to its original shape. Interposed between the sheet of closed cell foam 534 and beneath the armature 574 is a smooth rigid slide sheet 532. The armature 574 may slide through a number of degrees of freedom on the slide sheet 532. The undersurface of the armature 574 and the slide sheet 532 are composed of materials having a relatively low coefficient of friction, such as Teflon or the like.

Figure 10:
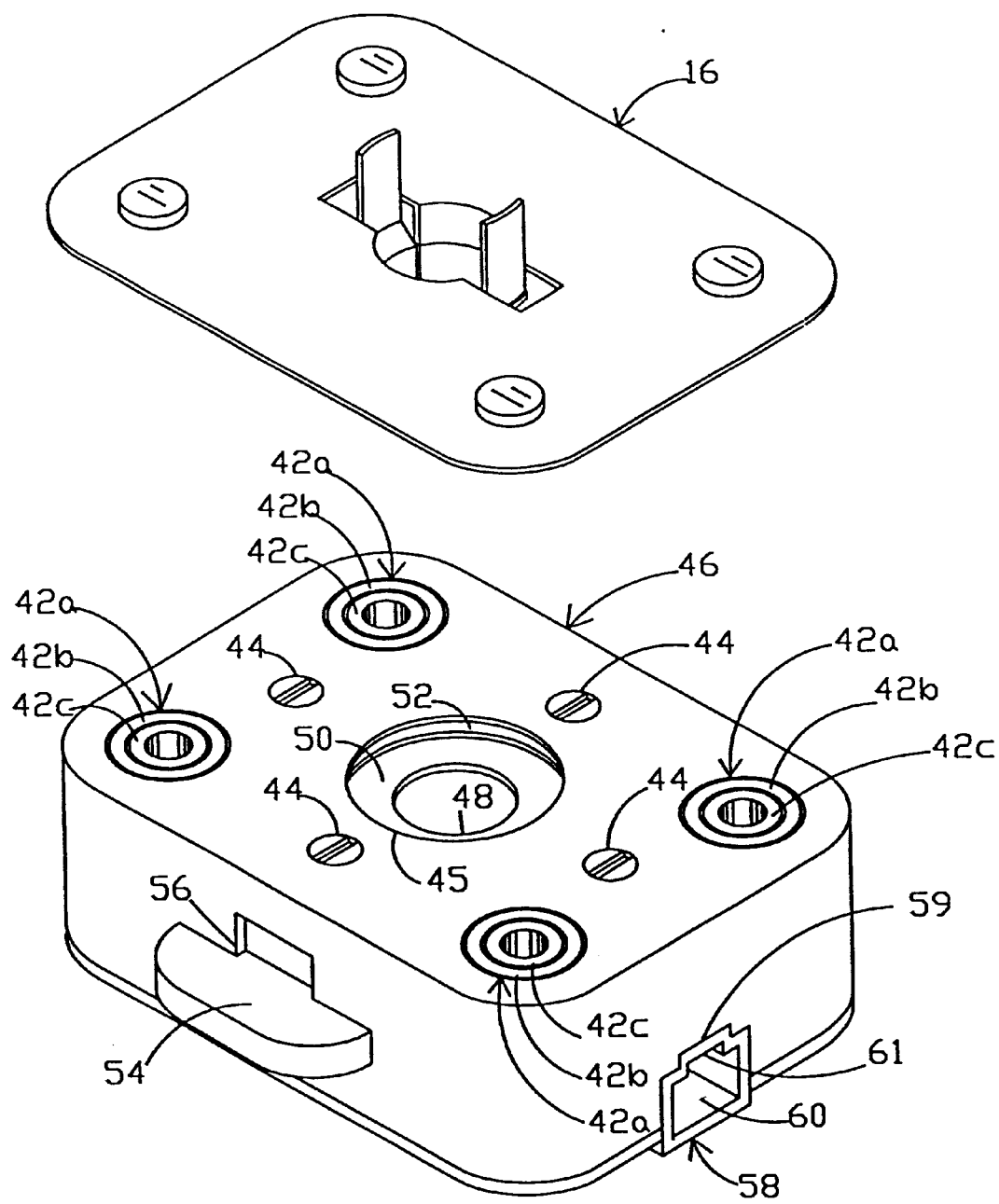
FIG. 10 is a diagram of a locking-targeting-guide and the alignment rod restraining plate of FIG. 2.
Figure 42:
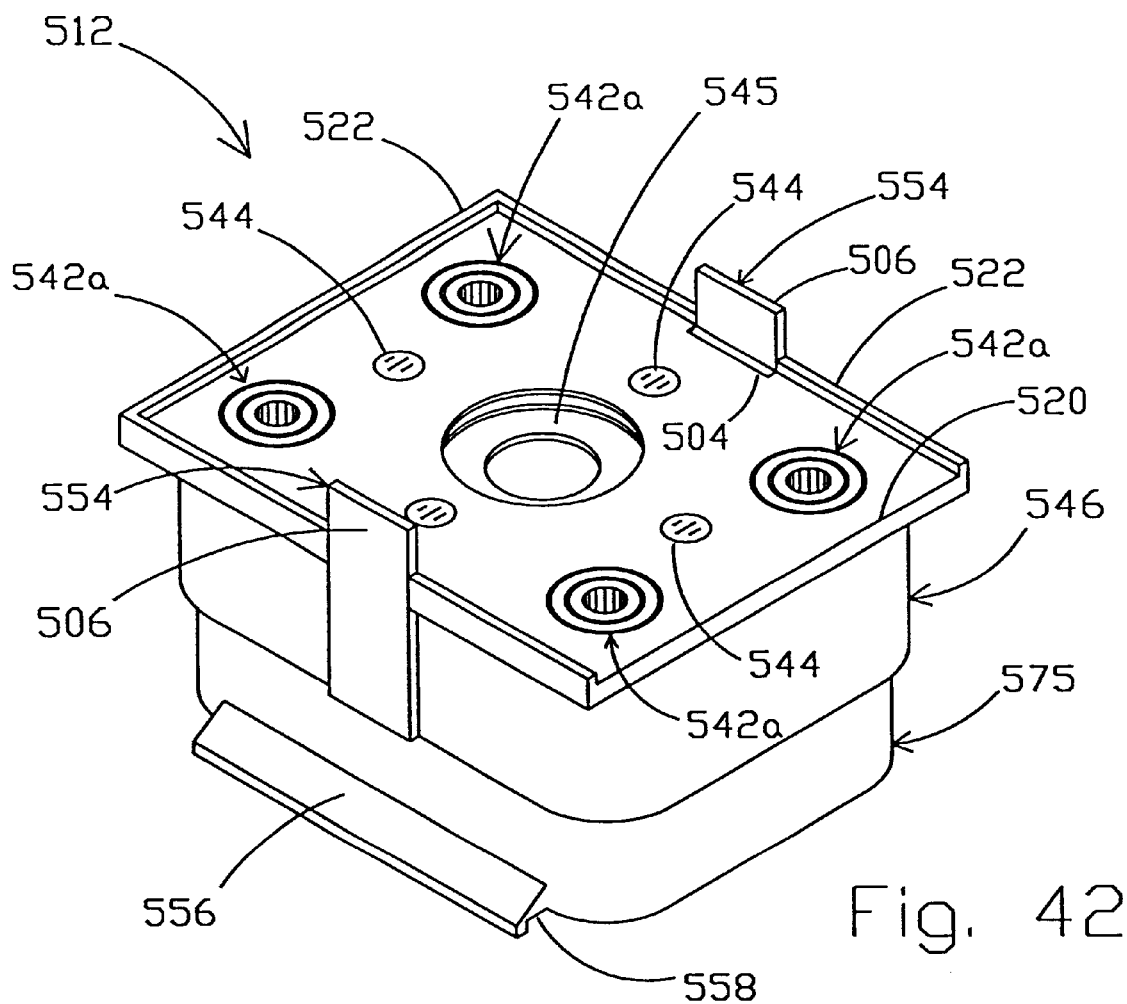
FIG. 42 is a diagram of the locking-targeting-guide of FIG. 40.

With reference to FIG. 42, the upper surface 520 of the top frame 546 has a plurality of universal joints 542a that are substantially similar to and function in a substantially similar manner to the universal joints 42a of locking-targeting-guide 12 (FIG. 10). In the center of the upper surface 520 is a relatively large central fenestration 545. The central fenestration 545 is substantially similar to the large central fenestration 45 of locking-targeting-guide 12. The central fenestration 545 will accept the previously described alignment rod restraining plate 16 (FIG. 2), the targeting insert 24, and the cannulated insert 34 (FIGS. 7, 8, 9).

Activation of the locking mechanism of the brake-bearings 564 against the vertical alignment rods 146 is produced by compression of the universal joints 542a and 576a against the upper and lower hemispheres of the brake-bearing 564 (FIG. 43). This compression is partially achieved by compressing the top frame 546 and bottom frame 575 together. Contact of the upper universal joints 542a and lower universal joints 576a against the upper and lower hemispheres of the brake-bearings 564 occurs before the bottom frame 575 has been locked to the top frame 546. The additional compression required to lock the bottom frame 575 to the top frame 546 may compress the armature 574 against the uniform compression distributor 528.

The pressure of the armature 574 against the universal compression distributor 528 is resisted by the closed cell foam 534. The compressed closed cell foam 534 will exert an expansion pressure against the armature 574. The pressure of the universal compression distributor 528 against the armature 574 ensures adequate sustained compression of the universal joints 542a and 576a against the brake-bearings 564 so as to provide sustained locking of the brake-bearings 564 against the vertical alignment rods 146.

With reference to FIGS. 40, 41, 44a, and 44b, positioning handle 514 will be described. The handle 514 may function in a substantially similar fashion as handle 14 (FIG. 1). That is, handle 514 will releasably rigidly couple to the locking-targeting-guide 512, will activate the lock mechanism within the locking-targeting-guide 512 against the vertical alignment rods, and upon locking the locking-targeting-guide 512 in the desired position the handle 514 can be uncoupled from locking-targeting-guide 512.

A number of elements of the handle 514 are different from handle 14. Handle 514 may have five major components that include an upper compression fork 594, a lower compression fork 598, a handle body 604, a handle trigger 602, and a spring 502. The handle trigger 602 and the handle body 604 may be pivotally linked together through axle 608. The handle trigger 602 and the handle body 604 may be pivotally linked to both the upper compression fork 594 and the lower compression fork 598.

The front end of the handle body 604 terminates in a linking fork 612. The linking fork 612 has a fixed pivot 606 with the rear end of the upper compression fork. The linking fork has a sliding pivot 618 with a slide groove 622 in the lower compression fork 598. The front end of the trigger 602 terminates in a linking fork 614. The linking fork 614 has a fixed pivot 610 with the rear end of the lower compression fork. The linking fork 614 has a sliding pivot 616 with a slide groove 620 in the upper compression fork 594.

Arising from the rear top surface of the handle-trigger 602 is a vertical flexible latch stem 508 which is substantially normal to the long axis of the handle-trigger. The vertical flexible latch stem 508 terminates in a latch 538. The flexible latch stem 508 and latch 538 are substantially similar to and function in a substantially similar manner to flexible latch stem 208 and latch 214 of handle trigger 198 (FIG. 36). Two lock/release controllers are arranged or molded into opposites sides of the inner walls of the handle body 604 that are substantially similar to and function in a substantially similar manner to the lock-release controller 214 (FIG. 36).

The spring 502 distracts the handle body 604 from the handle trigger 602. When the handle body is maximally distracted from the trigger 602, the interval between upper compression fork 594 and lower compression fork 598 is at a maximum. Such maximum interval between the upper compression fork 594 and the lower compression fork 598 is greater than the maximal height of the locking-targeting-guide 512 when springs 568 (FIG. 43) are maximally expanded.

Compressing the handle trigger 602 towards handle body 604 will narrow the interval between the upper compression fork 594 and the lower compression fork 598. The upper compression fork 594 and lower compression fork 598 are arranged so as to be substantially parallel to one another even as the interval between forks 594 and 598 is narrowed.

The upper compression fork terminates in a pair of tines 596. The tines 596 are adapted to engage the top surface 520 of the locking-targeting-guide 512. The locking-targeting-guide 512 has an elevated ridge 522 (FIG. 42) that guides and positions the tines 596. The lower compression fork 598 terminates in a pair of tines 600. Top surfaces 626 of tines 600 may engage lower surfaces of buttresses 556 (FIG. 42) of the bottom frame 575 of the locking-targeting-guide 512.

The locking-targeting-guide 512 is adapted to be grasped-and compressed by the handle 514. The sequence of the engagement and operation of the handle 514 with the locking-targeting-guide 512 is described below.

The fully expanded locking-targeting-guide 512 is placed into the interval between the upper and lower compression forks 594 and 598. The trigger 602 is squeezed against the force of the spring 502 and the interval between the compression forks 594 and 598 is narrowed such that the compression forks 594 and 598 engage the top and bottom of the locking-targeting-guide 512. Compression on the trigger 502 is continued. The continued compression will continue to narrow the interval between the compression forks 594 and 598 and initiate compression between the bottom frame 575 and the top frame 546 of the locking-targeting-guide 512 against the force of springs 568. Compression of the trigger is continued until the latch 538 engages and locks with the lock-release controller in the handle body 604. When the trigger 602 is locked to the handle body 604, the lock is sustained by the compressed spring 502. When the locking-targeting-guide 512 is compressed between the upper and lower compression forks 594 and 598, the expansible force of the compressed spring(s) 568 rigidly couples the locking-targeting-guide 512 to the handle 514. The handle 514 can now be used to move the locking-targeting-guide 512 to a desired position.

When the desired position of the locking-targeting-guide 512 is selected, the trigger 602 is squeezed another time. Such additional compression of the trigger 602 will produce further compression between the bottom frame 575 and the top frame 546 and produce compression of the brake-bearings 564 against the vertical alignment rods and locking of the bottom frame 575 to the top frame 546. Compression of the trigger 602 may be terminated when an operator hears a first click caused by the activation of the lock mechanism in locking-targeting-guide 512 and a second click as the latch 538 passes over the lock-release controller. Release of the trigger 602 will permit the spring 502 to expand and maximally widen the interval between the upper and lower compression forks'so as to enable the handle 514 to be uncoupled from-the locking-targeting-guide 512.

Reactivation of the locking-targeting-guide 512 is achieved by compressing the upper outer surface 506 of the lock-release levers 554 (FIG. 42). This will release the bottom frame 575 from top frame 546 and permit the locking-targeting-guide 512 to re-expand and release the brake-bearings 564 from the vertical alignment rods 146. Thereafter, handle 514 can be coupled to the locking-targeting-guide 512 and the process of moving and locking of the locking-targeting-guide in another desired position repeated.

Figure 47:
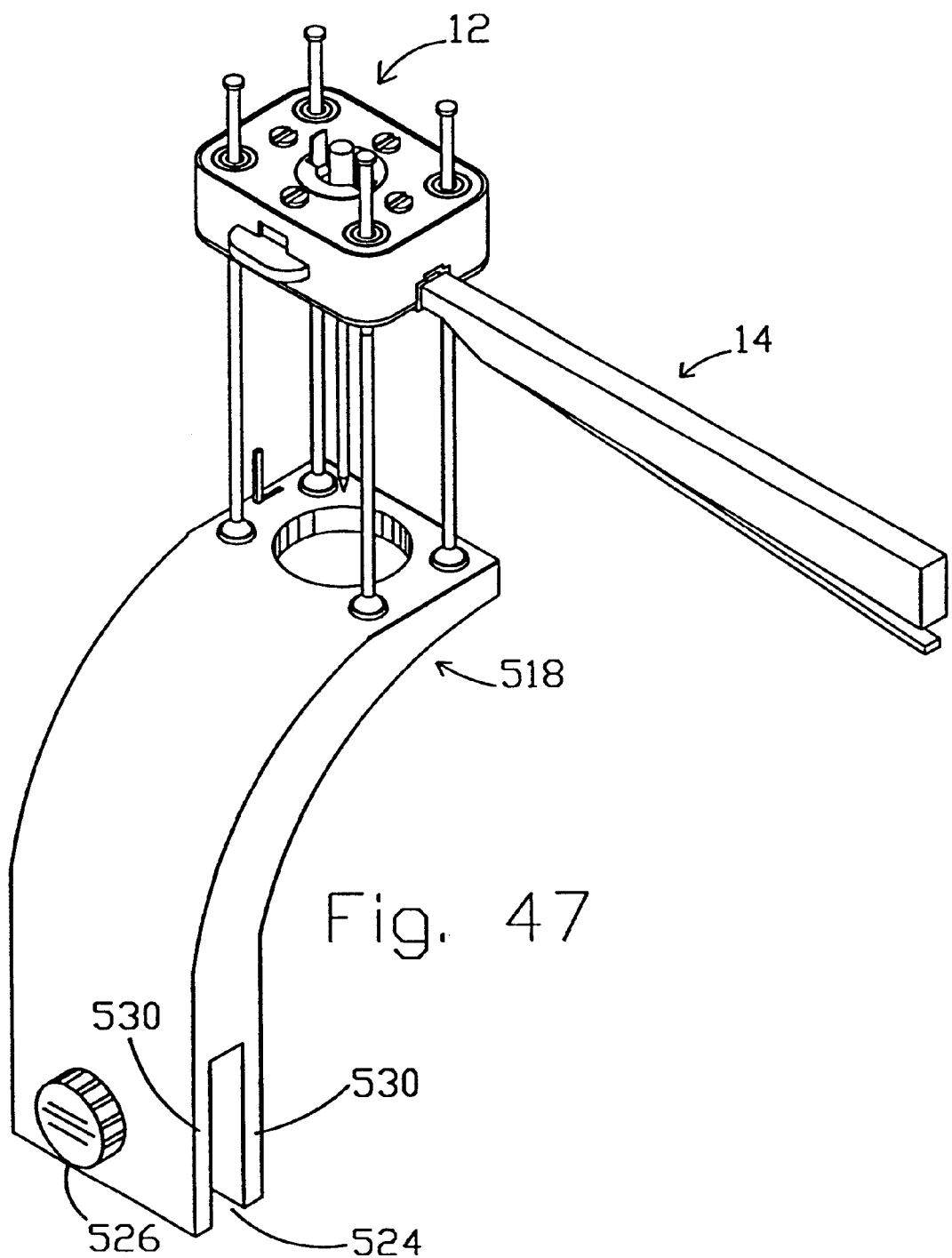
FIG. 47 is a diagram of a foundation according to another embodiment of the present invention.
Figure 48:
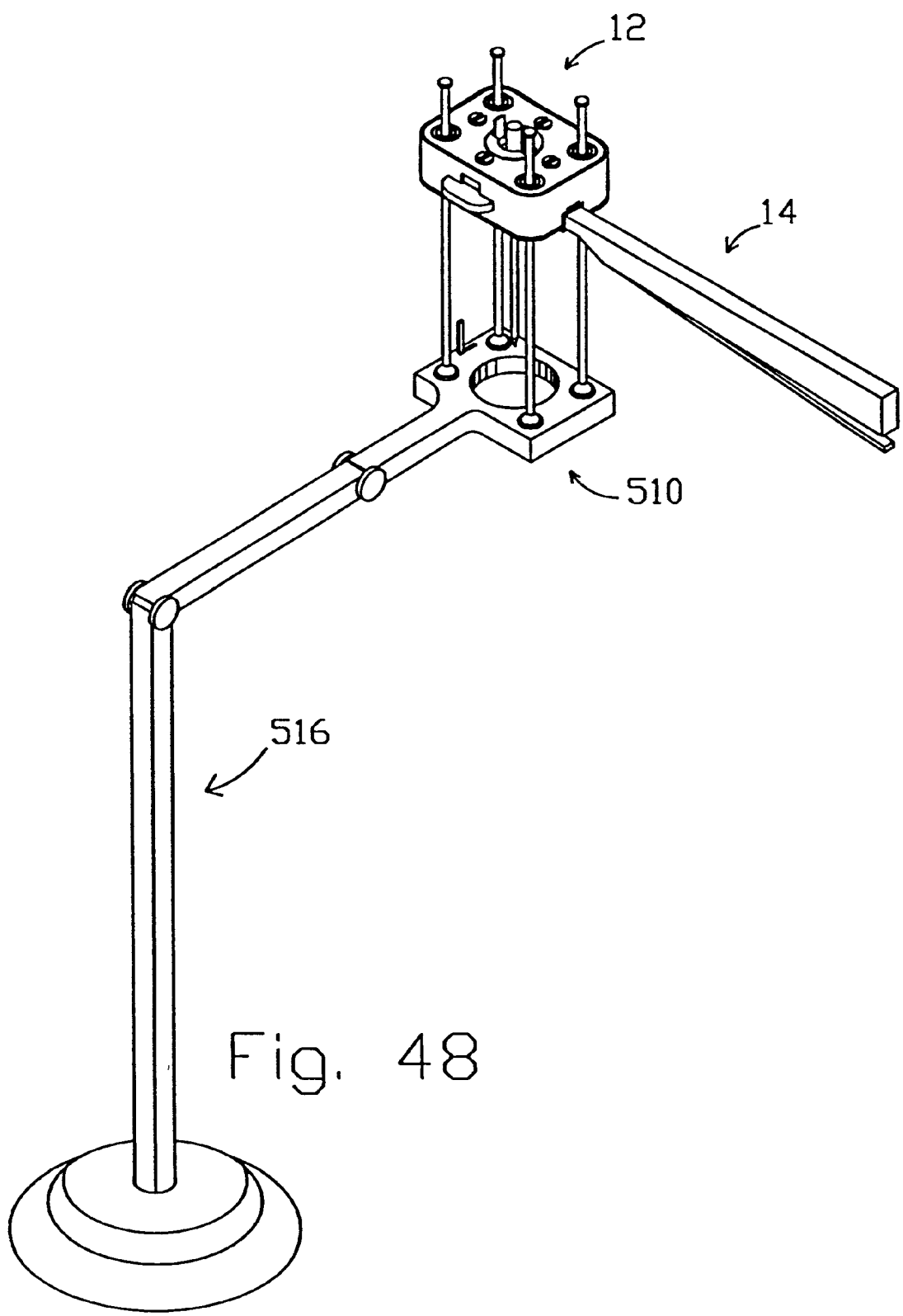
FIG. 48 is a diagram of a foundation according to another embodiment of the present invention.

Alternative embodiments of foundation 10 (FIGS. 1 and 28) will now be described with reference to FIGS. 47 and 48.

Foundation 518 is similar to the foundation 10, except that the foundation 518 may be mounted directly to a hospital bed, an operative table or a radiographic table. Hospital beds, operative tables, and radiographic imaging tables have side rails to which portable medical equipment can be releasably attached. The foundation 518 has an opening or tenon 524 with two sides 530 adapted to be arranged on the side rail and may be held in place by tightening knob 526. Foundation 510 is similar to the foundation 10, except that foundation 510 is pivotally attached to an independent free standing portable armature 516, as shown in FIG. 48.

Accordingly, the present invention provides a technique for targeting and/or installing distal locking screws into intramedullary nails which is relatively simple and intuitive to use. The present technique may be used with equipment presently available, in most, if not all, hospitals and as such does not require additional and possibly expensive pieces of equipment. The present technique substantially minimizes x-ray exposure through the above-described four steps of distal screw placement and yet will enable a rapid and reliable guide for the drilling of the distal screw holes, the measuring of the locking screw(s) and the placement of the locking screw(s). Further, the present technique may significantly decrease operating room time. Furthermore, the present apparatus may be almost completely radiolucent. Additionally, since a number of the parts/elements of the present apparatus may be fabricated or molded from plastic, the present invention is relatively inexpensive and may be disposable.

Although the present apparatus has been described with certain types and/or numbers of elements, the present apparatus is not so limited and may instead have other types and/or numbers of elements. For example, although the present apparatus was described as having four vertical alignment rods 146 and four break-bearing devices 64, the present apparatus may instead have three (or another number) of such rods and/or break-bearing devices. As another example, although the present apparatus was described as having an equal number of assembled vertical alignment rods, brake-bearings 64, and universal joints, the present apparatus is not so limited and may have an unequal number of such elements.

Further, although the present apparatus has been described for use with distal locking screws, the present apparatus is not so limited and may instead be used with proximal locking and other types of fasteners.

Furthermore, although embodiments of the present invention have been described for use in the placement of orthopaedic screws into an implanted intramedullary nail, the present invention is not so limited and is not limited to orthopaedic applications. That is, the present invention can be applied in any medical situation or procedure where a position is to be determined and maintained. For example, the present invention may be used for x-ray guided biopsies, x-ray guided placement of a catheter for drainage of an abscess or similar abnormal collection of fluid and so forth.

Although preferred embodiments of the present invention and modifications thereof have been described in detail herein, it is to be understood that this invention is not limited to these embodiments and modifications, and that other modifications and variations may be effected by one skilled in the art without departing from the spirit and scope of the invention as defined by the appended claims.

What is claimed is:

1. An apparatus for installing a number of distal screws into an intramedullary nail implanted in a patient, said apparatus comprising:

a foundation unit adapted to be fixedly coupled to said patient;

a targeting/guiding unit adapted to be attached to said foundation unit and adaptable for targeting and guiding a device or devices used in installing a respective distal screw into a distal hole in said intramedullary nail, said targeting/guiding unit being movable to a desired location by an operator when attached to said foundation device so as to be aligned with the respective distal screw hole, wherein said targeting/guiding unit includes a locking device for holding said targeting/guiding unit in said desired location;

a handle adapted to be coupled to said targeting/guiding unit for facilitating the movement thereof by said operator, wherein said handle includes means for activating said locking device.

2. A apparatus according to claim 1, wherein said targeting/guiding unit further includes means for releasing said locking device such that said targeting/guiding unit is not held in said desired location.

3. An apparatus according to claim 1, wherein said foundation unit includes a number of alignment rods and wherein said targeting/guiding unit is attachable to said number of alignment rods.

4. An apparatus according to claim 3, wherein said number of alignment rods are movably arranged in said foundation device.

5. An apparatus according to claim 4, wherein said locking device includes a number of brake elements each coupled to a respective alignment rod.

6. An apparatus according to claim 1, wherein said handle further includes means for de-coupling said handle from said targeting/guiding unit when the activating means activates said locking device.

* * * * *